United States Patent
Gombert et al.

(10) Patent No.: US 8,883,720 B2
(45) Date of Patent: Nov. 11, 2014

(54) TEMPLATE-FIXED BETA-HAIRPIN PEPTIDOMIMETICS WITH CXCR4 ANTAGONIZING ACTIVITY

(75) Inventors: Frank Gombert, Basel (CH); Daniel Obrecht, Bättwil (CH); Alexander Lederer, Basel (CH); Barbara Romagnoli, Allschwil (CH)

(73) Assignee: Polyphor AG, Allschwil (CH)

( * ) Notice: Subject to any disclaimer, the term of this patent is extended or adjusted under 35 U.S.C. 154(b) by 551 days.

(21) Appl. No.: 13/131,205

(22) PCT Filed: Nov. 26, 2008

(86) PCT No.: PCT/EP2008/066270
§ 371 (c)(1),
(2), (4) Date: Aug. 15, 2011

(87) PCT Pub. No.: WO2010/060479
PCT Pub. Date: Jun. 3, 2010

(65) Prior Publication Data
US 2011/0312879 A1    Dec. 22, 2011

(51) Int. Cl.
```
A01N 37/18     (2006.01)
A61K 38/00     (2006.01)
A61P 29/00     (2006.01)
A61P 35/00     (2006.01)
C07K 14/515    (2006.01)
C07K 7/08      (2006.01)
C07K 7/64      (2006.01)
C07K 1/04      (2006.01)
```
(52) U.S. Cl.
CPC ... *C07K 7/64* (2013.01); *C07K 7/08* (2013.01); *C07K 1/047* (2013.01)
USPC ............................ 514/3.8; 514/12.2; 514/13.3

(58) Field of Classification Search
CPC .............. C07K 1/00; C07K 7/08; C07K 7/64
See application file for complete search history.

(56) References Cited
U.S. PATENT DOCUMENTS
2011/0135576 A1* 6/2011 DeMarco et al. .............. 424/9.5

FOREIGN PATENT DOCUMENTS

| WO | WO 02/070547 A1 | 9/2002 | |
|---|---|---|---|
| WO | WO 2004/096839 A1 | 11/2004 | |
| WO | WO 2004/096840 A1 | 11/2004 | |
| WO | WO 2006/117011 | * 11/2006 | ............... C07K 7/64 |

OTHER PUBLICATIONS

Wang et al. Dipeptidyl aspartyl fluoromethylketones as potent caspase inhibitors: peptidomimetic replacement of the P2 alpha-amino acid by a alpha-hydroxy acid. Bioorganic & Medicinal Chemistry Letters (2005), vol. 15, pp. 1379-1383.*
International Search Report dated Dec. 22, 2009 for PCT/EP2008/066270.

* cited by examiner

*Primary Examiner* — Marcela M Cordero Garcia
(74) *Attorney, Agent, or Firm* — Birch, Stewart, Kolasch & Birch, LLP

(57) ABSTRACT

Template-fixed peptidomimetics formula (Ia) formula (Ib) wherein Z is a template-fixed chain of 14 α-amino and/or α-hydroxy acid residues which, depending on their positions in the chain (counted starting from the N-terminal amino acid), are Pro, Gly, a glycolic acid residue or of certain types which, as the remaining symbols in the above formulae, are defined in the description and the claims, and salts thereof, have CXCR4 antagonizing properties and can be used for preventing HIV infections in non-infected individuals or for slowing and halting viral progression in infected patients; or where cancer is mediated or resulting from CXCR4 receptor activity; or where immunological diseases are mediated or resulting from CXCR4 receptor activity; or for treating immuno suppression; or during apheresis collections of peripheral blood stem cells and/or as agents to induce mobilization of stem cells to regulate tissue repair. These depsipeptides can be manufactured by a process which is based on a mixed solid- and solution phase synthetic strategy.

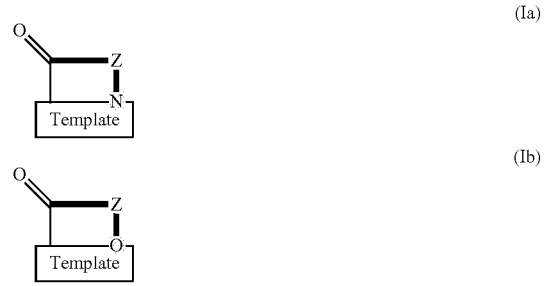

33 Claims, No Drawings

TEMPLATE-FIXED BETA-HAIRPIN PEPTIDOMIMETICS WITH CXCR4 ANTAGONIZING ACTIVITY

The present invention provides template-fixed β-hairpin peptidomimetics incorporating template-fixed chains of 14 α-amino acid residues which, depending on their positions in the chains, are Pro, Gly, a Glycolic acid residue or of certain types, as defined herein below, at least one of these α-amino acid residues being replaced by an α-hydroxy acid residue of a certain type, as defined herein below, and/or the template containing such α-hydroxy acid residue. These template-fixed depsipeptides have CXCR4 antagonizing activity. In addition, the present invention provides an efficient synthetic process by which these compounds can, if desired, be made in parallel library-format. These β-hairpin peptidomimetics show improved efficacy, bioavailability, and most importantly a significantly enhanced ratio between CXCR4 antagonizing activity on the one hand, and hemolysis on red blood cells and cytotoxicity on the other.

Many medically significant biological processes are mediated by signal transduction that involves chemokines and their receptors in general and stromal derived factor 1 (SDF-1/CXCL12) and its receptor CXCR4 in particular.

CXCR4 and its ligand SDF-1 are involved in trafficking of B cells, hematopoietic stem cells (HSC) and hematopoietic progenitor cells (HPC). For instance, CXCR4 is expressed on CD34+ cells, and has been implicated in the process of CD34+ cell migration and homing (S. M. Watt, S. P. Forde, *Vox sanguinis* 2008, 94, 18-32). It has also been shown that the CXCR4 receptor plays an important role in the release of stem and progenitor cells from the bone marrow to the peripheral blood (L. M. Pelus, S. Fukuda, *Leukemia* 2008, 22, 466-473). This activity of CXCR4 could be very important for efficient apheresis collections of peripheral blood stem cells. Autologous peripheral blood cells provide a rapid and sustained hematopoietic recovery following auto-transplantation after the administration of high-dose chemotherapy or radiotherapy in patients with haematological malignancies and solid tumors. (W. C. Liles et al., *Blood* 2003, 102, 2728-2730).

Recently, it has been demonstrated that SDF-1 is locally up-regulated in animal models of injury including focal ischemic stroke, global cerebral ischemia, myocardial infarction and hind limb ischemia as well as being involved in recovery after peripheral ischemia or following injury to the liver, kidney or lung (A. E. Ting, R. W. Mays, M. R. Frey, W. Van't Hof, S. Medicetty, R. Deans, *Critical Reviews in Oncology/Hematology* 2008, 65, 81-93 and literature cited herein; F. Lin, K. Cordes, L. Li, L. Hood, W. G. Couser, Shankland et al., *J. Am. Soc. Nephrol.* 2003, 14, 1188-1199; C. C. Dos Santos, *Intensive Care Med.* 2008, 34, 619-630). These results suggest that SDF-1 may chemoattract CXCR4-positive stem cells for tissue and organ repair/regeneration (M. Z. Ratajczak, M. Kucia, R. Reca, M. Majka, A. Janowska-Wieczorek, J. Ratajczak, *Leukemia* 2004, 18, 29-40). Therefore, modulating the SDF-1/CXCR4 axis by CXCR4 inhibitors should result in a significant therapeutic benefit by using released stem cells to regulate tissue repair.

There is increasing evidence that implies that chemokines in general and the SDF-1/CXCR4 interaction in particular plays a pivotal role in angiogenesis. Chemokines induce angiogenesis directly by binding their cognate receptors on endothelial cells or indirectly by promoting inflammatory cell infiltrates, which deliver other angiogenic stimuli. A number of proinflammatory chemokines including interleukin 8 (IL-8), growth-regulated oncogene, stromal cell-derived factor 1 (SDF-1), monocyte chemotactic protein 1 (MCP-1), eotaxin 1, and 1-309 have been shown to act as direct inducers of angiogenesis. (X. Chen, J. A. Beutler, T. G. McCloud, A. Loehfelm, L. Yang, H. F. Dong, O. Y. Chertov, R. Salcedo, J. J. Oppenheim, O. M. Howard. *Clin. Cancer Res.* 2003, 9(8), 3115-3123; R. Salcedo, J. J. Oppenheim, *Microcirculation* 2003, (3-4), 359-370).

Recently obtained results show that the CXCR4 receptor is involved in the chemotactic activity of cancer cells, such as breast cancer metastasis or in metastasis of ovarian cancer (A. Muller, B. Homey, H. Soto, N. Ge, D. Catron, M. E. Buchanan, T. Mc Clanahan, E. Murphey, W. Yuan, S. N. Wagner, J. L. Barrera, A. Mohar, E. Verastegui, A. Zlotnik, *Nature* 2001, 50, 410; J. M. Hall, K. S. Korach, *Molecular Endocrinology* 2003, 17, 792-803.), Non-Hodgin's Lymphoma (F. Bertolini, C. Dell'Agnola, P. Manusco, C. Rabascio, A. Burlini, S. Monestiroli, A. Gobbi, G. Pruneri, G. Martinelli, *Cancer Research* 2002, 62, 3106-3112), or lung cancer (T. Kijima, G. Maulik, P. C. Ma, E. V. Tibaldi, R. E. Turner, B. Rollins, M. Sattler, B. E. Johnson, R. Salgia, *Cancer Research* 2002, 62, 6304-6311), melanoma, prostate cancer, kidney cancer, neuroblastomia, pancreatic cancer, multiple myeloma, chronic lymphocytic leukemia (H. Tamamura et al., *FEBS Letters* 2003, 550, 79-83, cited ref.). Blocking the chemotactic activity with a CXCR4 inhibitor should stop the migration of cancer cells.

CXCR4 has also been implicated in the growth and proliferation of tumors. It was shown that activation of the CXCR4 receptor was critical for the growth of both malignant neuronal and glial tumors, and small cell lung tumors. Moreover, systemic administration of the CXCR4 antagonist AMD3100 inhibits growth of intracranial glioblastoma and medulloblastoma xenografts by increasing apoptosis and decreasing the proliferation of tumor cells (J. B. Rubin, A. L Kung, R. S Klein, J. A. Chan, Y. Sun, K. Schmidt, M. W. Kieran, A. D. Luster, R. A. Segal, *Proc Natl Acad Sci USA.* 2003, 100(23), 13513-13518, S. Barbero, R. Bonavia, A. Bajetto, C. Porcile, P. Pirani, J. L. Ravetti, G. L. Zona, R. Spaziante, T. Florio, G. Schettini, *Cancer Res.* 2003, 63(8), 1969-1974, T. Kijima, G. Maulik, P. C. Ma, E. V. Tibaldi, R. E. Turner, B. Rollins, M. Sattler, B. E. Johnson, R. Salgia. *Cancer Res.* 2002, 62(21), 6304-6311; F. Bertolini, C. Dell'Agnola, P. Mancuso, C. Rabascio, A. Burlini, S. Monestiroli, A. Gobbi, G. Pruneri, G. Martinelli *Cancer Res.* 2002, 62(11), 3106-3112.

It is well established that chemokines are involved in a number of inflammatory pathologies and some of them show a pivotal role in the modulation of osteoclast development. Immunostaining for SDF-1 (CXCL12) on synovial and bone tissue biopsies from both rheumatoid arthritis (RA) and osteoarthritis (OA) samples have revealed strong increases in the expression levels of chemokines under inflammatory conditions (F. Grassi, S. Cristino, S. Toneguzzi, A. Piacentini, A. Facchini, G. Lisignoli, *J. Cell Physiol.* 2004; 199(2), 244-251). It seems likely that the CXCR4 receptor plays an important role in inflammatory diseases such as rheumatoid arthritis, asthma, or multiple sclerosis (K. R. Shadidi et al., *Scandinavian Journal of Immunology* 2003, 57, 192-198; J. A. Gonzalo, *J. Immunol.* 2000, 165, 499-508; S. Hatse et al., *FEBS Letters* 2002, 527, 255-262 and cited references). The mediation of recruitment of immune cells to sites of inflammation should be stopped by a CXCR4 inhibitor.

To date the available therapies for the treatment of HIV infections have been leading to a remarkable improvement in symptoms and recovery from disease in infected people. Although the highly active anti retroviral therapy (HAART) which involves a combination of reverse transcriptase/protease-inhibitor has dramatically improved the clinical treatment of individuals with AIDS or HIV infection, there have still remained several serious problems including multi drug resistance, significant adverse effects and high costs. Particularly desired are anti HIV agents that block the HIV infection at an early stage of the infection, such as the viral entry. It has recently been recognized that for efficient entry into target cells, human immunodeficiency viruses require the chemokine receptors CCR5 and CXCR4 as well as the primary receptor CD4 (N. Levy, Engl. J. Med. 1996, 335, 1528-1530). Accordingly, an agent which could block the CXCR4 chemokine receptors should prevent infections in non-infected individuals and slow or halt viral progression in infected patients (J. Cohen, Science 1997, 275, 1261-1264).

Among the different types of CXCR4 inhibitors (M. Schwarz, T. N. C. Wells, A. E. I. Proudfoot, Receptors and Channels 2001, 7, 417-428), one emerging class is based on naturally occurring cationic peptide analogues derived from Polyphemusin II which have an antiparallel β-sheet structure, and a β-hairpin that is maintained by two disulfide bridges (H. Nakashima, M. Masuda, T. Murakami, Y. Koyanagi, A. Matsumoto, N. Fujii, N. Yamamoto, Antimicrobial Agents and Chemoth. 1992, 36, 1249-1255; H. Tamamura, M. Kuroda, M. Masuda, A. Otaka, S. Funakoshi, H. Nakashima, N. Yamamoto, M. Waki, A. Matsumotu, J. M. Lancelin, D. Kohda, S. Tate, F. Inagaki, N. Fujii, Biochim. Biophys. Acta 1993, 209, 1163; WO 95/10534 A1).

Synthesis of structural analogs and structural studies by nuclear magnetic resonance (NMR) spectroscopy have shown that the cationic peptides adopt well defined β-hairpin conformations, due to the constraining effect of the one or two disulfide bridges (H. Tamamura, M. Sugioka, Y. Odagaki, A. Omagari, Y. Kahn, S. Oishi, H. Nakashima, N. Yamamoto, S. C. Peiper, N. Hamanaka, A. Otaka, N. Fujii, Bioorg. Med. Chem. Lett. 2001, 359-362). These results show that the β-hairpin structure plays an important role in CXCR4 antagonizing activity.

Additional structural studies have also indicated that the antagonizing activity can also be influenced by modulating amphiphilic structure and the pharmacophore (H. Tamamura, A. Omagari, K. Hiramatsu, K. Gotoh, T. Kanamoto, Y. Xu, E. Kodama, M. Matsuoka, T. Hattori, N. Yamamoto, H. Nakashima, A. Otaka, N. Fujii, Bioorg. Med. Chem. Lett. 2001, 11, 1897-1902; H. Tamamura, A. Omagari, K. Hiramatsu, S. Oishi, H. Habashita, T. Kanamoto, K. Gotoh, N. Yamamoto, H. Nakashima, A. Otaka N. Fujii, Bioorg. Med. Chem. 2002, 10, 1417-1426; H. Tamamura, K. Hiramatsu, K. Miyamoto, A. Omagari, S. Oishi, H. Nakashima, N. Yamamoto, Y. Kuroda, T. Nakagawa, A. Otaki, N. Fujii, Bioorg. Med. Chem. Letters 2002, 12, 923-928).

A key issue in the design of CXCR4 antagonizing peptides is selectivity. The polyphemusin II derived analogs exert still cytotoxicity despite improvements (K. Matsuzaki, M. Fukui, N. Fujii, K. Miyajima, Biochim. Biophys. Acta 1991, 259, 1070; A. Otaka, H. Tamamura, Y. Terakawa, M. Masuda, T. Koide, T. Murakami, H. Nakashima, K. Matsuzaki, K. Miyajima, T. Ibuka, M. Waki, A. Matsumoto, N. Yamamoto, N. Fujii Biol. Pharm. Bull. 1994, 17, 1669 and cited references above). This cytotoxic activity essentially obviates its use in vivo and represents a serious disadvantage in clinical applications. Before intravenous use can be considered, the general toxicity, protein-binding activity in blood serum, as well as protease stability become serious issues which must be adequately addressed.

In the compounds described below, a new strategy is introduced to stabilize beta-hairpin conformations in cyclic template-stabilized peptidomimetics exhibiting high CXCR4 antagonizing activity, being useful for efficient apheresis collections of mobilized peripheral blood stem cells and/or using these mobilized cells to regulate tissue repair, and having anticancer activity, anti inflammatory activity and anti HIV activity. This strategy involves transplanting the cationic and hydrophobic hairpin sequence onto a template, whose function is to restrain the peptide loop backbone into hairpin geometry. The rigidity of the hairpin may be further influenced by introducing a disulfide bridge. In addition, incorporation of structural elements derived from α-hydroxy acids into template-bound hairpin mimetics generating depsipeptides has been realized, a new approach which has not previously been evaluated for development of β-hairpin peptidomimetics with CXCR4 antagonizing activity.

Depsipeptides comprise a broad family of cyclic molecules containing amino and hydroxy acid residues connected by amide and ester bonds (V. T. Ivanov, I. I. Mikhaleva in Houben-Weyl, "Synthesis of Peptides and Peptidomimetics", Editor-in-Chief: M. Goodman, Editors: A. Felix, L. Moroder, C. Toniolo, 2004, Georg Thieme Verlag, Stuttgart, Bd. E22c, 272-291). Moreover, the vast majority of natural depsipeptides exhibit a diverse range of biological activities including antitumor, antiviral, antiinflammatory, immunosuppressant, antibiotic and antifungal activities of pharmacological and medical relevance (F. Sarabia, S. Chammaa, A. S. Ruiz, L. M. Ortiz, F. J. López Herrera, Curr. Med. Chem. 2004, 11, 1309-1332 and ref. cited herein; Y. Hamada, T. Shioiri, Chem. Rev. 2005, 105, 4441-4482).

Cyclic depsipeptide natural products are generally less stable towards chemical and enzymatic proteolysis in vitro and in vivo than the parent cyclic peptides (Review: F. von Nussbaum, M. Brands, B. Hinzen, S. Weigand, D. Häbich, Angew. Chem. Int. Ed. 2006, 45, 5072-5129; Lysobactin/Katanosin: A. A. Tymiak, T. J. McCormick, S. E. Unger, J. Org. Chem. 1989, 54, 1149-1157; Enopeptins: H. Brötz-Oesterhelt, D. Beyer, H. P. Kroll, R. Endermann, C. Ladel, W. Schroeder, B. Hinzen, S. Raddatz, H. Paulsen, K. Hennenger, J. E. Baldow, H. G. Sahl, H. Labischinski, Nat. Med. 2005, 11, 1082-1087; Aureobasidin: T. Kurome, T. Inoue, K. Takesako, I. Kato, J. Antibiot. 1998, 51, 359-367). This is also generally the case for template-fixed β-hairpin mimetic depsipeptides, although stable representatives are available as well.

A reduced in vivo proteolytic stability of some of the present cyclic depsipeptides, however, might be beneficial for therapeutic applications such as hematopoetic stem cell transplantation and tissue repair where a rapid onset of biological activity and relatively fast clearance of the compounds could be an advantage.

Template-bound hairpin mimetic peptides have been described in the literature (D. Obrecht, M. Altorfer, J. A. Robinson, Adv. Med. Chem. 1999, 4, 1-68; J. A. Robinson, Syn. Lett. 2000, 4, 429-441), and the ability to generate β-hairpin peptidomimetics using combinatorial and parallel synthesis methods has now been established (L. Jiang, K. Moehle, B. Dhanapal, D. Obrecht, J. A. Robinson, Helv. Chim. Acta. 2000, 83, 3097-3112). However, the additional incorporation of structure elements derived from α-hydroxy acids into template-bound hairpin mimetics by applying and altering these methods has not previously been evaluated for development of CXCR4 antagonizing peptides. The methods described here allow the synthesis and screening of large hairpin mimetic libraries, which in turn considerably facilitates structure-activity studies, and hence the discovery of new molecules with highly potent CXCR4 antagonizing activity or anti cancer activity or anti inflammatory activity or anti HIV activity and low hemolytic activity to human red blood cells.

β-Hairpin peptidomimetics obtained by the approach described here can be used in apheresis collections of peripheral blood stem cells and/or as agents to induce mobilization of stem cells to regulate tissue repair or are useful as anticancer agents, as inhibitors of tumor growth or as apoptosis inducing agents, as anti-metastasis agents, as anti inflammatory agents and as anti-HIV agents.

The β-hairpin peptidomimetics of the present invention are compounds of the general formulae

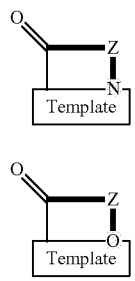

(Ia)

(Ib)

wherein

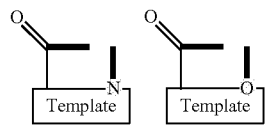

are groups of one of the formulae

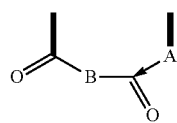

(a1)

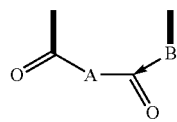

(a2)

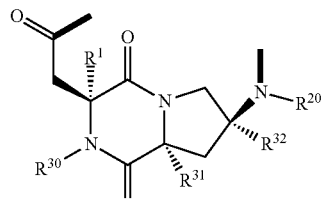

(b1)

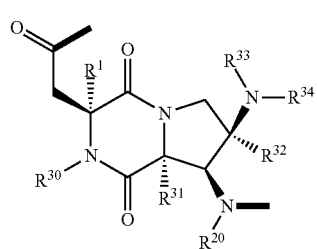

(b2)

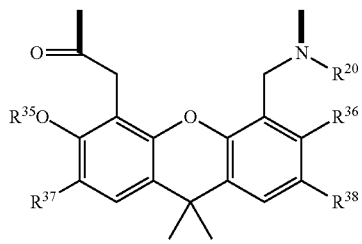

(c1)

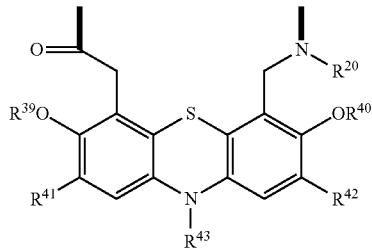

(c2)

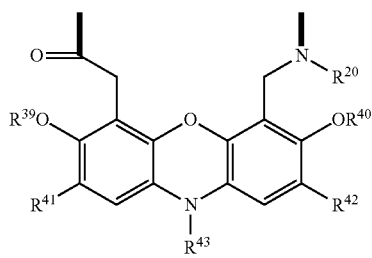

(c3)

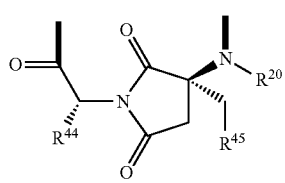

(d)

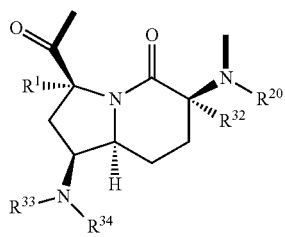

(e1)

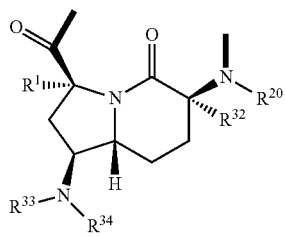

(e2)

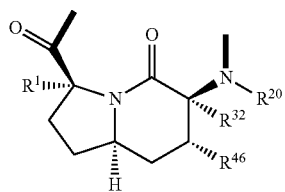

(e3)

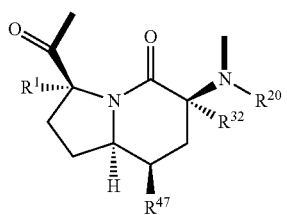 (e4)
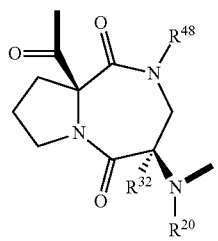 (f)
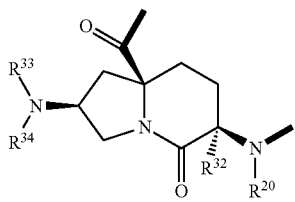 (g)
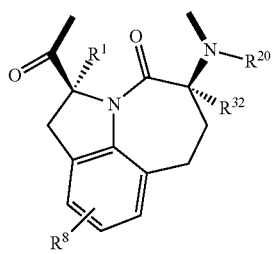 (h)
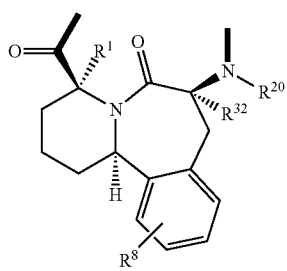 (i1)
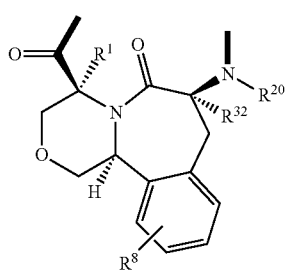 (i2)
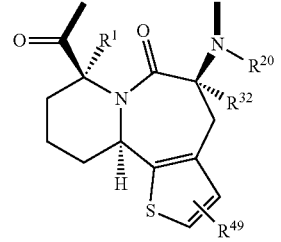 (i3)
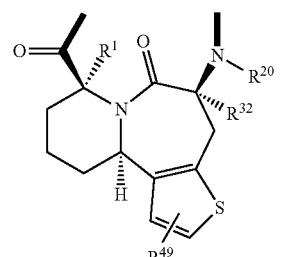 (i4)
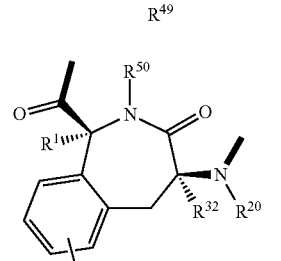 (j)
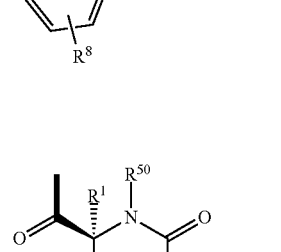 (k)
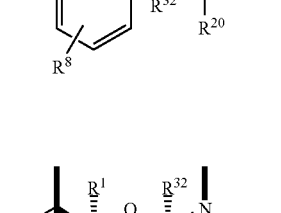
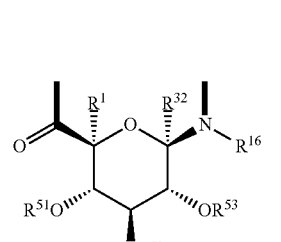 (l)
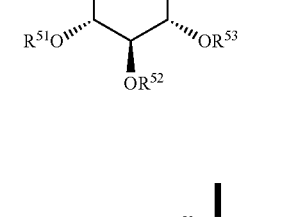
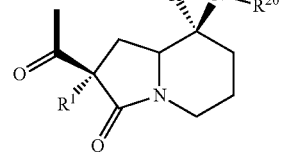 (m)

-continued (n)
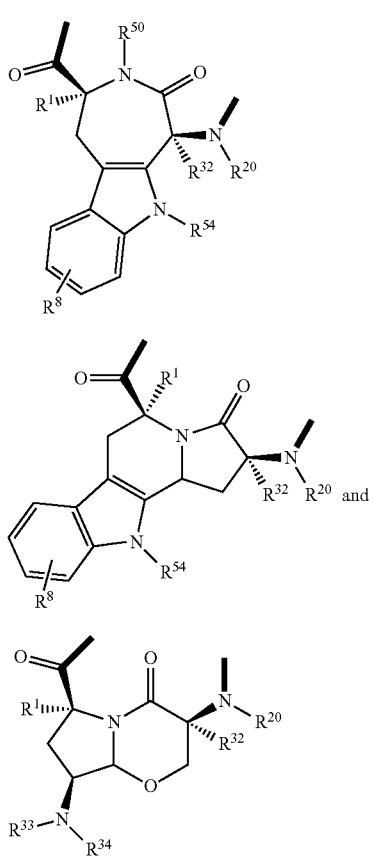

(o)

(p)

wherein

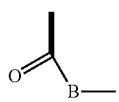

is Gly or a Glycolic acid residue, or the residue of an L-α-amino acid with B being a residue of formula —NR$^{20}$CH(R$^{71}$)—, or —NR$^{20}$CH(R$^{72}$)—, or —NR$^{20}$CH(R$^{73}$)— or —NR$^{20}$CH(R$^{74}$)— or —NR$^{20}$CH(R$^{84}$)— or the residue of an L-α-hydroxy acid with B being a residue of formula —OCH(R$^{71}$)— or —OCH(R$^{72}$)— or —OCH(R$^{73}$)— or —OCH(R$^{74}$)— or —OCH(R$^{84}$)—, or the enantiomer of one of the groups A1 to A69 and A105, or the enantiomer of the groups A106 to A110 as defined hereinafter;

is a group of one of the formulae

A1
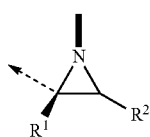

-continued

A2
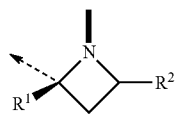

A3
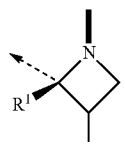

A4
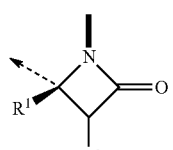

A5
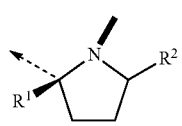

A6
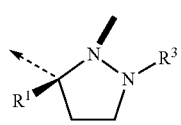

A7
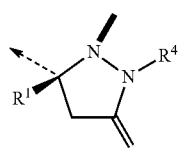

A8
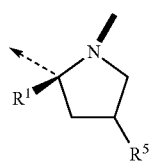

A9
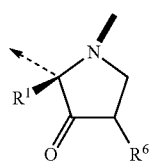

A10
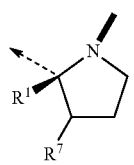

A11
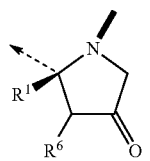

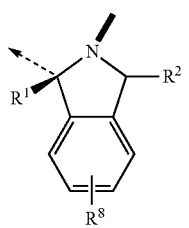 A12
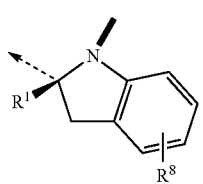 A13
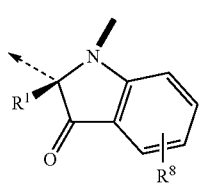 A14
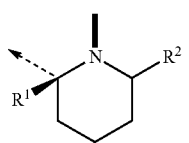 A15
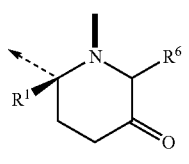 A16
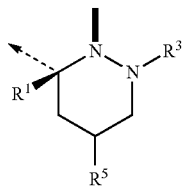 A17
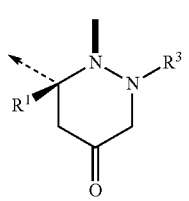 A18
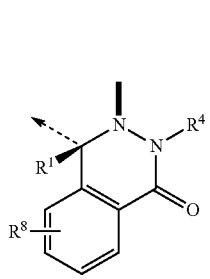 A19
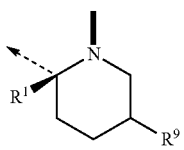 A20
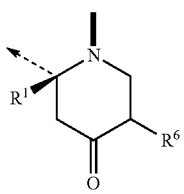 A21
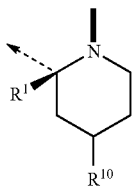 A22
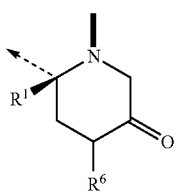 A23
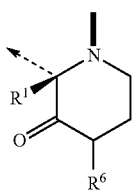 A24
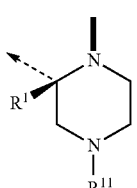 A25
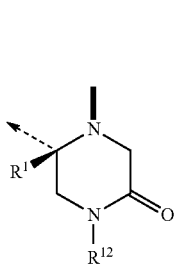 A26
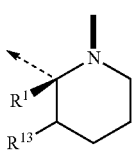 A27

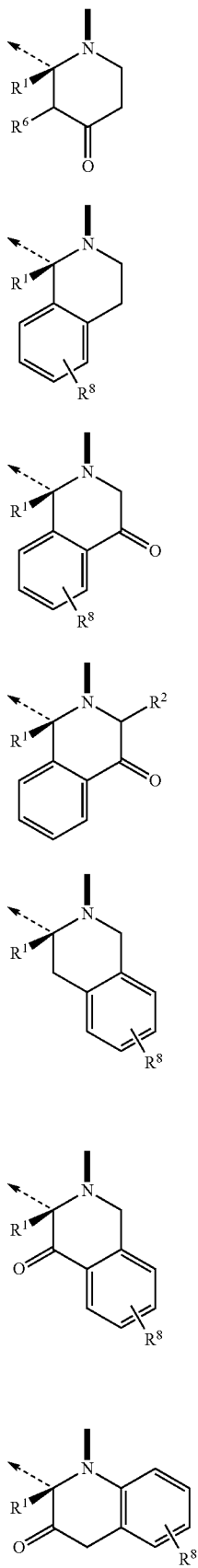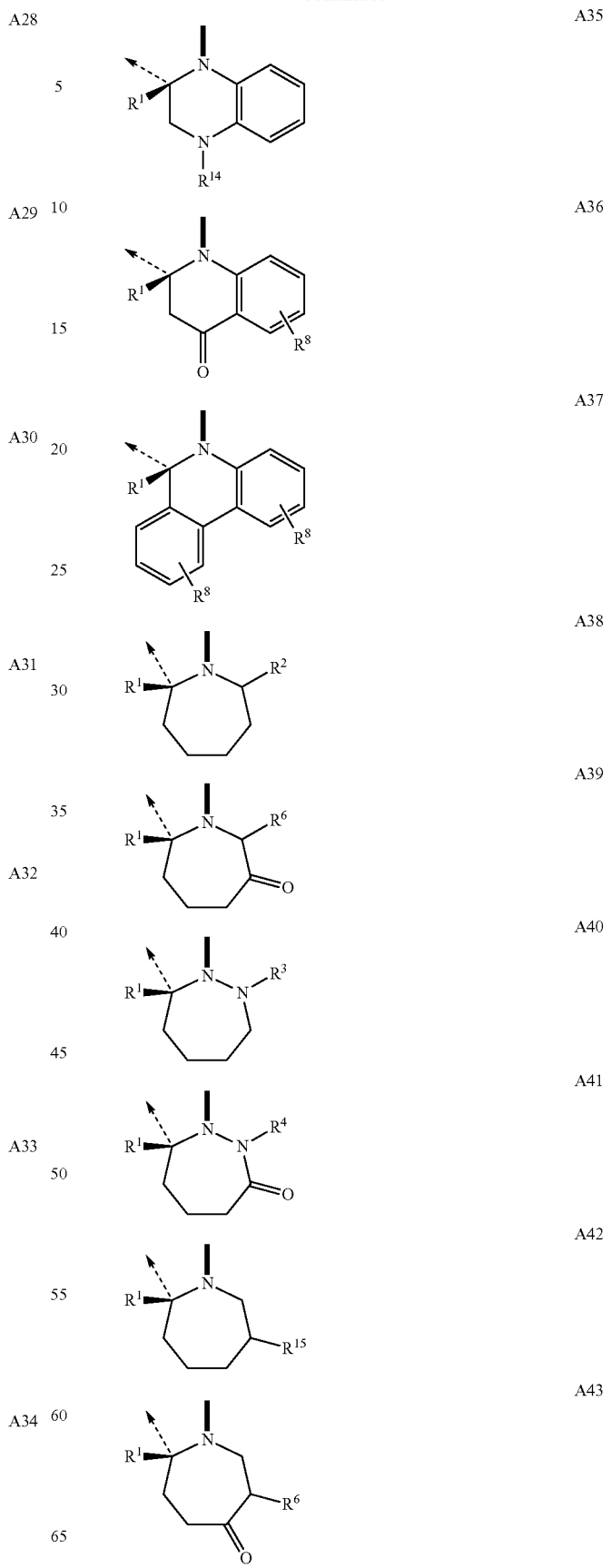

-continued
| | |
|---|---|
| 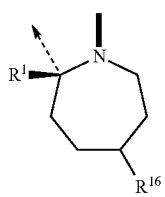 A44 | 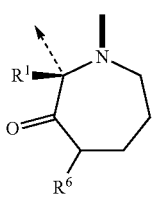 A52 |
| 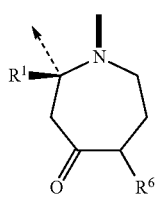 A45 | 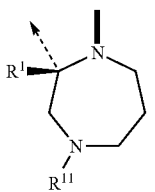 A53 |
| 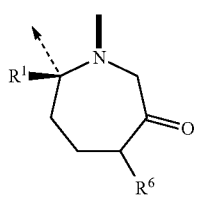 A46 | 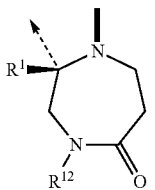 A54 |
| 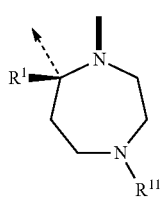 A47 | 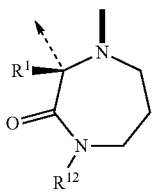 A55 |
| 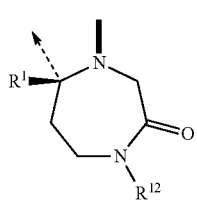 A48 | 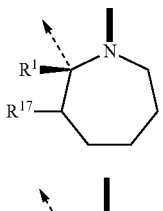 A56 |
| 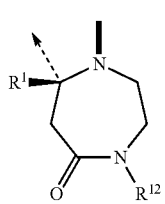 A49 | 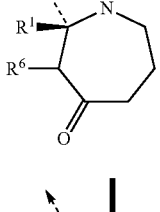 A57 |
| 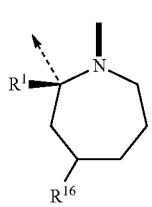 A50 | 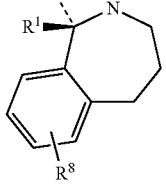 A58 |
| 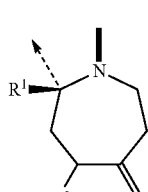 A51 | 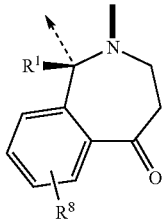 A59 |

A60 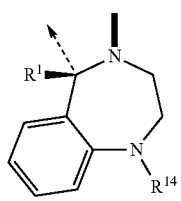
A61 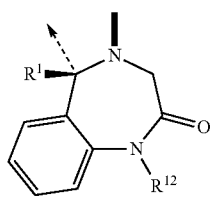
A62 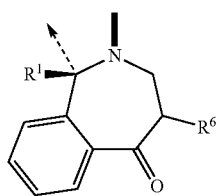
A63 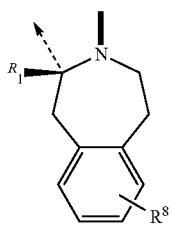
A64 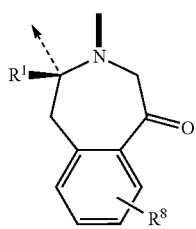
A65 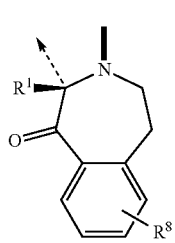
A66 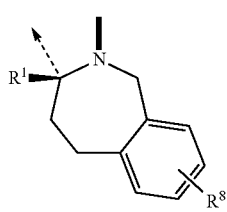
A67 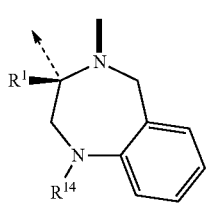
A68 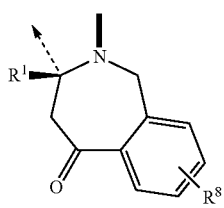
A69 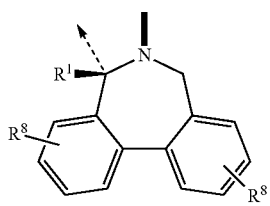
A70 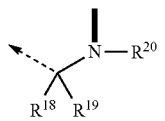
A71 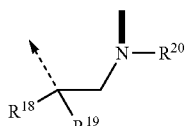
A72 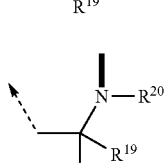
A73 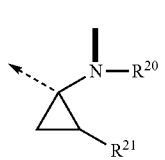
A74 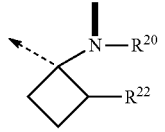
A75 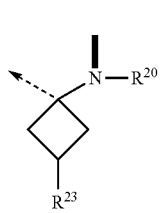

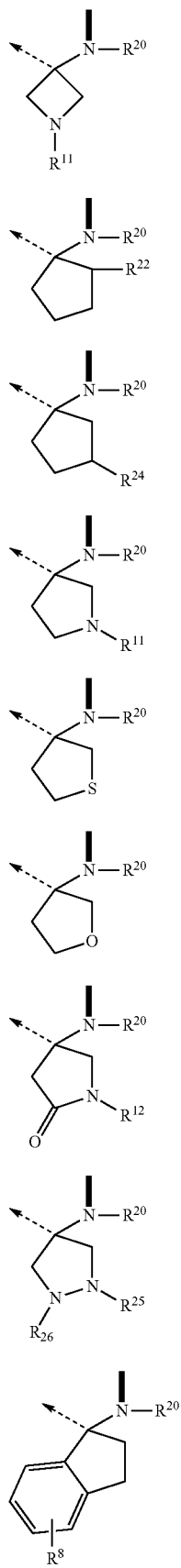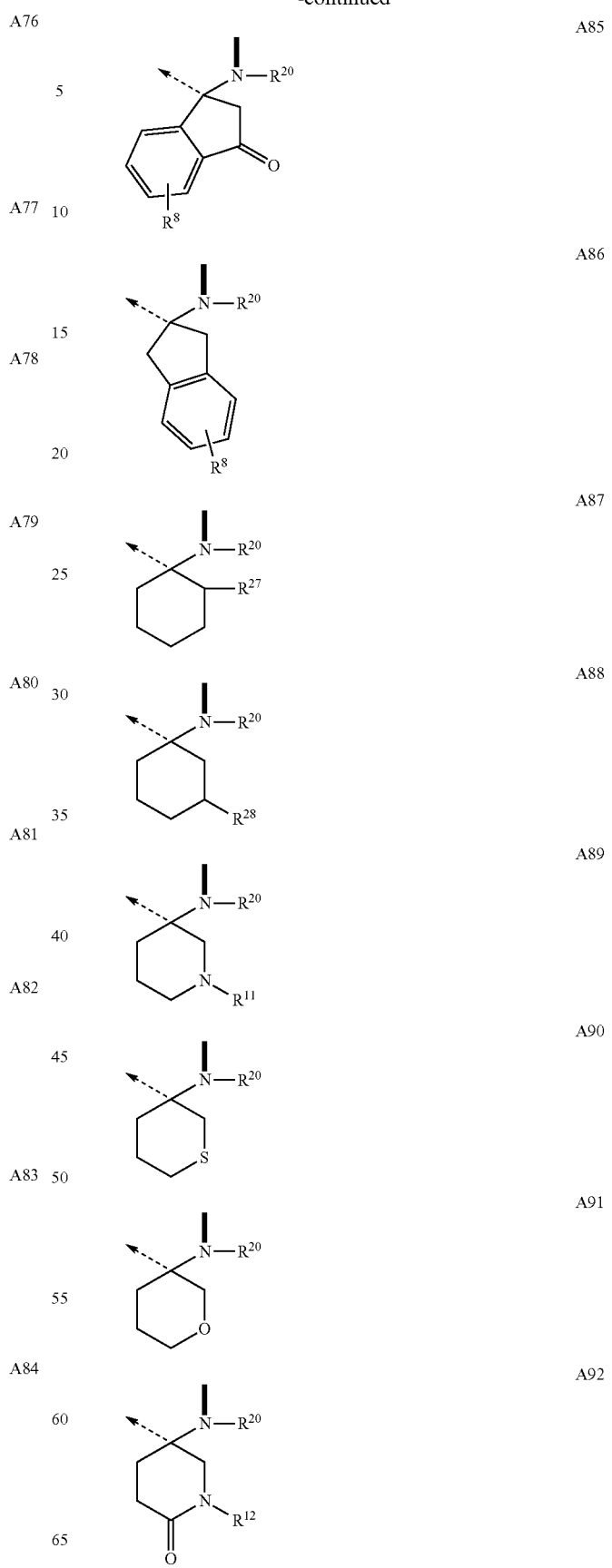

-continued
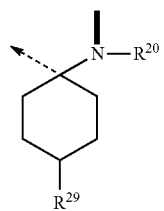
A93
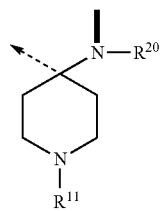
A94
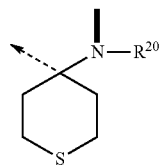
A95
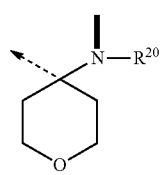
A96
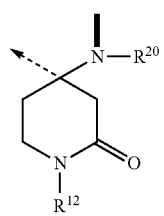
A97
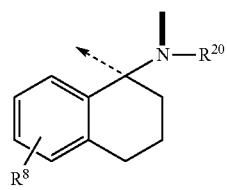
A98
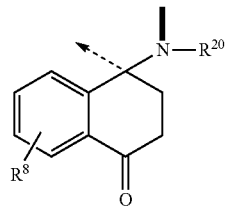
A99
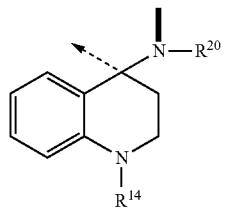
A100
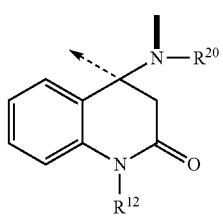
A101
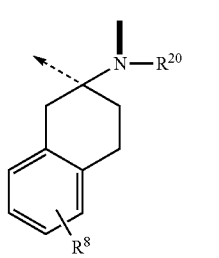
A102
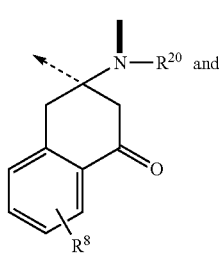
and
A103
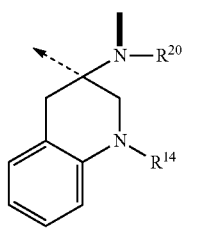
A104
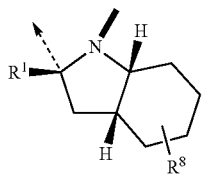
A105
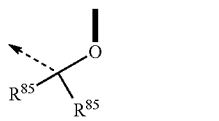
A106
A107
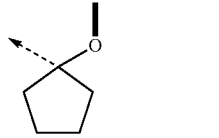
A108

-continued

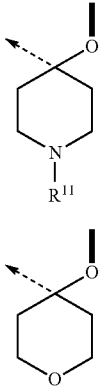

A109

A110

R$^1$ is H; lower alkyl; or aryl-lower alkyl;

R$^2$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$R$^{77}$;

R$^3$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{76}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^4$ is H; alkyl; alkenyl; —(CH$_2$)$_m$(CHR$^{61}$)$_s$OR$^{65}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_p$(CHR$^{61}$)$_s$COOR$^{57}$; —(CH$_2$)$_p$(CHR$^{61}$)$_s$CONR$^{58}$R$^{59}$; —(CH$_2$)$_p$(CHR$^{61}$)$_s$PO(OR$^{60}$)$_2$; —(CH$_2$)$_p$(CHR$^{61}$)$_s$SO$_2$R$^{62}$; or —(CH$_2$)$_o$(CHR$^{61}$)$_s$C$_6$H$_4$R$^8$;

R$^5$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^6$ is H; alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^7$ is alkyl; alkenyl; —(CH$_2$)$_q$(CHR$^{61}$)$_s$OR$^{55}$; —(CH$_2$)$_q$(CHR$^{61}$)$_s$NR$^{33}$R$^{34}$; —(CH$_2$)$_q$(CHR$^{61}$)$_s$OCONR$^{33}$R$^{75}$; —(CH$_2$)$_q$(CHR$^{61}$)$_s$NR$^{20}$CONR$^{33}$R$^{82}$; —(CH$_2$)$_r$(CHR$^{61}$)$_s$COOR$^{57}$; —(CH$_2$)$_r$(CHR$^{61}$)$_s$CONR$^{58}$R$^{59}$; —(CH$_2$)$_r$(CHR$^{61}$)$_s$PO(OR$^{60}$)$_2$; —(CH$_2$)$_r$(CHR$^{61}$)$_s$SO$_2$R$^{62}$; or —(CH$_2$)$_r$(CHR$^{61}$)$_s$C$_6$H$_4$R$^8$;

R$^8$ is H; Cl; F; CF$_3$; NO$_2$; lower alkyl; lower alkenyl; aryl; aryl-lower alkyl; —(CH$_2$)$_o$(CHR$^{61}$)$_s$R$^{77}$—(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$COR$^{64}$;

R$^9$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{10}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{11}$ is H; alkyl; alkenyl; —(CH$_2$)$_m$(CHR$^{61}$)$_s$OR$^{55}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{12}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_r$(CHR$^{61}$)$_s$COOR$^{57}$; —(CH$_2$)$_r$(CHR$^{61}$)$_s$CONR$^{58}$R$^{59}$; —(CH$_2$)$_r$(CHR$^{61}$)$_s$PO(OR$^{60}$)$_2$; —(CH$_2$)$_r$(CHR$^{61}$)$_s$SO$_2$R$^{62}$; or —(CH$_2$)$_r$(CHR$^{61}$)$_s$C$_6$H$_4$R$^8$;

R$^{13}$ is alkyl; alkenyl; —(CH$_2$)$_q$(CHR$^{61}$)$_s$OR$^{55}$; —(CH$_2$)$_q$(CHR$^{61}$)$_s$SR$^{56}$; —(CH$_2$)$_q$(CHR$^{61}$)$_s$NR$^{33}$R$^{34}$; —(CH$_2$)$_q$(CHR$^{61}$)$_s$OCONR$^{33}$R$^{75}$; —(CH$_2$)$_q$(CHR$^{61}$)$_s$NR$^{20}$CONR$^{33}$R$^{82}$; —(CH$_2$)$_q$(CHR$^{61}$)$_s$COOR$^{57}$; —(CH$_2$)$_q$(CHR$^{61}$)$_s$CONR$^{58}$R$^{59}$; —(CH$_2$)$_q$(CHR$^{61}$)$_s$PO(OR$^{60}$)$_2$; —(CH$_2$)$_q$(CHR$^{61}$)$_s$SO$_2$R$^{62}$; or —(CH$_2$)$_q$(CHR$^{61}$)$_s$C$_6$H$_4$R$^8$;

R$^{14}$ is H; alkyl; alkenyl; —(CH$_2$)$_m$(CHR$^{61}$)$_s$OR$^{55}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_q$(CHR$^{61}$)$_s$COOR$^{57}$; —(CH$_2$)$_q$(CHR$^{61}$)$_s$CONR$^{58}$R$^{59}$; —(CH$_2$)$_q$(CHR$^{61}$)$_s$PO(OR$^{60}$); —(CH$_2$)$_q$(CHR$^{61}$)$_s$SOR$^{62}$; or —(CH$_2$)$_q$(CHR$^{61}$)$_s$C$_6$H$_4$R$^5$;

R$^{15}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{16}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{17}$ is alkyl; alkenyl; —(CH$_2$)$_q$(CHR$^{61}$)$_s$OR$^{55}$; —(CH$_2$)$_q$(CHR$^{61}$)$_s$SR$^{56}$; —(CH$_2$)$_q$(CHR$^{61}$)$_s$NR$^{33}$R$^{34}$; —(CH$_2$)$_q$(CHR$^{61}$)$_s$OCONR$^{33}$R$^{75}$; —(CH$_2$)$_q$(CHR$^{61}$)$_s$NR$^{20}$CONR$^{33}$R$^{82}$; —(CH$_2$)$_q$(CHR$^{61}$)$_s$COOR$^{57}$; —(CH$_2$)$_q$(CHR$^{61}$)$_s$CONR$^{58}$R$^{59}$; —(CH$_2$)$_q$(CHR$^{61}$)$_s$PO(OR$^{60}$)$_2$; —(CH$_2$)$_q$(CHR$^{61}$)$_s$SO$_2$R$^{62}$; or —(CH$_2$)$_q$(CHR$^{61}$)$_s$C$_6$H$_4$R$^8$;

R$^{18}$ is alkyl; alkenyl; —(CH$_2$)$_p$(CHR$^{61}$)$_s$OR$^{55}$; —(CH$_2$)$_p$(CHR$^{61}$)$_s$SR$^{56}$; —(CH$_2$)$_p$(CHR$^{61}$)$_s$NR$^{33}$R$^{34}$; —(CH$_2$)$_p$(CHR$_{61}$)$_s$OCONR$^{33}$R$^{75}$; —(CH$_2$)$_p$(CHR$^{61}$)$_s$NR$^{20}$CONR$^{33}$R$^{82}$; —(CH$_2$)$_p$(CHR$^{61}$)$_s$COOR$^{57}$;

—$(CH_2)_p(CHR^{61})_sCONR^{58}R^{59}$; —$(CH_2)_p(CHR^{61})_sPO(OR^{60})_2$; —$(CH_2)_p(CHR^{61})_sSO_2R^{62}$; or —$(CH_2)_o(CHR^{61})_sC_6H_4R^8$;

$R^{19}$ is lower alkyl; —$(CH_2)_p(CHR^{61})_sOR^{55}$; —$(CH_2)_p(CHR^{61})_sSR^{56}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_p(CHR^{61})_sCOOR^{57}$; —$(CH_2)_p(CHR^{61})_sCONR^{58}R^{59}$; —$(CH_2)_p(CHR^{61})_sPO(OR^{60})_2$; —$(CH_2)_p(CHR^{61})_sSO_2R^{62}$; or —$(CH_2)_o(CHR^{61})_sC_6H_4R^8$; or $R^{18}$ and $R^{19}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{20}$ is H; alkyl; alkenyl; or aryl-lower alkyl;

$R^{21}$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{22}$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{23}$ is alkyl; alkenyl; —$(CH_2)_o(CHR^{61})_sR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^5$;

$R^{24}$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{25}$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{26}$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$; or $R^{25}$ and $R^{26}$ taken together can form: —$(CH_2)_{2-6}$—; —$(CH_2)_rO(CH_2)_r$—; —$(CH_2)_rS(CH_2)_r$—; or —$(CH_2)_rNR^{57}(CH_2)_r$—;

$R^{27}$ is H; alkyl; alkenyl; —$(CH_2)_o(CHR^{61})_sOR^{55}$; —$(CH_2)_o(CHR^{61})_sSR^{58}$; —$(CH_2)_o(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sOCONR^{33}R^{78}$; —$(CH_2)_o(CHR^{61})_sNR^{20}CONR^{33}R^{82}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{28}$ is alkyl; alkenyl; —$(CH_2)_o(CHR^{61})_s$—$OR^{55}$; —$(CH_2)_o(CHR^{61})_sSR^{56}$; —$(CH_2)_o(CHR^{61})_sNR^{33}R^{34}$;

—$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{29}$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{30}$ is H; alkyl; alkenyl; or aryl-lower alkyl;

$R^{31}$ is H; alkyl; alkenyl; —$(CH_2)_p(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; $(CH_2)_o(CHR^{61})_sCOOR^{57}$; —$(CH_2)_o(CHR^{61})_sCONR^{58}R^{59}$; $(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{32}$ is H; lower alkyl; or aryl-lower alkyl;

$R^{33}$ is H; alkyl, alkenyl; —$(CH_2)_m(CHR^{61})_sOR^{55}$; —$(CH_2)_m(CHR^{61})_sNR^{34}R^{63}$; —$(CH_2)_m(CHR^{61})_sOCONR^{75}R^{82}$; —$(CH_2)_m(CHR^{61})_sNR^{20}CONR^{78}R^{82}$; —$(CH_2)_m(CHR^{61})_sCOR^{64}$; —$(CH_2)_o(CHR^{61})_s$—$CONR^{58}R^{58}$, —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{34}$ is H; lower alkyl; aryl, or aryl-lower alkyl; or $R^{33}$ and $R^{34}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{35}$ is H; alkyl; alkenyl; —$(CH_2)_m(CHR^{61})_sOR^{55}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_p(CHR^{61})_sCOOR^{57}$; —$(CH_2)_p(CHR^{61})_sCONR^{58}R^{59}$; —$(CH_2)_p(CHR^{61})_sPO(OR^{60})_2$; —$(CH_2)_p(CHR^{61})_sSO_2R^{62}$; or —$(CH_2)_p(CHR^{61})_sC_6H_4R^8$;

$R^{36}$ is H, alkyl; alkenyl; —$(CH_2)_o(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_p(CHR^{61})_sCOOR^{57}$; —$(CH_2)_p(CHR^{61})_sCONR^{58}R^{59}$; —$(CH^2)_p(CHR^{61})_sPO(OR^{60})_2$; —$(CH_2)_p(CHR^{61})_sSO_2R^{62}$; or —$(CH_2)_o(CHR^{61})_sC_6H_4R^8$;

$R^{37}$ is H; F; Br; Cl; $NO_2$; $CF_3$; lower alkyl; —$(CH_2)_p(CHR^{61})_sOR^{65}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{38}$ is H; F; Br; Cl; $NO_2$; $CF_3$; alkyl; alkenyl; —$(CH_2)_p(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{69}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{39}$ is H; alkyl; alkenyl; or aryl-lower alkyl;

$R^{40}$ is H; alkyl; alkenyl; or aryl-lower alkyl;

$R^{41}$ is H; F; Br; Cl; $NO_2$; $CF_3$; alkyl; alkenyl; —$(CH_2)_p(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{42}$ is H; F; Br; Cl; $NO_2$; $CF_3$; alkyl; alkenyl; —$(CH_2)_p(CHR^{61})_sOR^{55}$; —$(CH_2)_p(CHR^{61})_sNR^{33}R^{34}$; —$(CH_2)_p$ $(CHR^{61})_sOCONR^{33}R^{75}$; $-(CH_2)_p(CHR^{61})_s$ $NR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; $-(CH_2)_o(CHR^{61})_sC_6H_4R^8$;

$R^{43}$ is H; alkyl; alkenyl; $-(CH_2)_m(CHR^{61})_sOR^{55}$; $-(CH_2)_m(CHR^{61})_sNR^{33}R^{34}$; $-(CH_2)_m(CHR^{61})_sOCONR^{33}R^{75}$; $-(CH_2)_m(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_pPO(OR^{60})_2$; $-(CH_2)_o(CHR^{61})_sSO_2R^{62}$; or $-(CH_2)_o(CHR^{61})_sC_6H_4R^8$;

$R^{44}$ is alkyl; alkenyl; $-(CH_2)_r(CHR^{61})_sOR^{55}$; $-(CH_2)_r(CHR^{61})_sSR^{56}$; $-(CH_2)_r(CHR^{61})_sNR^{33}R^{34}$; $-(CH_2)_r(CHR^{61})_sOCONR^{33}R^{75}$; $-(CH_2)_r(CHR^{61})_sNR^{20}CONR^{33}R^{82}$; $-(CH_2)_r(CHR^{61})_sCOOR^{57}$; $-(CH_2)_r(CHR^{61})_sCONR^{58}R^{59}$; $-(CH_2)_r(CHR^{61})_sPO(OR^{60})_2$; $-(CH_2)_r(CHR^{61})_sSO_2R^{62}$; or $-(CH_2)_r(CHR^{61})_sC_6H_4R^8$;

$R^{45}$ is H; alkyl; alkenyl; $-(CH_2)_o(CHR^{61})_sOR^{55}$; $-(CH_2)_o(CHR^{61})_sSR^{56}$; $-(CH_2)_o(CHR^{61})_sNR^{33}R^{34}$; $-(CH_2)_o(CHR^{61})_sOCONR^{33}R^{75}$; $-(CH_2)_o(CHR^{61})_sNR^{20}CONR^{33}R^{82}$; $-(CH_2)_o(CHR^{61})_sCOOR^{57}$; $-(CH_2)_s(CHR^{61})_sCONR^{58}R^{59}$; $-(CH_2)_s(CHR^{61})_sPO(OR^{60})_2$; $-(CH_2)_s(CHR^{61})_sSO_2R^{62}$; or $-(CH_2)_s(CHR^{61})_sC_6H_4R^8$;

$R^{46}$ is H; alkyl; alkenyl; or $-(CH_2)_o(CHR^{61})_pC_6H_4R^8$;

$R^{47}$ is H; alkyl; alkenyl; or $-(CH_2)_o(CHR^{61})_sOR^{55}$;

$R^{48}$ is H; lower alkyl; lower alkenyl; or aryl-lower alkyl;

$R^{49}$ is H; alkyl; alkenyl; $-(CHR^{61})_sCOOR^{57}$; $(CHR^{61})_sCONR^{58}R^{59}$; $-(CHR^{61})_sPO(OR^{60})_2$; $-(CHR^{61})_sSOR^{62}$; or $-(CHR^{61})_sC_6H_4R^8$;

$R^{50}$ is H; lower alkyl; or aryl-lower alkyl;

$R^{51}$ is H; alkyl; alkenyl; $-(CH_2)_m(CHR^{61})_sOR^{55}$; $-(CH_2)_m(CHR^{61})_sSR^{56}$; $-(CH_2)_m(CHR^{61})_sNR^{33}R^{34}$; $-(CH_2)_m(CHR^{61})_sOCONR^{33}R^{75}$; $-(CH_2)_m(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_pPO(OR^{60})_2$; $-(CH_2)_p(CHR^{61})_sSO_2R^{62}$; or $-(CH_2)_p(CHR^{61})_sC_6H_4R^8$;

$R^{52}$ is H; alkyl; alkenyl; $-(CH_2)_m(CHR^{61})_sOR^{55}$; $-(CH_2)_m(CHR^{61})_sSR^{56}$; $-(CH_2)_m(CHR^{61})_sNR^{33}R^{34}$; $-(CH_2)_m(CHR^{61})_sOCONR^{33}R^{75}$; $-(CH_2)_m(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_p(CHR^{61})_sSO_2R^{62}$; or $-(CH_2)_p(CHR^{61})_sC_6H_4R^8$;

$R^{53}$ is H; alkyl; alkenyl; $-(CH_2)_m(CHR^{61})_sOR^{55}$; $-(CH_2)_m(CHR^{61})_sSR^{56}$; $-(CH_2)_m(CHR^{61})_sNR^{33}R^{34}$; $-(CH_2)_m(CHR^{61})_sOCONR^{33}R^{75}$; $-(CH_2)_m(CHR^{61})_sNR^{28}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_pPO(OR^{60})_2$; $-(CH_2)_p(CHR^{61})_sSO_2R^{62}$; or $-(CH_2)_p(CHR^{61})_sC_6H_4R^8$;

$R^{54}$ is H; alkyl; alkenyl; $-(CH_2)_m(CHR^{61})_sOR^{55}$; $-(CH_2)_m(CHR^{61})_sNR^{33}R^{34}$; $-(CH_2)_o(CHR^{61})_sOCONR^{33}R^{75}$; $-(CH_2)_m(CHR^{61})_sNR^{20}CONR^{33}R^{82}$; $-(CH_2)_o(CHR^{61})COOR^{57}$; $-(CH_2)_o(CHR^{61})_sCONR^{58}R^{59}$; or $-(CH_2)_o(CHR^{61})_sC_6H_4R^8$;

$R^{55}$ is H; lower alkyl; lower alkenyl; aryl-lower alkyl; $-(CH_2)_m(CHR^{61})_sOR^{57}$; $-(CH_2)_o(CHR^{61})_sNR^{34}R^{63}$; $-(CH_2)_m(CHR^{61})_sOCONR^{75}R^{82}$; $-(CH_2)_m(CHR^{61})_sNR^{20}NR^{78}R^{82}$; $-(CH_2)_o(CHR^{61})_sCOR^{64}$; $-(CH_2)_o(CHR^{61})_sCOOR^{57}$; or $-(CH_2)_o(CHR^{61})_sCONR^{58}R^{59}$;

$R^{56}$ is H; lower alkyl; lower alkenyl; aryl-lower alkyl; $-(CH_2)_m(CHR^{61})_sOR^{57}$; $-(CH_2)_m(CHR^{61})_sNR^{34}R^{63}$; $-(CH_2)_m(CHR^{61})_sOCONR^{75}R^{82}$; $-(CH_2)_m(CHR^{61})_sNR^{20}CONR^{79}R^{82}$; $-(CH_2)_o(CHR^{61})_sCOR^{64}$; or $-(CH_2)_o(CHR^{61})_sCONR^{58}R^{59}$;

$R^{57}$ is H; lower alkyl; lower alkenyl; aryl lower alkyl; or heteroaryl lower alkyl;

$R^{58}$ is H; lower alkyl; lower alkenyl; aryl; heteroaryl; aryl-lower alkyl; or heteroaryl-lower alkyl;

$R^{59}$ is H; lower alkyl; lower alkenyl; aryl; heteroaryl; aryl-lower alkyl; or heteroaryl-lower alkyl; or $R^{58}$ and $R^{59}$ taken together can form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$;

$R^{60}$ is H; lower alkyl; lower alkenyl; aryl; or aryl-lower alkyl;

$R^{61}$ is alkyl; alkenyl; aryl; heteroaryl; aryl-lower alkyl; heteroaryl-lower alkyl; $-(CH_2)_pOR^{55}$; $-(CH_2)_pNR^{33}R^{34}$; $-(CH_2)_pOCONR^{75}R^{82}$; $-(CH_2)_pNR^{20}CONR^{79}R^{82}$; $-(CH_2)_oCOOR^{37}$; $-(CH_2)_oPO(OR^{60})_2$;

$R^{62}$ is lower alkyl; lower alkenyl; aryl, heteroaryl; or aryl-lower alkyl;

$R^{63}$ is H; lower alkyl; lower alkenyl; aryl, heteroaryl; aryl-lower alkyl; heteroaryl-lower alkyl; $-COR^{64}$; $-COOR^{57}$; $-CONR^{55}R^{59}$; $-SO_2R^{62}$; or $-PO(OR^{69})_2$; or $R^{34}$ and $R^{63}$ taken together can form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$;

$R^{64}$ is H; lower alkyl; lower alkenyl; aryl; heteroaryl; aryl-lower alkyl; heteroaryl-lower alkyl; $-(CH_2)_p(CHR^{61})_sOR^{65}$; $-(CH_2)_p(CHR^{61})_sSR^{66}$; $-(CH_2)_p(CHR^{61})_sNR^{34}R^{63}$; $-(CH_2)_p(CHR^{61})_sOCONR^{75}R^{82}$; or $-(CH_2)_P(CHR^{61})_sNR^{20}CONR^{78}R^{82}$;

$R^{65}$ is H; lower alkyl; lower alkenyl; aryl, aryl-lower alkyl; heteroaryl-lower alkyl; $-COR^{57}$; $-COOR^{57}$; or $-CONR^{58}R^{59}$;

$R^{66}$ is H; lower alkyl; lower alkenyl; aryl; aryl-lower alkyl; heteroaryl-lower alkyl; or $-CONR^{58}R^{59}$;

$R^{67}$ is H; Cl; Br; F; $NO_2$; $-NR^{34}COR^{57}$; $-CF_3$; CN; $-OCF_3$; $-OCHF_2$; $-OR^{57}$; $-SR^{62}$; lower alkyl; or lower alkenyl;

$R^{68}$ is H; Cl; Br; F; $NO_2$; $-NR^{34}COR^{57}$; $-CF_3$; CN; $-OCF_3$; $-OCHF_2$; $-OR^{57}$; $-SR^{62}$; lower alkyl; or lower alkenyl;

$R^{69}$ is H; Cl; Br; F; $NO_2$; $-NR^{34}COR^{57}$; $-CF_3$; CN; $-OCF_3$; $-OCHF_2$; $-OR^{57}$; $-SR^{62}$; lower alkyl; or lower alkenyl;

$R^{70}$ is H; Cl; Br; F; $NO_2$; $-NR^{34}COR^{57}$; $-CF_3$; CN; $-OCF_3$; $-OCHF_2$; $-OR^{57}$; $-SR^{62}$; lower alkyl; or lower alkenyl;

$R^{71}$ is lower alkyl; lower alkenyl; $-(CH_2)_p(CHR^{61})_sOR^{75}$; $-(CH_2)_p(CHR^{61})_sSR^{75}$; $-(CH_2)_p(CHR^{61})_sNR^{33}R^{34}$; $-(CH_2)_p(CHR^{61})_sOCONR^{33}R^{75}$; $-(CH_2)_p(CHR^{61})_sNR^{20}CONR^{33}R^{82}$; $-(CH_2)_o(CHR^{61})_sCOOR^{75}$; $-(CH_2)_pCONR^{58}R^{59}$; $-(CH_2)_pPO(OR^{62})_2$; $-(CH_2)_pSO_2R^{62}$; or $-(CH_2)_o-C_6R^{67}R^{68}R^{69}R^{70}R^{76}$;

$R^{72}$ is alkyl; alkenyl; $-(CH_2)_p(CHR^{61})_sOR^{85}$; or $-(CH_2)_p(CHR^{61})_sSR^{85}$;

$R^{73}$ is $-(CH_2)_rR^{77}$; $-(CH_2)_rS(CH_2)_oR^{77}$; $-(CH_2)_rS(CH_2)_oR^{77}$; or $-(CH_2)_rNR^{20}(CH_2)_oR^{77}$;

$R^{74}$ is $-(CH_2)_pNR^{78}R^{79}$; $-(CH_2)_pNR^{77}R^{80}$; $-(CH_2)_pC(=NR^{80})NR^{78}R^{79}$; $-(CH_2)_pC(=NOR^{50})NR^{78}R^{79}$; $-(CH_2)_pC(=NNR^{78}R^{79})NR^{78}R^{79}$; $-(CH_2)_pNR^{80}C(=NR^{80})NR^{78}R^{79}$; $-(CH_2)_pN=C(NR^{78}R^{80})NR^{79}R^{80}$; $-(CH_2)_pC_6H_4NR^{78}R^{79}$; $-(CH_2)_pC_6H_4NR^{77}R^{80}$; $-(CH_2)_pC_6H_4C(=NR^{80})NR^{78}R^{79}$; $-(CH_2)_pC_6H_4C(=NOR^{50})NR^{78}R^{79}$; $-(CH_2)_pC_6H_4C(=NNR^{78}R^{79})NR^{78}R^{79}$; $-(CH_2)_pC_6H_4NR^{80}C$ $(=NR^{80})NR^{78}R^{79}$; $-(CH_2)_rC_6H_4C(=NR^{78}R^{80})NR^{79}R^{80}$; $-(CH_2)_rO(CH_2)_mNH^{78}H^{79}$; $-(CH_2)_rO(CH_2)_mNR^{77}R^{80}$; $-(CH_2)_rO(CH_2)_pC(=NR^{80})NR^{78}R^{79}$; $-(CH_2)_rO(CH_2)_pC(=NOR^{50})NR^{78}R^{79}$; $-(CH_2)_rO(CH_2)_pC(=NNR^{78}R^{79})NR^{78}R^{79}$; $-(CH_2)_rO(CH_2)_mNR^{80}C(=NR^{80})NR^{78}R^{79}$; $-(CH_2)_rO(CH_2)_mN=C(NR^{78}R^{80})NR^{79}R^{80}$; $-(CH_2)_rO(CH_2)_pC_6H_4CNR^{78}R^{79}$; $-(CH_2)_rO(CH_2)_pC_6H_4C(=NR^{80})NR^{78}R^{79}$; $-(CH_2)_rO(CH_2)_pC_6H_4C(=NOR^{50})NR^{78}R^{79}$; $-(CH_2)_rO(CH_2)_pC_6H_4C(=NNR^{78}R^{79})NR^{78}R^{79}$; $-(CH_2)_rO(CH_2)_pC_6H_4NR^{80}C(=NR^{80})NR^{78}R^{79}$; $-(CH_2)_rS(CH_2)_mNR^{78}R^{79}$; $-(CH_2)_rS(CH_2)_mNR^{77}R^{80}$; $-(CH_2)_rS(CH_2)_pC(=NR^{80})NR^{78}R^{79}$; $-(CH_2)_rS(CH_2)_pC(=NOR^{50})NR^{78}R^{79}$; $-(CH_2)_rS(CH_2)_pC(=NNR^{78}R^{79})NR^{78}R^{79}$; $-(CH_2)_rS(CH_2)_mNR^{80}C(=NR^{80})NR^{78}R^{79}$; $-(CH_2)_rS(CH_2)_mN=C(NR^{78}R^{80})NR^{78}R^{80}$; $-(CH_2)_rS(CH_2)_pC_6H_4CNR^{78}R^{79}$; $-(CH_2)_rS(CH_2)_pC_6H_4C(=NR^{80})NR^{78}R^{79}$; $-(CH_2)_rS(CH_2)_pC_6H_4C(=NOR^{50})NR^{78}R^{79}$; $-(CH_2)_rS(CH_2)_pC_6H_4C(=NNR^{78}R^{79})NR^{78}R^{79}$; $-(CH_2)_rS(CH_2)_pC_6H_4NR^{80}C(=NR^{80})NR^{78}R^{79}$; $-(CH_2)_pNR^{80}COR^{64}$; $-(CH_2)_pNR^{80}COR^{77}$; $-(CH_2)_pNR^{80}CONR^{78}R^{79}$; or $-(CH_2)_pC_6H_4NR^{80}CONR^{78}R^{79}$;

$R^{75}$ is lower alkyl; lower alkenyl; or aryl-lower alkyl; or $R^{33}$ and $R^{75}$ taken together can form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; or $R^{75}$ and $R^{82}$ taken together can form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$;

$R^{76}$ is H; lower alkyl; lower alkenyl; aryl-lower alkyl; $-(CH_2)_oOR^{72}$; $-(CH_2)_oSR^{72}$; $-(CH_2)_oNR^{33}R^{34}$; $-(CH_2)_oOCONR^{33}R^{75}$; $-(CH_2)_oNR^{20}CONR^{33}R^{81}$; $-(CH_2)_oCOOR^{75}$; $-(CH_2)_oCONR^{58}R^{59}$; $-(CH_2)_oPO(OR^{60})_2$; $-(CH_2)_pSO_2R^{62}$; or $-(CH_2)_oCOR^{64}$;

$R^{77}$ is $-C_6R^{67}R^{68}R^{69}R^{70}R^{76}$ with the proviso that at least two of $R^{67}$, $R^{68}$, $R^{69}$ and $R^{70}$ are H; or a heteroaryl group of one of the formulae

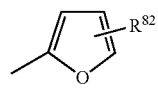 H1

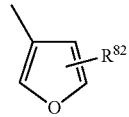 H2

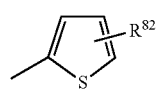 H3

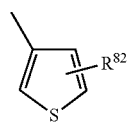 H4

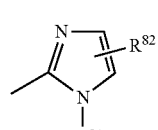 H5

-continued

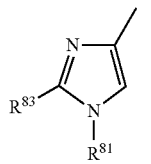 H6

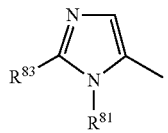 H7

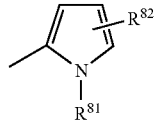 H8

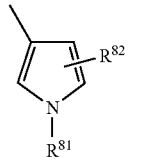 H9

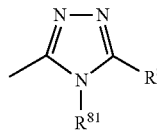 H10

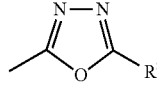 H11

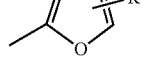 H12

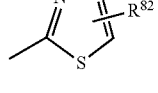 H13

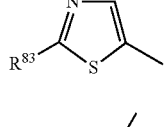 H14

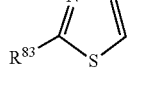 H15

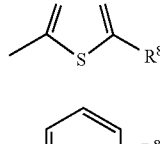 H16

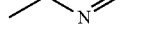 H17

US 8,883,720 B2

-continued

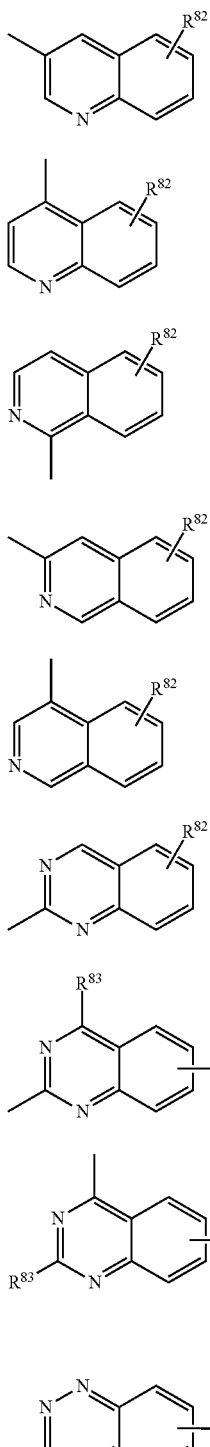

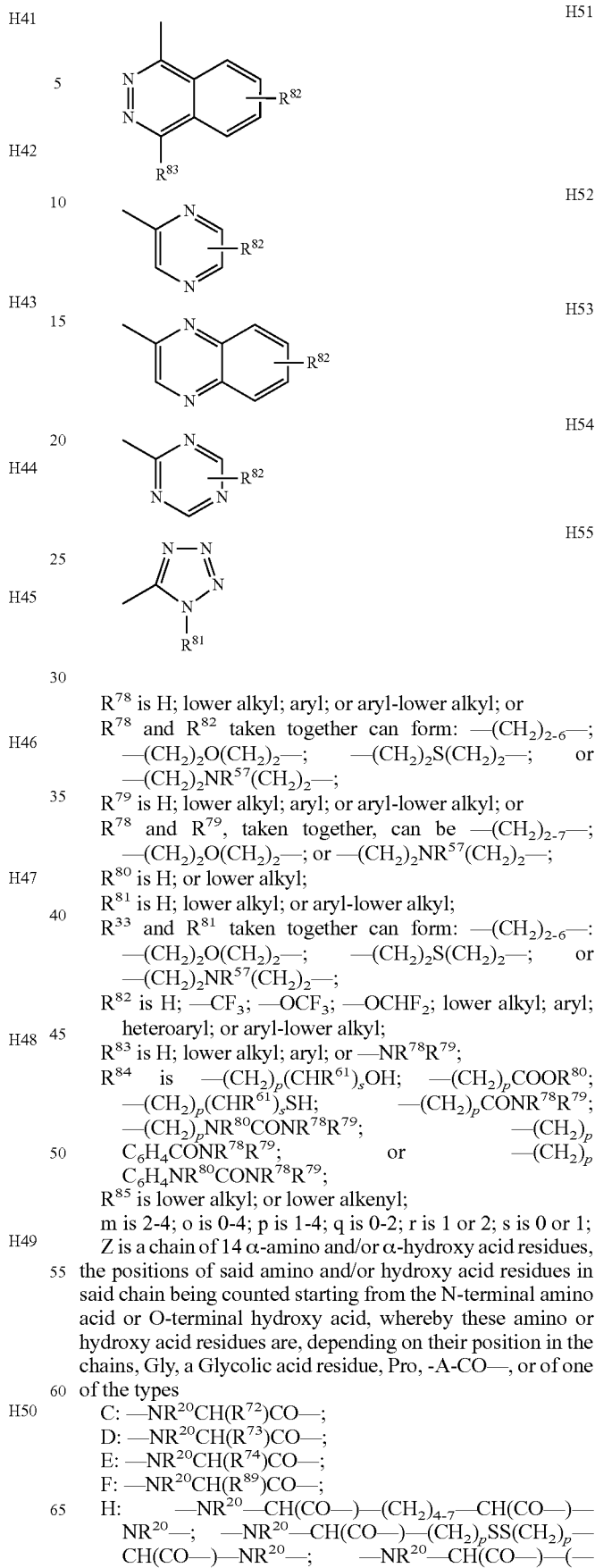

R$^{78}$ is H; lower alkyl; aryl; or aryl-lower alkyl; or
R$^{78}$ and R$^{82}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;
R$^{79}$ is H; lower alkyl; aryl; or aryl-lower alkyl; or
R$^{78}$ and R$^{79}$, taken together, can be —(CH$_2$)$_{2-7}$—; —(CH$_2$)$_2$O(CH$_2$)$_2$—; or —(CH$_2$)$_2$NR$^{57}$(CH$_2$)$_2$—;
R$^{80}$ is H; or lower alkyl;
R$^{81}$ is H; lower alkyl; or aryl-lower alkyl;
R$^{33}$ and R$^{81}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;
R$^{82}$ is H; —CF$_3$; —OCF$_3$; —OCHF$_2$; lower alkyl; aryl; heteroaryl; or aryl-lower alkyl;
R$^{83}$ is H; lower alkyl; aryl; or —NR$^{78}$R$^{79}$;
R$^{84}$ is —(CH$_2$)$_p$(CHR$^{61}$)$_s$OH; —(CH$_2$)$_p$COOR$^{80}$; —(CH$_2$)$_p$(CHR$^{61}$)$_s$SH; —(CH$_2$)$_p$CONR$^{78}$R$^{79}$; —(CH$_2$)$_p$NR$^{80}$CONR$^{78}$R$^{79}$; —(CH$_2$)$_p$C$_6$H$_4$CONR$^{78}$R$^{79}$; or —(CH$_2$)$_p$C$_6$H$_4$NR$^{80}$CONR$^{78}$R$^{79}$;
R$^{85}$ is lower alkyl; or lower alkenyl;
m is 2-4; o is 0-4; p is 1-4; q is 0-2; r is 1 or 2; s is 0 or 1;
Z is a chain of 14 α-amino and/or α-hydroxy acid residues, the positions of said amino and/or hydroxy acid residues in said chain being counted starting from the N-terminal amino acid or O-terminal hydroxy acid, whereby these amino or hydroxy acid residues are, depending on their position in the chains, Gly, a Glycolic acid residue, Pro, -A-CO—, or of one of the types
C: —NR$^{20}$CH(R$^{72}$)CO—;
D: —NR$^{20}$CH(R$^{73}$)CO—;
E: —NR$^{20}$CH(R$^{74}$)CO—;
F: —NR$^{20}$CH(R$^{89}$)CO—;
H: —NR$^{20}$—CH(CO—)—(CH$_2$)$_{4-7}$—CH(CO—)—NR$^{20}$—; —NR$^{20}$—CH(CO—)—(CH$_2$)$_p$SS(CH$_2$)$_p$—CH(CO—)—NR$^{20}$—; —NR$^{20}$—CH(CO—)—(—

$(CH_2)_p NR^{20}CO(CH_2)_p$—CH(CO—)—$NR^{20}$—; or
—$NR^{20}$—CH(CO—)—(—$(CH_2)_p NR^{20}CONR^{20}$
$(CH_2)_p$—CH(CO—)—$NR^{20}$—; and L: —O—CH($R^{71}$)CO—; —O—CH($R^{72}$)CO—;
—O—CH($R^{73}$)CO—; —O—CH($R^{74}$)CO—; or
—OCH($R^{84}$)CO—;

with the proviso that in said chain Z of 14 α-amino and/or α-hydroxy acid residues the amino or hydroxy acid residues in positions 1 to 14 are:

P1: of type C, type D, type F or of type L;

P2: of type D, type E, type F, or of type L;

P3: of type C, type D, type E, type F, type L, or Gly, or a Glycolic acid residue;

P4: of type C, type D, type E or of type F;

P5: of type E, type F or of type L;

P6: of type C, type L, Gly or a Glycolic acid residue;

P7: of formula -A-CO—, Pro, Gly or a Glycolic acid residue;

P8: of formula A-CO—, type C, type D, type E, type F or of type L;

P9: of type D or type E;

P10: of type C or type D;

P11: of type C, type D or type F;

P12: of type D, type F or of type L;

P13: of type C, type D, type E, type F or of type L; and

P14: of type C, type E, type F or of type L; or

P4 and P11, taken together, can form a group of type H;

at P5, P7 and P13 also D-isomers being possible;

and with the further proviso that the molecule contains at least one but not more than 3 α-hydroxy acid residues; and pharmaceutically acceptable salts thereof.

In accordance with the present invention these β-hairpin peptidomimetics can be prepared by a process which comprises (a) coupling an appropriately functionalized solid support with an appropriately N-protected derivative of that amino acid or an appropriately O-protected derivative of that hydroxy acid which in the desired end-product is in positions 3, 5, 6, 7, 8 or 10, any functional group which may be present in said N-protected amino acid derivative or O-protected hydroxy acid derivative being likewise appropriately protected;

(b) removing the N-protecting or O-protecting group from the product thus obtained;

(c) coupling the product thus obtained with an appropriately N-protected derivative of that amino acid or an appropriately O-protected derivative of that hydroxy acid which in the desired end-product is one position nearer the N-terminal amino acid residue or O-terminal hydroxy acid residue, any functional group which may be present in said N-protected amino acid derivative or O-protected hydroxy acid derivative being likewise appropriately protected;

(d) removing the N-protecting group or O-protecting group from the product thus obtained;

(e) repeating steps (c) and (d) until the N-terminal amino acid residue or O-terminal hydroxy acid residue has been introduced;

(f) coupling the product thus obtained with one of the compounds of the general formulae

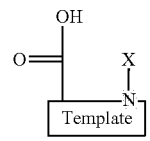

IIa

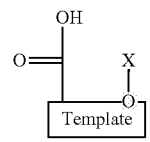

IIb wherein

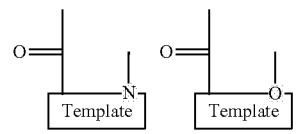

is as defined above and X is an N-protecting group and, respectively, an O-protecting group; or, alternatively, if

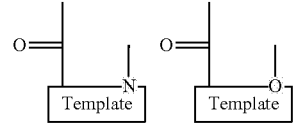

is to be group (a1) or (a2) above, (fa) coupling the product obtained in step (e) with an appropriately N-protected derivative of an amino acid or an appropriately O-protected derivative of a hydroxy acid of the general formula

HOOC—B—H          III or

HOOC-A-H          IV wherein B and A are as defined above, any functional group which may be present in said N-protected amino acid derivative or O-protected hydroxy acid derivative being likewise appropriately protected;

(fb) removing the N-protecting group or O-protecting group from the product thus obtained; and (fc) coupling the product thus obtained with an appropriately N-protected derivative of an amino acid or an appropriately O-protected derivative of a hydroxy acid of the above general formula IV and, respectively, III, any functional group which may be present in said N-protected amino acid derivative or O-protected hydroxy acid derivative being likewise appropriately protected;

(g) removing the N-protecting group or O-protecting group from the product obtained in step (f) or (fc);

(h) coupling the product thus obtained with an appropriately N-protected derivative of that amino acid or an appropriately O-protected derivative of that hydroxy acid which in the desired end-product is in position 14, any functional group which may be present in said N-protected amino acid derivative or O-protected hydroxy acid derivative being likewise appropriately protected;

(i) removing the N-protecting group or O-protecting group from the product thus obtained;

(j) coupling the product thus obtained with an appropriately N-protected derivative of that amino acid or an appropriately O-protected derivative of that hydroxy acid which in the desired end-product is one position farther away from position 14, any functional group which may be present in said N-protected amino acid derivative or O-protected hydroxy acid derivative being likewise appropriately protected;

(k) removing the N-protecting group or O-protecting group from the product thus obtained;

(l) repeating steps (j) and (k) until all amino acid or hydroxy acid residues have been introduced;

(m) if desired, selectively deprotecting one or several protected functional group(s) present in the molecule and appropriately substituting the reactive group(s) thus liberated;

(n) if desired, forming an interstrand linkage between sidechains of appropriate amino acid residues at positions P4 and P11;

(o) detaching the product thus obtained from the solid support;

(p) cyclizing the product cleaved from the solid support;

(q) removing any protecting groups present on functional groups of any members of the chain of amino acid and/or hydroxy acid residues and, if desired, any protecting group(s) which may in addition be present in the molecule; and (r) if desired, converting the product thus obtained into a pharmaceutically acceptable salt or converting a pharmaceutically acceptable, or unacceptable, salt thus obtained into the corresponding free compound of formula Ia or Ib or into a different, pharmaceutically acceptable, salt.

Alternatively, the peptidomimetics of the present invention can be prepared by (a') coupling an appropriately functionalized solid support with one of the compounds of the general formulae

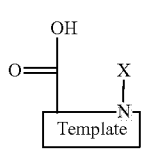

IIa

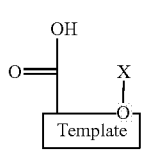

IIb wherein

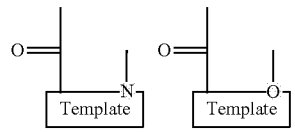

is as defined above and X is an N-protecting group or an O-protecting group, or, alternatively, if

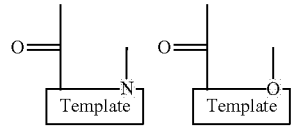

is to be group (a1) or (a2) above, (a'a) coupling said appropriately functionalized solid support with an appropriately N-protected derivative of an amino acid or an appropriately O-protected derivative of a hydroxy acid of the general formula

HOOC—B—H    III or

HOOC-A-H    IV wherein B and A are as defined above, any functional group which may be present in said N-protected amino acid derivative or O-protected hydroxy acid derivative being likewise appropriately protected;

(a'b) removing the N-protecting group or O-protecting group from the product thus obtained; and (a'c) coupling the product thus obtained with an appropriately N-protected derivative of an amino acid or an appropriately O-protected derivative of a hydroxy acid of the above general formula IV and, respectively, III, any functional group which may be present in said N-protected amino acid derivative or O-protected hydroxy acid derivative being likewise appropriately protected;

(b') removing the N-protecting group or O-protecting group from the product obtained in step (a') or (a'c)

(c') coupling the product thus obtained with an appropriately N-protected derivative of that amino acid or an appropriately O-protected derivative of that hydroxy acid which in the desired end-product is in position 14, any functional group which may be present in said N-protected amino acid derivative or O-protected hydroxy acid derivative being likewise appropriately protected;

(d') removing the N-protecting group or O-protecting group from the product thus obtained;

(e') coupling the product thus obtained with an appropriately N-protected derivative of that amino acid or an appropriately O-protected derivative of that hydroxy acid which in the desired end-product is one position farther away from position 14, any functional group which may be present in said N-protected amino acid derivative or O-protected hydroxy acid derivative being likewise appropriately protected;

(f') removing the N-protecting group or O-protecting group from the product thus obtained;

(g') repeating steps (e') and (f') until all amino acid or hydroxy acid residues have been introduced;

(h') if desired, selectively deprotecting one or several protected functional group(s) present in the molecule and appropriately substituting the reactive group(s) thus liberated;
(i') if desired forming an interstrand linkage between side-chains of appropriate amino acid residues at positions P4 and P11;
(j') detaching the product thus obtained from the solid support;
(k') cyclizing the product cleaved from the solid support;
(l') removing any protecting groups present on functional groups of any members of the chain of amino acid and/or hydroxy acid residues and, if desired, any protecting group(s) which may in addition be present in the molecule; and
(m') if desired, converting the product thus obtained into a pharmaceutically acceptable salt or converting a pharmaceutically acceptable, or unacceptable, salt thus obtained into the corresponding free compound of formula Ia or Ib or into a different, pharmaceutically acceptable, salt.

According to a further alternative, peptidomimetics of the present invention wherein

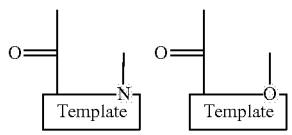

is to be group (a1) or (a2) above, can be prepared by
(a"a) coupling an appropriately functionalized solid support with an appropriately N-protected derivative of an amino acid or an appropriately O-protected derivative of a hydroxy acid of the general formula

HOOC-A-H            IV or

HOOC—B—H            III wherein A and B are as defined above, any functional group which may be present in said N-protected amino acid derivative or O-protected hydroxy acid derivative being likewise appropriately protected;
(a"b) removing the N-protecting group or O-protecting group from the product thus obtained;
(b") coupling the product thus obtained with an appropriately N-protected derivative of that amino acid or an appropriately O-protected derivative of that hydroxy acid which in the desired end-product is in position 14, any functional group which may be present in said N-protected amino acid derivative or O-protected hydroxy acid derivative being likewise appropriately protected;
(c") removing the N-protecting group or O-protecting group from the product thus obtained;
(d") coupling the product thus obtained with an appropriately N-protected derivative of that amino acid or an appropriately O-protected derivative of that hydroxy acid which in the desired end-product is one position farther away from position 14, any functional group which may be present in said N-protected amino acid derivative or O-protected hydroxy acid derivative being likewise appropriately protected;
(e") removing the N-protecting group or O-protecting group from the product thus obtained;
(f") repeating steps (d") and (e") until all amino acid or hydroxy acid residues of the chain Z have been introduced;
(g") coupling the product thus obtained with an appropriately N-protected derivative of an amino acid or an appropriately O-protected derivative of a hydroxy acid of the above general formula III and, respectively, IV, any functional group which may be present in said N-protected amino acid derivative or O-protected hydroxy acid derivative being likewise appropriately protected;
(h") removing the N-protecting group or O-protecting group from the product obtained in step ((g")
(i") if desired, selectively deprotecting one or several protected functional group(s) present in the molecule and appropriately substituting the reactive group(s) thus liberated;
(j") if desired forming an interstrand linkage between side-chains of appropriate amino acid residues at positions P4 and P11;
(k") detaching the product thus obtained from the solid support;
(l") cyclizing the product cleaved from the solid support;
(m") removing any protecting groups present on functional groups of any members of the chain of amino acid and/or hydroxy acid residues and, if desired, any protecting group(s) which may in addition be present in the molecule; and
(n") if desired, converting the product thus obtained into a pharmaceutically acceptable salt or converting a pharmaceutically acceptable, or unacceptable, salt thus obtained into the corresponding free compound of formula Ia or Ib or into a different, pharmaceutically acceptable, salt.

The peptidomimetics of the present invention can also be enantiomers of the compounds of formula Ia or Ib. These enantiomers can be prepared by a modification of the above processes in which enantiomers of all chiral starting materials are used.

As used in this description, the term "alkyl", taken alone or in combinations, designates saturated, straight-chain or branched hydrocarbon radicals having up to 24, preferably up to 12, carbon atoms. Similarly, the term "alkenyl" designates straight chain or branched hydrocarbon radicals having up to 24, preferably up to 12, carbon atoms and containing at least one or, depending on the chain length, up to four olefinic double bonds. The term "lower" designates radicals and compounds having up to 6 carbon atoms. Thus, for example, the term "lower alkyl" designates saturated, straight-chain, or branched hydrocarbon radicals having up to 6 carbon atoms, such as methyl, ethyl, n-propyl, isopropyl, n-butyl, sec.-butyl, isobutyl, tert.-butyl, and the like. Similarly, the term "lower cycloalkyl" designates saturated cyclic hydrocarbon radicals having up to 6 carbon atoms, such as cyclopentyl, cyclohexyl and the like. The term "aryl" designates aromatic carbocyclic hydrocarbon radicals containing one or two six-membered rings, such as phenyl or naphthyl, which may be substituted by up to three substituents such as Br, Cl, F, $CF_3$, $NO_2$, lower alkyl or lower alkenyl. The term "heteroaryl" designates aromatic heterocyclic radicals containing one or two five- and/or six-membered rings, at least one of them containing up to three heteroatoms selected from the group consisting of O, S and N and said ring(s) being optionally substituted; representative examples of such optionally substituted heteroaryl radicals are indicated hereinabove in connection with the definition of $R^{77}$.

The structural element -A-CO— designates amino acid building blocks which in combination with the structural element —B—CO— form templates (a1) and (a2). Templates (a) through (p) constitute building blocks which have an N- or O-terminus and a C-terminus oriented in space in such a way that the distance between those two groups may lie between 4.0-5.5 A. A peptide or depsipeptide chain Z is linked to the C-terminus and the N- or O-terminus of the templates (a) through (p) via the corresponding N- or O- and C-termini so that the template and the chain form a cyclic structure such as that depicted in formulae Ia or Ib. In a case as here where the distance between the N- or O- and C-termini of the template lies between 4.0-5.5 A the template will induce the H-bond network necessary for the formation of a β-hairpin conformation in the peptide or depsipeptide chain Z. Thus template and peptide or depsipeptide chain form a β-hairpin mimetic.

The β-hairpin conformation is highly relevant for the CXCR4 antagonizing activity of the β-hairpin mimetics of the present invention. The β-hairpin stabilizing conformational properties of the templates (a) through (p) play a key role not only for the selective antagonizing activity but also for the synthesis process defined hereinabove, as incorporation of the templates (a) through (p) or part of the templates (a) at the beginning or near the middle of the linear protected peptide or depsipeptide precursors enhances cyclization yields significantly.

Building blocks A1-A69 and A105 belong to a class of amino acids wherein the N-terminus is a secondary amine forming part of a ring. Among the genetically encoded amino acids only proline falls into this class. The configuration of building block A1 through A69 and A105 is (D), and they are combined with a building block —B—CO— of (L)-configuration. Preferred combinations for templates (a1) are $-^{D}A1$-CO—$^{L}B$—CO— to $-^{D}A69$-CO—$^{L}B$—CO— and $-^{D}A105$-CO—$^{L}B$—CO—. Thus, for example, $^{D}Pro$-$^{L}Pro$ constitutes the prototype of templates (a1). Less preferred, but possible are combinations —$^{L}B$—CO-$^{D}A1$-CO— to $^{D}A69$-CO— and $-^{D}A105$-CO—$^{L}B$—CO-forming templates (a2). Thus, for example, $^{L}Pro$-$^{D}Pro$ constitutes the prototype of template (a2).

It will be appreciated that building blocks -A1-CO— to -A69-CO— and A105-CO— in which A has (D)-configuration, are carrying a group $R^1$ at the β-position to the N-terminus. The preferred values for $R^1$ are H and lower alkyl with the most preferred values for $R^1$ being H and methyl. It will be recognized by those skilled in the art, that A1-A69 and A105 are shown in (D)-configuration which, for $R^1$ being H and methyl, corresponds to the (R)-configuration. Depending on the priority of other values for $R^1$ according to the Cahn, Ingold and Prelog rules, this configuration may also have to be expressed as (S).

In addition to $R^1$ building blocks -A1-CO— to -A69-CO— and A105-CO— can carry an additional substituent designated as $R^2$ to $R^{17}$. This additional substituent can be H, and if it is other than H, it is preferably a small to medium-sized aliphatic or aromatic group. Examples of preferred values for $R^2$ to $R^{17}$ are:

$R^2$: H; lower alkyl; lower alkenyl; $-(CH_2)_mOR^{55}$ (where $R^{55}$: lower alkyl; or lower alkenyl); $-(CH_2)_mSR^{56}$ (where $R^{56}$: lower alkyl; or lower alkenyl); $-(CH_2)_mNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$); $-(CH_2)_2O(CH_2)-$; $-(CH_2)_2S(CH_2)_2-$; or $-(CH_2)_2NR^{57}(CH_2)_2-$; where $R^{57}$: H; or lower alkyl); $-(CH_2)_mNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: H; lower alkyl; or lower alkenyl); $-(CH_2)_oSO_2R^{62}$ (where $R^{62}$: lower alkyl; or lower alkenyl); $-(CH_2)_qC_6H_4R^8$ (where $R^3$: H; F; Cl; $CF_3$; lower alkyl; lower alkenyl; or lower alkoxy); or $-(CH_2)_qCHN_4R^8$.

$R^3$: H; lower alkyl; lower alkenyl; $-(CH_2)_mOR^{55}$ (where $R^{55}$: lower alkyl; or lower alkenyl); $-(CH_2)_mSR^{56}$ (where $R^{56}$: lower alkyl; or lower alkenyl); $-(CH_2)_mNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_pPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^4$: H; lower alkyl; lower alkenyl; $-(CH_2)_mOR^{55}$ (where $R^{55}$: lower alkyl; or lower alkenyl); $-(CH_2)_mSR^{56}$ (where $R^{56}$: lower alkyl; or lower alkenyl); $-(CH_2)_mNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_qCOOR^{57}$ (where $R^{57}$: lower alkyl; or lower alkenyl); —$(CH_2)_qCONR^{58}R^{59}$ (where $R^{56}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^5$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: alkyl; alkenyl; aryl; and aryl-lower alkyl, heteroaryl-lower alkyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^6$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}K^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{55}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{66})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^5$ (where $R^8$: H; F; Cl; $CF_3$; lower alkyl; lower alkenyl; or lower alkoxy).

$R^7$: lower alkyl; lower alkenyl; —$(CH_2)_qOR^{55}$ (where $R^{55}$: lower alkyl; or lower alkenyl); —$(CH_2)_qSR^{56}$ (where $R^{56}$ lower alkyl; or lower alkenyl); —$(CH_2)_qNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qN(R^{20})COR^{64}$ (where: $R^{20}$: H; or lower alkyl; $R^{64}$: lower alkyl; or lower alkenyl); —$(CH_2)_rCOOR^{57}$ (where $R^{57}$: lower alkyl; or lower alkenyl); —$(CH_2)_qCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_rPO(OR^{60})_2$ (where $R^{60}$: lower alkyl; or lower alkenyl); —$(CH_2)_rSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^8$: H; F; Cl; $CF_3$; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^9$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{39}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{69}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{10}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_2PO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{11}$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S$ $(CH_2)_2$—; or —$(CH_2)_2NR^{57}(CH_2)_2$—; where $R^{57}$: H; or lower alkyl); —$(CH_2)_mNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{66})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{12}$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{26}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_rCOOR^{57}$ (where $R^{57}$: lower alkyl; or lower alkenyl); —$(CH_2)_rCONR^{58}R^{59}$ (where $R^{56}$: lower alkyl; or lower alkenyl; and $R^{59}$: H; or lower alkyl; or $R^{58}$ and $R^{59}$ taken together form: —$(CH_2)_{2-6}$—: —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_rPO(OP^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_oC_6H_4R^8$ (where $R^8$: H; F; Cl; $CF_3$; lower alkyl; lower alkenyl; or lower alkoxy).

$R^{13}$: lower alkyl; lower alkenyl; —$(CH_2)_qOR^{55}$ (where $R^{55}$: lower alkyl; or lower alkenyl); —$(CH_2)_qSR^{56}$ (where $R^{56}$: lower alkyl; or lower alkenyl); —$(CH_2)_qNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qN(R^{20})COR_{64}$ (where: $R^{20}$: H; or lower alkyl; $R^{64}$: lower alkyl; or lower alkenyl); —$(CH_2)_rCOO^{57}$ (where $R^{57}$: lower alkyl; or lower alkenyl); —(CH$_2$)$_q$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_r$PO(OR$^{60}$)$_2$ (where R$^{60}$: lower alkyl; or lower alkenyl); —(CH$_2$)$_r$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{14}$: H; lower alkyl; lower alkenyl; —(CH$_2$)$_m$OR$^{55}$ (where R$^{55}$: lower alkyl; or lower alkenyl); —(CH$_2$)$_m$SR$^{56}$ (where R$^{56}$: lower alkyl; or lower alkenyl); —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$NR$^{20}$CONR$^{33}$R$^{81}$ (where R$^{20}$: H; or lower lower alkyl; R$^{33}$: H; or lower alkyl; or lower alkenyl; R$^{81}$: H; or lower alkyl; or R$^{33}$ and R$^{81}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$N(R$^{20}$)COR$^{64}$ (where: R$^{20}$: H; lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); —(CH$_2$)$_q$C$_6$H$_4$R$^8$ (where R$^8$: H; F; Cl; CF$_3$; lower alkyl; lower alkenyl; or lower alkoxy).

R$^{15}$: lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$NR$^{20}$CONR$^{33}$R$^{81}$ (where R$^{20}$: H; or lower lower alkyl; R$^{33}$: H; or lower alkyl; or lower alkenyl; R$^{81}$: H; or lower alkyl; or R$^{33}$ and R$^{81}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R)$^{20}$COR$^{64}$ (where: R$^{20}$: H; or lower alkyl; R$^{64}$: lower alkyl; or lower alkenyl); particularly favoured being —NR$^{20}$CO-lower alkyl (R$^{20}$: H; or lower alkyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{16}$: lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$NR$^{20}$CONR$^{33}$R$^{81}$ (where R$^{20}$: H; or lower lower alkyl; R$^{33}$: H; or lower alkyl; or lower alkenyl; R$^{81}$: H; or lower alkyl; or R$^{33}$ and R$^{81}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); —(CH$_2$)$_o$COOR$^{67}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{17}$: lower alkyl; lower alkenyl; —(CH$_2$)$_q$OR$^{55}$ (where R$^{55}$: lower alkyl; or lower alkenyl); —(CH$_2$)$_m$SR$^{56}$ (where R$^{56}$: lower alkyl; or lower alkenyl); —(CH$_2$)$_q$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_q$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_q$NR$^{20}$CONR$^{33}$R$^{81}$ (where R$^{20}$: H; or lower lower alkyl; R$^{33}$: H; or lower alkyl; or lower alkenyl; R$^{81}$: H; or lower alkyl; or R$^{33}$ and R$^{81}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_q$N(R$^{20}$)COR$^{64}$ (where: R$^{20}$: H; or lower alkyl; R$^{64}$: lower alkyl; or lower alkenyl); —(CH$_2$)$_r$COOR$^{57}$ (where R$^{57}$: lower alkyl; or lower alkenyl); —(CH$_2$)$_q$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_r$PO(OR$^{60}$)$_2$ (where R$^{60}$: lower alkyl; or lower alkenyl); —(CH$_2$)$_r$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

Among the building blocks A1 to A69 and A105 the following are preferred: A5 with R$^2$ being H, A8, A22, A25, A38 with R$^2$ being H, A42, A47, A50 and A105. Most preferred are building blocks of type A8':

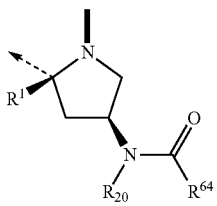

A8' wherein R[20] is H or lower alkyl; and R[64] is alkyl; alkenyl; aryl; aryl-lower alkyl; or heteroaryl-lower alkyl; especially those wherein R[64] is n-hexyl (A8'-1); n-heptyl (A8'-2); 4-(phenyl)benzyl (A8'-3); diphenylmethyl (A8'-4); 3-amino-propyl (A8'-5); 5-amino-pentyl (A8'-6); methyl (A8'-7); ethyl (A8'-8); isopropyl (A8'-9); isobutyl (A8'-10); n-propyl (A8'-11); cyclohexyl (A8'-12); cyclohexylmethyl (A8'-13); n-butyl (A8'-14); phenyl (A8'-15); benzyl (A8'-16); (3-indolyl)methyl (A8'-17); 2-(3-indolyl)ethyl (A8'-18); (4-phenyl)phenyl (A8'-19); and n-nonyl (A8'-20).

Building block A70 belongs to the class of open-chain α-substituted α-amino acids, building blocks A71 and A72 to the corresponding β-amino acid analogues and building blocks A73-A104 to the cyclic analogues of A70. Such amino acid derivatives have been shown to constrain small peptides in well defined reverse turn or U-shaped conformations (C. M. Venkatachalam, *Biopolymers* 1968, 6, 1425-1434; W. Kabsch, C. Sander, *Biopolymers* 1983, 22, 2577). Such building blocks or templates are ideally suited for the stabilization of β-hairpin conformations in peptide loops (D. Obrecht, M. Altorfer, J. A. Robinson, "Novel Peptide Mimetic Building Blocks and Strategies for Efficient Lead Finding", *Adv. Med. Chem.* 1999, Vol. 4, 1-68; P. Balaram, "Non-standard amino acids in peptide design and protein engineering", *Curr. Opin. Struct. Biol.* 1992, 2, 845-851; M. Crisma, G. Valle, C. Toniolo, S. Prasad, R. B. Rao, P. Balaram, "β-turn conformations in crystal structures of model peptides containing α,α-disubstituted amino acids", *Biopolymers* 1995, 35, 1-9; V. J. Hruby, F. Al-Obeidi, W. Kazmierski, *Biochem. J.* 1990, 268, 249-262).

It has been shown that both enantiomers of building blocks -A70-CO— to A104-CO— in combination with a building block —B—CO— being an α-amino acid with L-configuration can efficiently stabilize and induce β-hairpin conformations (D. Obrecht, M. Altorfer, J. A. Robinson, "Novel Peptide Mimetic Building Blocks and Strategies for Efficient Lead Finding", *Adv. Med. Chem.* 1999, Vol. 4, 1-68; D. Obrecht, C. Spiegler, P. Schönholzer, K. Müller, H. Heimgartner, F. Stierli, *Helv. Chim. Acta* 1992, 75, 1666-1696; D. Obrecht, U. Bohdal, J. Daly, C. Lehmann, P. Schönholzer, K. Müller, *Tetrahedron* 1995, 51, 10883-10900; D. Obrecht, C. Lehmann, C. Ruffieux, P. Schönholzer, K. Müller, *Helv. Chim. Acta* 1995, 78, 1567-1587; D. Obrecht, U. Bohdal, C. Broger, D. Bur, C. Lehmann, R. Ruffieux, P. Schönholzer, C. Spiegler, *Helv. Chim. Acta* 1995, 78, 563-580; D. Obrecht, H. Karajiannis, C. Lehmann, P. Schönholzer, C. Spiegler, *Helv. Chim. Acta* 1995, 78, 703-714).

Thus, for the purposes of the present invention templates (a1) and (a2) can also consist of -A70-CO— to A104-CO— or -A106-CO— to A110-CO— where building block A70 to A104 or A106 to A110 is of either (D)- or (L)-configuration, in combination with a building block —B—CO— of (L)-configuration.

Preferred values for $R^{20}$ in A70 to A104 are H or lower alkyl with methyl being most preferred. Preferred values for $R^{18}$, $R^{19}$ and $R^{21}$-$R^{29}$ in building blocks A70 to A104 are the following:

$R^{18}$: lower alkyl.

$R^{19}$: lower alkyl; lower alkenyl; —$(CH_2)_pOR^{55}$ (where $R^{55}$: lower alkyl; or lower alkenyl); —$(CH_2)_pSR^{56}$ (where $R^{56}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{26}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{69}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{69})_2$ (where $R^{60}$: lower alkyl; or lower alkenyl); —$(CH_2)_pSO_2R^{62}$ (where $R^{62}$: lower alkyl; or lower alkenyl); or —$(CH_2)_oO_6H_4R^8$ (where $R^8$: H; F; Cl; $CF_3$; lower alkyl; lower alkenyl; or lower alkoxy).

$R^{21}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o{}^oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{22}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl, or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; CF; lower alkyl; lower alkenyl; or lower alkoxy).

$R^{23}$: H; lower alkyl; lower alkenyl; $-(CH_2)_oOR^{55}$ (where $R^{55}$: lower alkyl; or lower alkenyl); $-(CH_2)_oSR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oN(R^{20})COR^{64}$ (where: $R^{20}$: H; or lower alkyl; $R^{64}$: lower alkyl; or lower alkenyl); particularly favoured are $NR^{20}CO$-lower alkyl ($R^{20}$: H; or lower alkyl); $-(CH_2)_oCOOR^{57}$ (where $R^{57}$: lower alkyl; or lower alkenyl); $-(CH_2)_oCONR^{58}R^{59}$ (where $R^{58}$: lower alkyl, or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^{24}$: lower alkyl; lower alkenyl; $-(CH_2)_oOR^{55}$ (where $R^{55}$: lower alkyl; or lower alkenyl); $-(CH_2)_oSR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oN(R^{20})COR^{64}$ (where: $R^{20}$: H; or lower alkyl; $R^{64}$: lower alkyl; or lower alkenyl); particularly favoured are $NR^{20}CO$-lower alkyl ($R^{20}$: H; or lower alkyl); $-(CH_2)_oCOOR^{57}$ (where $R^{57}$: lower alkyl; or lower alkenyl); $-(CH_2)_oCONR^{58}R^{59}$ (where $R^{58}$: lower alkyl, or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^{25}$: H; lower alkyl; lower alkenyl; $-(CH_2)_mOR^{55}$ (where $R^{55}$: lower alkyl; or lower alkenyl); $-(CH_2)_mNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mNR^{20}CONR^{33}R^{81}$ (where $R^{20}$H; or lower lower alkyl; $R^{33}$: H; or lower alkyl; or lower alkenyl; $R^{81}$: H; or lower alkyl; or $R^{33}$ and $R^{81}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^{26}$: H; lower alkyl; lower alkenyl; $-(CH_2)_mOR^{55}$ (where $R^{55}$: lower alkyl; or lower alkenyl); $-(CH_2)_mNR^{33}R^{34}$ (where: $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}$ $(CH_2)_2$—; where $R^{57}$: H; or lower alkyl); —$(CH_2)_o$PO$(OR^{60})_2$ (where $R^{60}$: lower alkyl; or lower alkenyl); —$(CH_2)_o$SO$_2R^{62}$ (where $R^{62}$: lower alkyl; or lower alkenyl); or —$(CH_2)_qC_6H_4R^8$ (where $R^8$: H; F; Cl; CF$_3$; lower alkyl; lower alkenyl; or lower alkoxy).

Alternatively, $R^{25}$ and $R^{26}$ taken together can be —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl).

$R^{27}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(OH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; CF$_3$; lower alkyl; lower alkenyl; or lower alkoxy).

$R^{28}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; CF$_3$; lower alkyl; lower alkenyl; or lower alkoxy).

$R^{29}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)$—; —$(CH_2)_2S(CH_2)$—; or —$(CH_2)_2NR^{57}(CH_2)$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); particularly favored are NR$^{20}$CO-lower-alkyl ($R^{20}$: H; or lower alkyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; CF$_3$; lower alkyl; lower alkenyl; or lower alkoxy).

For templates (b) to (p), such as (b1) and (c1), the preferred values for the various symbols are the following:

$R^8$: H; F; Cl; CF$_3$; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{81}$ (where $R^{20}$: H; or lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; CF$_3$; lower alkyl; lower alkenyl; or lower alkoxy).

$R^{20}$: H; or lower alkyl.

$R^{30}$: H; or methyl.

$R^{31}$: H; lower alkyl; lower alkenyl; —$(CH_2)_pOR^{55}$ (where $R^{55}$: lower alkyl; or lower alkenyl); —$(CH_2)_pNR^{23}R^{24}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{32}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{22}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); (—$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy); most preferred is —$CH_2CONR^{58}R^{59}$ ($R^{58}$: H; or lower alkyl; $R^{59}$: lower alkyl; or lower alkenyl).

$R^{32}$: H; or methyl.

$R^{33}$: lower alkyl; lower alkenyl; —$(CH_2)_mOR^{55}$ (where $R^{55}$: lower alkyl; or lower alkenyl); —$(CH_2)_mNR^{34}R^{63}$ (where $R^{34}$: lower alkyl; or lower alkenyl; $R^{63}$: H; or lower alkyl; or $R^{34}$ and $R^{63}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{75}R^{82}$ (where $R^{75}$: lower alkyl; or lower alkenyl; $R^{82}$: H; or lower alkyl; or $R^{75}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{78}R^{81}$ (where $R^{20}$: H; or lower lower alkyl; $R^{78}$: H; or lower alkyl; or lower alkenyl; $R^{81}$: H; or lower alkyl; or $R^{78}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl).

$R^{34}$: H; or lower alkyl.

$R^{35}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{81}$(where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl).

$R^{36}$: lower alkyl; lower alkenyl; or aryl-lower alkyl.

$R^{37}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{33}R^{81}$ (where $R^{20}$: H; or lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alky; or lower alkenyl); or —$(CH_2)_qC_6H_4R^8$ (where $R^8$: H; F; Cl; $CF_3$; lower alkyl; lower alkenyl; or lower alkoxy).

$R^{38}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{78}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}OCNR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{54}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{39}$: H; lower alkyl; lower alkenyl; —$(CH_2)_mOR^{55}$ (where $R^{55}$: lower alkyl; or lower alkenyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{56}$ and $R^{59}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl).

$R^{40}$: lower alkyl; lower alkenyl; or aryl-lower alkyl.

$R^{41}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alky; or $R^{58}$ and $R^{59}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{42}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{33}R^{81}$ (where $R^{20}$: H; m or lower lower alkyl; $R^{33}$: H; or lower alkyl; or lower alkenyl; $R^{81}$: H; or lower alkyl; or $R^{33}$ and $R^{81}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2\text{-}6}$: —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{43}$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{44}$: lower alkyl; lower alkenyl; —$(CH_2)_pOR^{55}$ (where $R^{55}$: lower alkyl; or lower alkenyl); —$(CH_2)_pSR^{56}$ (where $R^{56}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2\text{-}6}$—; —$(CH_2)_2O(CH_2)_2$—; $(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{78}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{29}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_qC_6H_4R^8$ (where $R^8$: H; F; Cl; $CF_3$; lower alkyl; lower alkenyl; or lower alkoxy).

$R^{45}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sOCONR^{33}R^{75}$ (where $R^{33}$: H; or lower alkyl; or lower alkenyl; $R^{75}$: lower alkyl; or $R^{33}$ and $R^{75}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$): H; or lower alkyl; $R^{41}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form:—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_sC_6H_4R^8$ (where $R^8$: H; F; Cl; $CF_3$; lower alkyl; lower alkenyl; or lower alkoxy).

$R^{46}$: H; lower alkyl; lower alkenyl; —$(CH_2)_sOR^{55}$ (where $R^{55}$: lower alkyl; or lower alkenyl); —$(CH_2)_sSR^{56}$ (where $R^{56}$: lower alkyl; or lower alkenyl); —$(CH_2)_sNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_sC_6H_4R^8$ (where $R^8$: H; F; Cl; $CF_3$; lower alkyl; lower alkenyl; or lower alkoxy).

$R^{47}$: H; or $OR^{55}$ (where $R^{55}$: lower alkyl; or lower alkenyl).

$R^{48}$: H; or lower alkyl.

$R^{49}$: H; lower alkyl; —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form:—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_sC_6H_4R^8$ (where $R^8$: H; F; Cl; $CF_3$; lower alkyl; lower alkenyl; or lower alkoxy).

$R^{50}$: H; or methyl.

$R^{51}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(OH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_rC_6H_4R^8$ (where $R^8$: H; F; Cl; $CF_3$; lower alkyl; lower alkenyl; or lower alkoxy).

$R^{52}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{39}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—;—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{26}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—;—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_rC_6H_4R^8$ (where $R^8$: H; F; Cl; $CF_3$; lower alkyl; lower alkenyl; or lower alkoxy).

$R^{53}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—;—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNO^{20}CONR^{33}R^{81}$ (where $R^{20}$: H; or lower lower alkyl; $R^{33}$: H; or lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—;—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_rC_6H_4R^8$ (where $R^8$: H; F; Cl; $CF_3$; lower alkyl; lower alkenyl; or lower alkoxy).

$R^{54}$: lower alkyl; lower alkenyl; or aryl-lower alkyl.

Among the building blocks A70 to A104 the following are preferred: A74 with $R^{22}$ being H, A75, A76, A77 with $R^{22}$ being H, A78 and A79.

The building block —B—CO— within templates (a1) and (a2) designates an L-amino or an L-hydroxy acid residue. Preferred values for B are: —$NR^{20}CH(R^{71})$—, enantiomers of groups A5 with $R^2$ being H, A8, A22, A25, A38 with $R^2$ being H, A42, A47, and A50, and —$OCH(R^{71})$—, —$OCH(R^{72})$—, —$OCH(R^{73})$—, —$OCH(R^{74})$— and —$OCH(R^{84})$—. Most preferred building blocks —B—CO— are

| | |
|---|---|
| Ala | L-Alanine |
| Arg | L-Arginine |
| Asn | L-Asparagine |
| Asp | L-Aspartic acid |
| Cys | L-Cysteine |
| Gln | L-Glutamine |
| Glu | L-Glutamic acid |
| Gly | Glycine |
| His | L-Histidine |
| Ile | L-Isoleucine |
| Leu | L-Leucine |
| Lys | L-Lysine |
| Met | L-Methionine |
| Phe | L-Phenylalanine |
| Pro | L-Proline |
| Ser | L-Serine |
| Thr | L-Threonine |
| Trp | L-Tryptophan |
| Tyr | L-Tyrosine |
| Val | L-Valine |
| Cit | L-Citrulline |
| Orn | L-Ornithine |
| tBuA | L-t-Butylalanine |
| Sar | Sarcosine |
| t-BuG | L-tert.-Butylglycine |
| 4AmPhe | L-para-Aminophenylalanine |
| 3AmPhe | L-meta-Aminophenylalanine |
| 2AmPhe | L-ortho-Aminophenylalanine |
| Phe(mC(NH$_2$)=NH) | L-meta-Amidinophenylalanine |
| Phe(pC(NH$_2$)=NH) | L-para-Amidinophenylalanine |
| Phe(mNHC(NH$_2$)=NH) | L-meta-Guanidinophenylalanine |
| Phe(pNHC(NH$_2$)=NH) | L-para-Guanidinophenylalanine |
| Phg | L-Phenylglycine |
| Cha | L-Cyclohexylalanine |
| C$_4$al | L-3-Cyclobutylalanine |
| C$_5$al | L-3-Cyclopentylalanine |
| Nle | L-Norleucine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl$_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Tic | L-1,2,3,4-Tetrahydroisoquinoline-3-carboxylic acid |
| Thi | L-β-2-Thienylalanine |
| Tza | L-2-Thiazolylalanine |
| Mso | L-Methionine sulfoxide |
| AcLys | L-N-Acetyllysine |
| Dpr | L-2,3-Diaminopropionic acid |
| A$_2$Bu | L-2,4-Diaminobutyric acid |
| Dab | (2S,3S)-2,3-Diaminobutyric acid |
| Abu | γ-Aminobutyric acid (GABA) |
| Aha | ε-Aminohexanoic acid |
| Aib | α-Aminoisobutyric acid |
| Y(Bzl) | L-O-Benzyltyrosine |
| Bip | L-Biphenylalanine |
| S(Bzl) | L-O-Benzylserine |
| T(Bzl) | L-O-Benzylthreonine |
| hCha | L-Homo-cyclohexylalanine |
| hCys | L-Homo-cysteine |
| hSer | L-Homo-serine |
| hArg | L-Homo-arginine |
| hPhe | L-Homo-phenylalanine |
| Bpa | L-4-Benzoylphenylalanine |
| Pip | L-Pipecolic acid |
| OctG | L-Octylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methvaline |
| MeLeu | L-N-Methylleucine |
| 4Hyp1 | (4S)-L-Hydroxyproline |
| 4Hyp2 | (4R)-L-Hydroxyproline |
| 4Mp1 | (4S)-L-Mercaptoproline |
| 4Mp2 | (4R)-L-Mercaptoproline |
| Oic | (3aS,7aS)-L-1-Octahydro-1H-indole-2-carboxylic acid |
| Glycolic acid | |
| Lac | (2S)-2-Hydroxy-propanoic acid |
| Hmb | (2S)-2-Hydroxy-3-methylbutyric acid |
| H3mp | (2S,3S)-2-Hydroxy-3-methyl-pentanoic acid |
| H4mp | (2S)-2-Hydroxy-4-methyl-pentanoic acid |
| Hmtb | (2S)-2-Hydroxy-4-methylthio butyric acid |
| Hhpp | (2S)-2-Hydroxy-3-(4'-hydroxyphenyl)-propionic acid |
| Himp | (2S)-2-Hydroxy-3-(Imidazole-4'-yl)-propionic-acid |
| Hpp | (2S)-2-Hydroxy-3-phenyl propionic acid |
| Hinp | (2S)-2-Hydroxy-3-(indol-3'-yl)-propionic acid |
| Dhp | (2S)-2,3-Dihydroxy-propionic acid |
| Hbd | (2S)-2-Hydroxybutanedioic acid |
| Hpd | (2S)-2-Hydroxy-pentanedioic acid |
| Ahh | (2S)-6-Amino-2-hydroxy-hexanoic acid |
| Hgp | (2S)-2-Hydroxy-5-guanidino-pentanoic acid |
| Hmcp | (2S)-2-Hydroxy-3-mercapto-propionic acid |
| Haa | 2-Hydroxy acetic acid |
| Hcp | 2-Hydroxy-3-carbamoyl-propanoic acid |
| Hcb | 2-Hydroxy-4-carbamoyl-butanoic acid |
| 3Dhb | (2S,3R)-2,3-Dihydroxy-butyric acid |
| Hpa | (2S)-2-Hydroxy-2-phenylacetic acid |
| Ahp | (2S)-3-Amino-2-hydroxy-propionic acid |
| Ahb | (2S)-4-Amino-2-hydroxy butyric acid |
| 3Ahb | (2S,3S)-3-Amino-2-hydroxy butyric acid |
| 4Dhb | (2S)-2,4-Dihydroxy butyric acid |
| Hmcb | (2S)-2-Hydroxy-4-mercapto-butyric acid |
| Hpb | (2S)-2-Hydroxy-4-phenyl-butyric acid |
| Hcb | (2S)-2-Hydroxy-4-cyclohexyl-butyric acid |
| Hgh | (2S)-2-Hydroxy-6-guanidino-hexanoic acid |
| Hcap | 2-Hydroxy-5-(carbamoylamino)pentanoic acid |
| Ahp | (2S)-5-Amino-2-hydroxy-pentanoic acid |
| Hdmp | (2S)-2-Hydroxy-4,4-dimethyl pentanoic acid |
| Hdmb | (2S)-2-Hydroxy-3,3-dimethyl butyric acid |
| Hchp | (2S)-2-Hydroxy-3-cyclohexyl propionic acid |
| Hcbp | (2S)-2-Hydroxy-3-cyclobutyl propionic acid |
| Hcpp | (2S)-2-Hydroxy-3-cyclopentyl propionic acid |
| Hca | (2S)-2-Hydroxy caproic acid |
| Hda | (2S)-2-Hydroxy decanoic acid |
| H2np | (2S)-2-Hydroxy-3-(2'-naphthyl)propionic acid |
| H1np | (2S)-2-Hydroxy-3-(1'-naphthyl)propionic acid |
| Hbp | (23)-2-Hydroxy-3-biphenyl-4'-yl propionic acid |
| 4Clphp | (2S)-3-(4'-Chlorophenyl)-2-hydroxy propionic acid |
| 3Clphp | (2S)-3-(3'-Chlorophenyl)-2-hydroxy propionic acid |
| 2Clphp | (2S)-3-(2'-Chlorophenyl)-2-hydroxy propionic acid |
| 4Fphp | (2S)-3-(4'-Fluorophenyl)-2-hydroxypropionic acid |
| 3Fphp | (2S)-3-(3'-Fluorophenyl)-2-hydroxy propionic acid |
| 2Fphp | (2S)-3-(2'-Fluorophenyl)-2-hydroxy propionic acid |
| Aahh | (2S)-6-Acetylamino-2-hydroxy-hexanoic acid |
| Hbpp | (2S)-2-Hydroxy-3-4'-benzoylphenyl propionic acid |
| Bhp | (2S)-3-Benzyloxy-2-hydroxy-propionic acid |
| Bhb | (2S,3R)-3-Benzyloxy-2-hydroxy-butyric acid |
| Hbpp | (2S)-2-Hydroxy-3-(4'-benzyloxyphenyl)-propionic acid |

| | |
|---|---|
| 4Hb | 4-Hydroxy butyric acid |
| 6Hh | 6-Hydroxy hexanoic acid |
| Hib | 2-Hydroxy isobutyric acid |

In addition, the most preferred values for B also include groups of type A8″ of (L)-configuration:

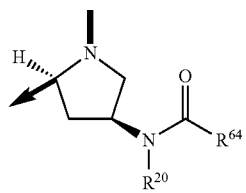

wherein $R^{20}$ is H or lower alkyl and $R^{64}$ is alkyl; alkenyl; $-[(CH_2)_u-X]_t-CH_3$ (where X is $-O-$; $-NR^{20}-$, or $-S-$; u=1-3, and t=1-6), aryl; aryl-lower alkyl; or heteroaryl-lower alkyl; especially those wherein $R^{64}$ is n-hexyl (A8″-21); n-heptyl (A8″-22); 4-(phenyl)benzyl (A8″-23); diphenylmethyl (A8″-24); 3-amino-propyl (A8″-25); 5-amino-pentyl (A8″-26); methyl (A8″-27); ethyl (A8″-28); isopropyl (A8″-29); isobutyl(A8″-30); n-propyl (A8″-31); cyclohexyl (A8″-32); cyclohexyl-methyl (A8″-33); n-butyl (A8″-34); phenyl (A8″-35); benzyl (A8″-36); (3-indolyl)methyl (A8″-37); 2-(3-indolyl)ethyl (A8″-38); (4-phenyl)-phenyl (A8″-39); n-nonyl (A8″-40); $CH_3-OCH_2CH_2-OCH_2-$ (A8″-41) and $CH_3-(OCH_2CH_2)_2-OCH_2-$ (A8″-42).

In a particular embodiment the template is $^D$Pro-$^L$Pro or $^L$Pro-$^D$Pro or a group corresponding thereto but in which the $^D$Pro moiety and/or the $^L$Pro moiety is substituted as shown in Formula A8′ and, respectively, A8″, above.

The peptidic or depsipeptidic chain Z of the β-hairpin mimetics described herein is generally defined in terms of amino acid or hydroxy acid residues belonging to one of the following groups:

Group C $-NR^{20}H(R^{72})CO-$; "hydrophobic: small to medium-sized"

Group D $-NR^{20}CH(R^{73})CO-$; "hydrophobic: large aromatic or heteroaromatic"

Group E $-NR^{20}H(R^{74})CO-$; "polar-cationic" and "urea-derived"

Group F $-NR^{20}CH(R^{84})CO-$; "polar-non-charged or anionic"

Group H $-NR^{20}-CH(CO-)-(CH_2)_{4-7}-CH(CO-)-NR^{20}-$; $-NR^{20}-CH(CO-)-(CH_2)_p SS(CH_2)_p-CH(CO-)-NR^{20}-$; $-NR^{20}-CH(CO-)-(-(CH_2)_p NR^{20}CO(CH_2)_p-CH(CO-)-NR^{20}-$; and $-NR^{20}-CH(CO-)-(-(CH_2)_p NR^{20}CONR^{20}(CH_2)_p-CH(CO-)-NR^{20}-$; "interstrand linkage"

Group L $-OCH(R^{71})CO-$; $-OCH(R^{72})CO-$; $-OCH(R^{72})CO-$; $-OCH(R^{74})CO-$; $-OCH(R^{84})CO-$ Furthermore, the amino acid residues in chain Z can also be of formula -A-CO— wherein A is as defined above. Finally, Pro and Gly can also be amino acid residues and the residue of glycolic acid can also be a hydroxy acid residue in chain Z with the exception of positions where interstrand linkages (H) are possible.

Group C comprises amino acid residues with small to medium-sized hydrophobic side chain groups according to the general definition for substituent $R^{72}$. A hydrophobic residue refers to an amino acid side chain that is uncharged at physiological pH and that is repelled by aqueous solution. Furthermore these side chains generally do not contain hydrogen bond donor groups, such as (but not limited to) primary and secondary amides, primary and secondary amines and the corresponding protonated salts thereof, thiols, alcohols, phosphonates, phosphates, ureas or thioureas. However, they may contain hydrogen bond acceptor groups such as ethers, thioethers, esters, tertiary amides, alkyl- or aryl phosphonates and phosphates or tertiary amines. Genetically encoded small-to-medium-sized hydrophobic amino acids include alanine, isoleucine, leucine, methionine and valine.

Group D comprises amino acid residues with aromatic and heteroaromatic side chain groups according to the general definition for substituent $R^{73}$. An aromatic amino acid residue refers to a hydrophobic amino acid having a side chain containing at least one ring having a conjugated π-electron system (aromatic group). In addition they may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tertiary amides, alkyl—or aryl phosphonates—and phosphates or tertiary amines. Genetically encoded aromatic amino acids include phenylalanine and tyrosine.

A heteroaromatic amino acid residue refers to a hydrophobic amino acid having a side chain containing at least one ring having a conjugated π-system incorporating at least one heteroatom such as (but not limited to) O, S and N according to the general definition for substituent $R^{77}$. In addition such residues may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tertiary amides, alkyl—or aryl phosphonates—and phosphates or tertiary amines. Genetically encoded heteroaromatic amino acids include tryptophan and histidine.

Group E comprises amino acids containing side chains with polar-cationic, acylamino- and urea-derived residues according to the general definition for substituent $R^{74}$. Polar-cationic refers to a basic side chain which is protonated at physiological pH. Genetically encoded polar-cationic amino acids include arginine, lysine and histidine. Citrulline is an example for an urea derived amino acid residue.

Group F comprises amino acids containing side chains with polar-non-charged or anionic residues according to the general definition for substituent $R^{84}$. A polar-non-charged or anionic residue refers to a hydrophilic side chain that is uncharged and, respectively anionic at physiological pH (carboxylic acids being included), but that is not repelled by aqueous solutions. Such side chains typically contain hydrogen bond donor groups such as (but not limited to) primary and secondary amides, carboxyclic acids and esters, primary and secondary amines, thiols, alcohols, phosphonates, phosphates, ureas or thioureas. These groups can form hydrogen bond networks with water molecules. In addition they may also contain hydrogen bond acceptor groups such as (but not limited to) ethers, thioethers, esters, tertiary amides, carboxylic acids and carboxylates, alkyl—or aryl phosphonates—and phosphates or tertiary amines. Genetically encoded polarnon-charged amino acids include asparagine, cysteine, glutamine, serine and threonine, but also aspartic acid and glutamic acid.

Group H comprises side chains of preferably (L)-amino acids at opposite positions of the β-strand region that can form an interstrand linkage. The most widely known linkage is the disulfide bridge formed by cysteines and homo-cysteines positioned at opposite positions of the β-strand. Various methods are known to form disulfide linkages including those described by: J. P. Tam et al. *Synthesis* 1979, 955-957; Stewart et al., *Solid Phase Peptide Synthesis*, 2d Ed., Pierce Chemical Company, Ill., 1984; Ahmed et al. *J. Biol. Chem.* 1975, 250, 8477-8482; and Pennington et al., *Peptides*, pages 164-166, Giralt and Andreu, Eds., ESCOM Leiden, The Netherlands, 1990. Most advantageously, for the scope of the present invention, disulfide linkages can be prepared using acetamidomethyl (Acm)-protective groups for cysteine. A well established interstrand linkage consists in linking ornithines and lysines, respectively, with glutamic and aspartic acid residues located at opposite β-strand positions by means of an amide bond formation. Preferred protective groups for the side-chain amino groups of ornithine and lysine are allyloxycarbonyl (Alloc) and allylesters for aspartic and glutamic acid. Finally, interstrand linkages can also be established by linking the amino groups of lysine and ornithine located at opposite β-strand positions with reagents such as N,N-carbonyl-imidazole to form cyclic ureas.

Group L comprises hydroxy acid residues with side chain groups according to the general definition for substituent $R^{71}$; hydroxy acid residues with small to medium-sized hydrophobic side chain groups according to the general definition for substituent $R^{72}$; hydroxy acid residues with aromatic and heteroaromatic side chain groups according to the general definition for substituent $R^{73}$; hydroxy acid residues with polar-cationic, acylamino- and urea-derived side chain groups according to the general definition for substituent $R^{74}$; and hydroxy acid residues with polar-non-charged or anionic groups according to the general definition for substituent $R^{84}$. Hydrophobic side chain groups are uncharged at physiological pH and repelled by aqueous solution. An aromatic side chain group is hydrophobic and contains at least one ring having a conjugated π-electron system (aromatic group). A heteroaromatic side chain group is hydrophobic and contains at least one ring having a conjugated n-system incorporating at least one heteroatom such as (but not limited to) O, S and N according to the general definition for substituent $R^{77}$. A polar-cationic side chain group refers to a basic side chain which is protonated at physiological pH. A polar-non-charged or anionic side chain group is uncharged and, respectively anionic at physiological pH (carboxylic acids being included), but is not repelled by aqueous solutions.

As mentioned earlier, positions for interstrand linkages are positions P4 and P11 taken together. Such interstrand linkages are known to stabilize the β-hairpin conformations and thus constitute an important structural element for the design of β-hairpin mimetics.

Most preferred amino acid residues in chain Z are those derived from natural α-amino acids. Hereinafter follows a list of amino and hydroxy acids which, or the residues of which, are suitable for the purposes of the present invention, the abbreviations corresponding to generally adopted usual practice:

| three letter code | | one letter code |
|---|---|---|
| Ala | L-Alanine | A |
| Arg | L-Arginine | R |
| Asn | L-Asparagine | N |
| Asp | L-Aspartic acid | D |
| Cys | L-Cysteine | C |
| Glu | L-Glutamic acid | E |
| Gln | L-Glutamine | Q |
| $^D$Gln | D-Glutamine | $^D$Q |
| Gly | Glycine | G |
| His | L-Histidine | H |
| Ile | L-Isoleucine | I |
| Leu | L-Leucine | L |
| Lys | L-Lysine | K |
| Met | L-Methionine | M |
| Phe | L-Phenylalanine | F |
| Pro | L-Proline | P |
| $^D$Pro | D-Proline | $^D$P |
| Ser | L-Serine | S |
| $^D$Ser | D-Serine | $^D$S |
| Thr | L-Threonine | T |
| Trp | L-Tryptophan | W |
| Tyr | L-Tyrosine | Y |
| Val | L-Valine | V |

| | Glycolic acid |
|---|---|
| Lac | (2S)-2-Hydroxy-propanoic acid |
| Hmb | (2S)-2-Hydroxy-3-methylbutyric acid |
| H3mp | (2S,3S)-2-Hydroxy-3-methyl-pentanoic acid |
| H4mp | (2S)-2-Hydroxy-4-methyl-pentanoic acid |
| Hmtb | (2S)-2-Hydroxy-4-methylthio butyric acid |
| Hhpp | (2S)-2-Hydroxy-3-(4'-hydroxyphenyl)-propionic acid |
| Himp | (2S)-2-Hydroxy-3-(Imidazole-4'-yl)-propionic acid |
| Hpp | (2S)-2-Hydroxy-3-phenyl propionic acid |
| Hinp | (2S)-2-Hydroxy-3-(indol-3'-yl)-propionic acid |
| Dhp | (2S)-2,3-Dihydroxy-propionic acid |
| Hbd | (2S)-2-Hydroxybutanedioic acid |
| Hpd | (2S)-2-Hydroxy-pentanedioic acid |
| Ahh | (2S)-6-Amino-2-hydroxy-hexanoic acid |
| Hgp | (2S)-2-Hydroxy-5-guanidino-pentanoic acid |
| Hmcp | (2S)-2-Hydroxy-3-mercapto-propionic acid |
| Haa | 2-Hydroxy acetic acid |
| Hcp | 2-Hydroxy-3-carbamoyl-propanoic acid |
| Hcb | 2-Hydroxy-4-carbamoyl-butanoic acid |
| 3Dhb | (2S,3R)-2,3-Dihydroxy-butyric acid |

Other α-amino or hydroxy acids which, or the residues of which, are suitable for the purposes of the present invention include:

| | |
|---|---|
| Cit | L-Citrulline |
| Orn | L-Ornithine |
| tBuA | L-t-Butylalanine |
| Sar | Sarcosine |
| Pen | L-Penicillamine |
| t-BuG | L-tert.-Butylglycine |
| 4AmPhe | L-para-Aminophenylalanine |
| 3AmPhe | L-meta-Aminophenylalanine |
| 2AmPhe | L-ortho-Aminophenylalanine |
| Phe(mC(NH$_2$)=NH) | L-meta-Amidinophenylalanine |
| Phe(pC(NH$_2$)=NH) | L-para-Amidinophenylalanine |
| Phe(mNHC(NH$_2$)=NH) | L-meta-Guanidinophenylalanine |
| Phe(pNHC(NH$_2$)=NH) | L-para-Guanidinophenylalanine |
| Phg | L-Phenylglycine |
| Cha | L-Cyclohexylalanine |
| C$_4$al | L-3-Cyclobutylalanine |
| C$_5$al | L-3-Cyclopentylalanine |
| Nle | L-Norleucine |
| 2-Nal | L-2-Naphthylalanine |
| 1-Nal | L-1-Naphthylalanine |
| 4Cl-Phe | L-4-Chlorophenylalanine |

-continued

| | |
|---|---|
| 3Cl-Phe | L-3-Chlorophenylalanine |
| 2Cl-Phe | L-2-Chlorophenylalanine |
| 3,4Cl$_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Tic | 1,2,3,4-Tetrahydroisoquinoline-3-carboxylic acid |
| Oic | (2S,3aS,7aS)-1-Octahydro-1H-indole-2-carboxylic acid |
| Thi | L-β-2-Thienylalanine |
| Tza | L-2-Thiazolylalanine |
| Mso | L-Methionine sulfoxide |
| AcLys | N-Acetyllysine |
| Dpr | 2,3-Diaminopropionic acid |
| A$_2$Bu | 2,4-Diaminobutyric acid |
| Dab | (S)-2,3-Diaminobutyric acid |
| Abu | γ-Aminobutyric acid (GABA) |
| Aha | ε-Aminohexanoic acid |
| Aib | α-Aminoisobutyric acid |
| Y(Bzl) | L-O-Benzyltyrosine |
| Bip | L-(4-phenyl)phenylalanine |
| S(Bzl) | L-O-Benzylserine |
| T(Bzl) | L-O-Benzylthreonine |
| hCha | L-Homo-cyclohexylalanine |
| hCys | L-Homo-cysteine |
| hSer | L-Homo-serine |
| hArg | L-Homo-arginine |
| hPhe | L-Homo-phenylalanine |
| Bpa | L-4-Benzoylphenylalanine |
| 4-AmPyrr1 | (2S,4S)-4-Amino-pyrrolidine-L-carboxylic acid |
| 4-AmPyrr2 | (2S,4R)-4-Amino-pyrrolidine-L-carboxylic acid |
| 4-PhePyrr1 | (2S,5R)-4-Phenyl-pyrrolidine-L-carboxylic acid |
| 4-PhePyrr2 | (2S,5S)-4-Phenyl-pyrrolidine-L-carboxylic acid |
| 5-PhePyrr1 | (2S,5R)-5-Phenyl-pyrrolidine-L-carboxylic acid |
| 5-PhePyrr2 | (2S,5S)-5-Phenyl-pyrrolidine-L-carboxylic acid |
| 4Hyp1 | (4S)-L-Hydroxyproline |
| 4Hyp2 | (4R)-L-Hydroxyproline |
| 4Mp1 | (4S)-L-Mercaptoproline |
| 4Mp2 | (4R)-L-Mercaptoproline |
| Pip | L-Pipecolic acid |
| OctG | L-Octylglycine |
| NGly | N-Methylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methylvaline |
| MeLeu | L-N-Methylleucine |
| Hpa | (2S)-2-Hydroxy-2-phenylacetic acid |
| Ahp | (2S)-3-Amino-2-hydroxy-propionic acid |
| Ahb | (2S)-4-Amino-2-hydroxy butyric acid |
| 3Ahb | (2S,3S)-3-Amino-2-hydroxy butyric acid |
| 4Dhb | (2S)-2,4-Dihydroxy butyric acid |
| Hmcb | (2S)-2-Hydroxy-4-mercapto-butyric acid |
| Hpb | (2S)-2-Hydroxy-4-phenyl-butyric acid |
| Hcb | (2S)-2-Hydroxy-4-cyclohexyl-butyric acid |
| Hgh | (2S)-2-Hydroxy-6-guanidino-hexanoic acid |
| Hcap | (2S)-2-Hydroxy-5-(carbamoylamino)pentanoic acid |
| Ahp | (2S)-5-Amino-2-hydroxy-pentanoic acid |
| Hdmp | (2S)-2-Hydroxy-4,4-dimethyl pentanoic acid |
| Hdmb | (2S)-2-Hydroxy-3,3-dimethyl butyric acid |
| Hchp | (2S)-2-Hydroxy-3-cyclohexyl propionic acid |
| Hcbp | (2S)-2-Hydroxy-3-cyclobutyl propionic acid |
| Hcpp | (2S)-2-Hydroxy-3-cyclopenyl propionic acid |
| Hca | (2S)-2-Hydroxy caproic acid |
| Hda | (2S)-2-Hydroxy decanoic acid |
| H2np | (2S)-2-Hydroxy-3-(2'-naphthyl)propionic acid |
| H1np | (2S)-2-Hydroxy-3-(1'-naphthyl)propionic acid |
| Hbp | (2S)-2-Hydroxy-3-biphenyl-4'-yl propionic acid |
| 4Clphp | (2S)-3-(4'-Chlorophenyl)-2-hydroxy propionic acid |
| 3Clphp | (2S)-3-(3'-Chlorophenyl)-2-hydroxy propionic acid |
| 2Clphp | (2S)-3-(2'-Chlorophenyl)-2-hydroxy propionic acid |
| 4Fphp | (2S)-3-(4'-Fluorophenyl)-2-hydroxy propionic acid |
| 3Fphp | (2S)-3-(3'-Fluorophenyl)-2-hydroxy propionic acid |
| 2Fphp | (2S)-3-(2'-Fluorophenyl)-2-hydroxy propionic acid |
| Aahh | (2S)-6-Acetylamino-2-hydroxy-hexanoic acid |
| Hbpp | (2S)-2-Hydroxy-3-4'-benzoylphenyl propionic acid |
| Bhp | (2S)-3-Benzyloxy-2-hydroxy-propionic acid |
| Bhb | (2S,3R)-3-Benzyloxy-2-hydroxy-butyric acid |
| Hbpp | (2S)-2-Hydroxy-3-(4'-benzyloxyphenyl)-propionic acid |
| 4Hb | 4-Hydroxy butyric acid |
| 6Hh | 6-Hydroxy hexanoic acid |
| Hib | 2-Hydroxy isobutyric acid |

Particularly preferred residues for group C are:

| | |
|---|---|
| Ala | L-Alanine |
| Ile | L-Isoleucine |
| Leu | L-Leucine |
| Met | L-Methionine |
| Val | L-Valine |
| tBuA | L-t-Butylalanine |
| t-BuG | L-tert.-Butylglycine |
| Cha | L-Cyclohexylalanine |
| C$_4$al | L-3-Cyclobutylalanine |
| C$_5$al | L-3-Cyclopentylalanine |
| Nle | L-Norleucine |
| hCha | L-Homo-cyclohexylalanine |
| OctG | L-Octylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methylvaline |
| MeLeu | L-N-Methylleucine |

Particularly preferred residues for group D are:

| | |
|---|---|
| His | L-Histidine |
| Phe | L-Phenylalanine |
| Trp | L-Tryptophan |
| Tyr | L-Tyrosine |
| Phg | L-Phenylglycine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl$_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Thi | L-β-2-Thienylalanine |
| Tza | L-2-Thiazolylalanine |
| Y(Bzl) | L-O-Benzyltyrosine |
| Bip | L-Biphenylalanine |
| S(Bzl) | L-O-Benzylserine |
| T(Bzl) | L-O-Benzylthreonine |
| hPhe | L-Homo-phenylalanine |
| Bpa | L-4-Benzoylphenylalanine |
| PirrAla | L-2-(3'-pyrrolidinyl)-alanine |
| NMePhe | L-N-Methylphenylalanine |
| 4-PyrAla | L-2-(4'Pyridyl)-alanine |

Particularly preferred residues for group E are

| | |
|---|---|
| Arg | L-Arginine |
| Lys | L-Lysine |
| Orn | L-Ornithine |
| Dpr | L-2,3-Diaminopropionic acid |
| A$_2$Bu | L-2,4-Diaminobutyric acid |
| Dab | (2S,3S)-2,3-Diaminobutyric acid |
| Phe(pNH$_2$) | L-para-Aminophenylalanine |
| Phe(mNH$_2$) | L-meta-Aminophenylalanine |
| Phe(oNH$_2$) | L-ortho-Aminophenylalanine |
| hArg | L-Homo-arginine |
| Phe(mC(NH$_2$)=NH) | L-meta-Amidinophenylalanine |
| Phe(pC(NH$_2$)=NH) | L-para-Amidinophenylalanine |
| Phe(mNHC(NH$_2$)=NH) | L-meta-Guanidinophenylalanine |
| Phe(pNHC(NH$_2$)=NH) | L-para-Guanidinophenylalanine |
| NMeR | L-N-Methylarginine |
| NMeK | L-N-Methyllysine |

Particularly preferred residues for group F are

| | |
|---|---|
| Asn | L-Asparagine |
| Asp | L-Aspartic acid |
| Cys | L-Cysteine |
| Gln | L-Glutamine |
| $^D$Gln | D-Glutamine |
| Glu | L-Glutamic acid |
| Ser | L-Serine |
| $^D$Ser | D-Serine |
| Thr | L-Threonine |
| Cit | L-Citrulline |
| Pen | L-Penicillamine |
| AcLys | L-N'-Acetyllysine |
| hCys | L-Homo-cysteine |
| hSer | L-Homo-serine |

Particularly preferred residues for group L are

| | |
|---|---|
| Lac | (2S)-2-Hydroxy-propanoic acid |
| Hmb | (2S)-2-Hydroxy-3-methylbutyric acid |
| H3mp | (2S,3S)-2-Hydroxy-3-methyl-pentanoic acid |
| H4mp | (2S)-2-Hydroxy-4-methyl-pentanoic acid |
| Hmtb | (2S)-2-Hydroxy-4-methylthio butyric acid |
| Hhpp | (2S)-2-Hydroxy-3-(4'-hydroxyphenyl)-propionic acid |
| Himp | (2S)-2-Hydroxy-3-(Imidazole-4'-yl)-propionic acid |
| Hpp | (2S)-2-Hydroxy-3-phenyl propionic acid |
| Hinp | (2S)-2-Hydroxy-3-(indol-3'-yl)-propionic acid |
| Dhp | (2S)-2,3-Dihydroxy-propionic acid |
| Hbd | (2S)-2-Hydroxybutanedioic acid |
| Hpd | (2S)-2-Hydroxy-pentanedioic acid |
| Ahh | (2S)-6-Amino-2-hydroxy-hexanoic acid |
| Hgp | (2S)-2-Hydroxy-5-guanidino-pentanoic acid |
| Hmcp | (2S)-2-Hydroxy-3-mercapto-propionic acid |
| Haa | 2-Hydroxy acetic acid |
| Hcp | 2-Hydroxy-3-carbamoyl-propanoic acid |
| Hcb | 2-Hydroxy-4-carbamoyl-butanoic acid |
| 3Dhb | (2S,3R)-2,3-Dihydroxy-butyric acid |
| Hpa | (2S)-2-Hydroxy-2-phenylacetic acid |
| Ahp | (2S)-3-Amino-2-hydroxy-propionic acid |
| Ahb | (2S)-4-Amino-2-hydroxy butyric acid |
| 3Ahb | (2S,3S)-3-Amino-2-hydroxy butyric acid |
| 4Dhb | (2S)-2,4-Dihydroxy butyric acid |
| Hmcb | (2S)-2-Hydroxy-4-mercapto-butyric acid |
| Hpb | (2S)-2-Hydroxy-4-phenyl-butyric acid |
| Hcb | (2S)-2-Hydroxy-4-cyclohexyl-butyric acid |
| Hgh | (2S)-2-Hydroxy-6-guanidino-hexanoic acid |
| Hcap | 2-Hydroxy-5-(carbamoylamino)pentanoic acid |
| Ahp | (2S)-5-Amino-2-hydroxy-pentanoic acid |
| Hdmp | (2S)-2-Hydroxy-4,4-dimethyl pentanoic acid |
| Hdmb | (2S)-2-Hydroxy-3,3-dimethyl butyric acid |
| Hchp | (2S)-2-Hydroxy-3-cyclohexyl propionic acid |
| Hcbp | (2S)-2-Hydroxy-3-cyclobutyl propionic acid |
| Hcpp | (2S)-2-Hydroxy-3-cyclopenyl propionic acid |
| Hca | (2S)-2-Hydroxy caproic acid |
| Hda | (2S)-2-Hydroxy decanoic acid |
| H2np | (2S)-2-Hydroxy-3-(2'-naphthyl)propionic acid |
| H1np | (2S)-2-Hydroxy-3-(1'-naphthyl)propionic acid |
| Hbp | (2S)-2-Hydroxy-3-biphenyl-4'-yl propionic acid |
| 4Clphp | (2S)-3-(4'-Chlorophenyl)-2-hydroxy propionic acid |
| 3Clphp | (2S)-3-(3'-Chlorophenyl)-2-hydroxy propionic acid |
| 2Clphp | (2S)-3-(2'-Chlorophenyl)-2-hydroxy propionic acid |
| 4Fphp | (2S)-3-(4'-Fluorophenyl)-2-hydroxy propionic acid |
| 3Fphp | (2S)-3-(3'-Fluorophenyl)-2-hydroxy propionic acid |
| 2Fphp | (2S)-3-(2'-Fluorophenyl)-2-hydroxy propionic acid |
| Aahh | (2S)-6-Acetylamino-2-hydroxy-hexanoic acid |
| Hbpp | (2S)-2-Hydroxy-3-4'-benzoylphenyl propionic acid |
| Bhp | (2S)-3-Benzyloxy-2-hydroxy propionic acid |
| Bhb | (2S,3R)-3-Benzyloxy-2-hydroxy-butyric acid |
| Hbpp | (2S)-2-Hydroxy-3-(4'-benzyloxyphenyl)-propionic acid |
| 4Hb | 4-Hydroxy butyric acid |
| 6Hh | 6-Hydroxy hexanoic acid |
| Hib | 2-Hydroxy isobutyric acid |

Generally, the peptidic or depsipeptidic chain Z within the β-hairpin mimetics of the invention comprises 14 amino and/or hydroxy acid residues. The positions P1 to P14 of each amino or hydroxy acid residue in the chain Z are unequivocally defined as follows: P1 represents the first amino or hydroxy acid in the chain Z that is coupled with its N- or O-terminus to the C-terminus of the templates (b)-(p), or of group —B—CO— in template (a1), or of group -A-CO— in template (a2); and P14 represents the last amino or hydroxy acid in the chain Z that is coupled with its C-terminus to the N- or O-terminus of the templates (b)-(p), or of group -A-CO— in template (a1), or of group —B—CO— in template (a2). Each of the positions P1 to P14 will contain an amino or hydroxy acid residue belonging to one of the above types C D, E, F, H or L, or of formula -A-CO—, or being Gly or a glycolic acid residue as stated above.

The α-amino and/or α-hydroxy acid residues in positions 1 to 14 of the chain Z are preferably:
P1: of type D or of type L;
P2: of type D or of type L;
P3: of type C, type D or of type L;
P4: of type F;
P5: of type E, type F or of type L;
P6: of type C or of type L;
P7: of formula -A-CO—, Gly or Pro
P8: of type E or of type L;
P9: of type E;
P10: of type D;
P11: of type F;
P12: of type D or of type L;
P13: of type F or of type L; and
P14: of type E or of type L; or
P4 and P11, taken together, can form a group of type H;
at P5, P7 and P13 also D-isomers being possible.

The α-amino and/or α-hydroxy acid residues in positions 1 to 14 are most preferably:
P1: Tyr, Hhpp;
P2: His, Ahb;
P3: Ala, Lac;
P4: Cys;
P5: Ser, Ahb, $^D$Ser, Arg;
P6: Lac, Ala;
P7: $^D$Pro;
P8: Dab, Ahb;
P9: Arg;
P10: Tyr;
P11: Cys;

P12: Tyr, Hhpp;
P13: Gln, Hhpp, $^D$Gln;
P14: Lys, Ahb;
formation of a disulfide bridge being possible between the Cys residues at P4 and P11.

Particularly preferred β-peptidomimetics of the invention include those described in Examples 1, 3 and 7.

The processes of the invention can advantageously be carried out as parallel array syntheses to yield libraries of template-fixed β-hairpin peptidomimetics of the above general formulae Ia or Ib. Such parallel syntheses allow one to obtain arrays of numerous (normally 12 to 192, typically 96) compounds of general formulae Ia or Ib in moderate to high yields and defined purities, minimizing the formation of dimeric and polymeric by-products. The proper choice of the functionalized solid-support (i.e. solid support plus linker molecule), templates and site of cyclization play thereby key roles.

The functionalized solid support is conveniently derived from polystyrene crosslinked with, preferably 1-5%, divinylbenzene; polystyrene coated with polyethyleneglycol spacers (Tentagel®); and polyacrylamide resins (see also D. Obrecht, J.-M. Villalgordo, "Solid-Supported Combinatorial and Parallel Synthesis of Small-Molecular-Weight Compound Libraries", *Tetrahedron Organic Chemistry Series*, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acid conditions (H. Rink, *Tetrahedron Lett.* 1987, 28, 3783-3790). Linkers of this kind form amides of the carboxyl group of the amino or hydroxy acids; examples of resins functionalized by such linker structures include 4-[(((2,4-dimethoxyphenyl)Fmoc-aminomethyl)phenoxyacetamido) aminomethyl] PS resin, 4-[(((2,4-dimethoxyphenyl)Fmoc-aminomethyl)phenoxyacetamido)aminomethyl]-4-methyl-benzhydrylamine PS resin (Rink amide MBHA PS Resin), and 4-[(((2,4-dimethoxyphenyl)Fmoc-aminomethyl)phenoxyacetamido)aminomethyl]benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxy-phenyl)Fmoc-aminomethyl)phenoxyacetamido) linker.

Type 2 linkers are designed to eventually release the carboxyl group under acidic conditions. Linkers of this kind form acid-labile esters with the carboxyl group of the amino or hydroxy acids, usually acid-labile benzyl, benzhydryl and trityl esters; examples of such linker structures include 2-methoxy-4-hydroxymethylphenoxy (Sasrin® linker), 4-(2, 4-di-methoxyphenyl-hydroxymethyl)-phenoxy (Rink linker), 4-(4-hydroxymethyl-3-methoxyphenoxy)butyric acid (HMPB linker), trityl and 2-chlorotrityl. Preferably, the support is derived from polystyrene crosslinked with, most preferably 1-5%, divinylbenzene and functionalized by means of the 2-chlorotrityl linker.

When carried out as parallel array syntheses the processes of the invention can be advantageously carried out as described herein below but it will be immediately apparent to those skilled in the art how these procedures will have to be modified in case it is desired to synthesize one single compound of the above formulae Ia or Ib.

A number of reaction vessels (normally 12 to 192, typically 96) equal to the total number of compounds to be synthesized by the parallel method are loaded with 25 to 1000 mg, preferably 60 mg, of the appropriate functionalized solid support, preferably 1 to 3% cross-linked polystyrene or Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e. g. 20% TFE/DCM, 35% THF/NMP) are beneficial for ensuring high reactivity and solvation of the resin-bound peptide chains (G. B. Fields, C. G. Fields, *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin® linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2,4-dimethoxyphenyl-hydroxymethyl)-phenoxy linker (Rink linker, H. Rink, *Tetrahedron Lett.* 1987, 28, 3787-3790), where the removal of the depsipeptide requires 10% acetic acid in DCM or 0.2% trifluoroacetic acid in DCM; the 4-(4-hydroxymethyl-3-methoxyphenoxy)butyric acid-derived linker (HMPB-linker, Flörsheimer & Riniker, *Peptides* 1991, 1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the depsipeptide detachment using a mixture of glacial acetic acid/trifluoroethanol/DCM (1:2:7) for 30 min.

Suitable protecting groups for amino or hydroxy acids and, respectively, for their residues are, for example, for the amino group (as is present e. g. also in the side-chain of lysine)

| | |
|---|---|
| Cbz | benzyloxycarbonyl |
| Boc | tert.-butyloxycarbonyl |
| Fmoc | 9-fluorenylmethoxycarbonyl |
| Alloc | allyloxycarbonyl |
| Teoc | trimethylsilylethoxycarbonyl |
| Tcc | trichloroethoxycarbonyl |
| Nps | o-nitrophenylsulfonyl; |
| Trt | triphenymethyl or trityl | for the carboxyl group (as is present e. g. also in the side-chain of aspartic and glutamic acid) by conversion into esters with the alcohol components

| | |
|---|---|
| tBu | tert.-butyl |
| Bn | benzyl |
| Me | methyl |
| Ph | phenyl |
| Pac | phenacyl |
| | allyl |
| Tse | trimethylsilylethyl |
| Tce | trichloroethyl; | for the guanidino group (as is present e. g. in the side-chain of arginine)

| | |
|---|---|
| Pmc | 2,2,5,7,8-pentamethylchroman-6-sulfonyl |
| Ts | tosyl (i.e. p-toluenesulfonyl) |
| Cbz | benzyloxycarbonyl |
| Pbf | pentamethyldihydrobenzofuran-5-sulfonyl | for the hydroxy group (as is present e. g. in the side-chain of threonine and serine)

| | |
|---|---|
| tBu | tert.-butyl |
| Bn | benzyl |
| Trt | trityl |
| Alloc | allyloxycarbonyl | and for the mercapto group (as is present e. g. in the side-chain of cysteine)

| | |
|---|---|
| Acm | acetamidomethyl |
| tBu | tert.-butyl |
| Bn | benzyl |
| Trt | trityl |
| Mtr | 4-methoxytrityl. |

The 9-fluorenylmethoxycarbonyl-(Fmoc)-protected amino acid derivatives are preferably used as the building blocks for the construction of the template-fixed β-hairpin loop mimetics of formulae Ia or Ib. For the deprotection, i. e. cleaving off of the Fmoc group, 20% piperidine in DMF or 2% DBU/2% piperidine in DMF can be used.

The quantity of the reactant, i. e. of the amino or hydroxy acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The preferred workstations (without, however, being limited thereto) are Labsource's Combi-chem station, Protein Technologies' Symphony and MultiSyn Tech's-Syro synthesizer, the latter additionally equipped with a transfer unit and a reservoir box during the process of detachment of the fully protected linear peptide from the solid support. All synthesizers are able to provide a controlled environment, for example, reactions can be accomplished at temperatures different from room temperature as well as under inert gas atmosphere, if desired.

Amide bond formation requires the activation of the α-carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and, respectively, diisopropylurea is insoluble and, respectively, soluble in the solvents generally used. In a variation of the carbodiimide method 1-hydroxybenzotriazole (HOBt, Konig & Geiger, *Chem. Ber.* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethyl-amino)-phosphonium hexafluorophosphate (BOP, Castro et al., *Tetrahedron Lett.* 1975, 14, 1219-1222; *Synthesis* 1976, 751-752), or benzotriazol-1-yl-oxy-tris-pyrrolidino-phosphonium hexaflurophoshate (Py-BOP, Coste et al., *Tetrahedron Lett.* 1990, 31, 205-208), or 2-(1H-benzotriazol-1-yl-)1,1,3,3-tetramethyluronium tetrafluoroborate (TBTU), or hexafluorophosphate (HBTU, Knorr et al., *Tetrahedron Lett.* 1989, 30, 1927-1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279-2281) or -(6-Chloro-1H-benzotriazol-1-yl-)-N,N,N',N'-1,1,3,3-tetramethyluronium tetrafluoroborate (TCTU), or hexafluorophosphate (HCTU, Marder, Shivo and Albericio: HCTU and TCTU: New Coupling Reagents: Development and Industrial Applications, Poster Presentation, Gordon Conference February 2002) have also been used as coupling reagents.

Ester bond formation, or more precisely, the acylation of the α-hydroxy group requires more potent carboxyl-activating reagents than described above. Activation with DIC in the presence of 4-Dimethylaminopyridine (DMAP, J. W. Blankenship et al., *Biochemistry*, 2002, 41, 15676-15684) or the generation of the symmetric anhydride in the presence of DMAP (E. Bianchi et al., *Anal. Biochem.*, 1996, 237, 329-244) or the use of 1-(2-mesitylenesulfonyl)-3-nitro-1,2,4-triazole (MSNT) in the presence of N-methylimidazole (NMI) and DIEA (L. J. Cruz et al., *J. Org. Chem.*, 2006, 71, 3339-3344) have been described.

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide or depsipeptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction vessel is washed free of excess of retained reagents, of solvents, and of by-products by repetitive exposure to pure solvent(s) by one of the two following methods:

1) The reaction vessels are filled with solvent (preferably 5 ml), agitated for 5 to 300 minutes, preferably 15 minutes, and drained to expel the solvent;

2) The reaction vessels are filled with solvent (preferably 5 ml) and drained into a receiving vessel such as a test tube or vial.

Both of the above washing procedures are repeated up to about 50 times (preferably about 10 times), monitoring the efficiency of reagent, solvent, and by-product removal by methods such as TLC, GC, or inspection of the washings.

The above described procedure of reacting the resin-bound compound with reagents within the reaction tubes followed by removal of excess reagents, by-products, and solvents is repeated with each successive transformation until the final resin-bound fully protected linear depsipeptide has been obtained.

Before this fully protected linear peptide or depsipeptide is detached from the solid support, it is possible, if desired, to selectively deprotect one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (allyloxycarbonyl) is an example for such an amino protecting group which can be selectively removed, e.g. by means of $Pd^0$ and phenylsilane in $CH_2Cl_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced.

Before this fully protected linear peptide or depsipeptide is detached from the solid support, it is also possible, if desired, to form an interstrand linkages between side-chains of appropriate amino residues at positions P4 and P11.

Interstrand linkages and their formation have been discussed above, in connection with the explanations made regarding groups of the type H which can, for example, be disulfide bridges formed by cysteine and homocysteine residues at opposite positions of the β-strand; or lactam bridges formed by glutamic and aspartic acid residues linking ornithine and, respectively, lysine residues, or by glutamic acid residues linking 2,4-diaminobutyric acid residues located at opposite β-strand positions by amide bond formation. The formation of such interstrand linkages can be effected by methods well known in the art.

For the formation of disulfide bridges preferably a solution of 10 equivalents of iodine solution is applied in DMF or in a mixture of $CH_2Cl_2$/MeOH for 1.5 h which is repeated for another 3 h with a fresh iodine solution after filtering of the iodine solution, or in a mixture of DMSO and acetic acid solution, buffered with 5% with $NaHCO_3$ to pH 5-6 for 4 h, or in water after adjusting to pH 8 with ammonium hydroxide solution by stirring for 24 h, or in a solution of NMP and tri-n-butylphosphine (preferably 50 eq.).

For the formation of lactam bridges preferably a solution of 2 equivalents of HATU (N-[(dimethylamino)-1H-1,2,3-triazolo [4,5-b]pyridin-1-ylmethylene]-N-methylmethanaminium hexafluorophosphate N-oxide) in dry DMF and a solution of 4 equivalents of DIPEA (Diisopropyl ethylamine) in dry DMF is applied for 16 h.

Detachment of the fully protected linear peptide or depsipeptide from the solid support is achieved by exposing the loaded resin with a solution of the cleavage reagent (preferably 3 to 5 ml). Temperature control, agitation, and reaction monitoring are implemented as described above. Via a transfer-unit the reaction vessels are connected with a reservoir box containing reservoir tubes to efficiently collect the cleaved product solutions. The resins remaining in the reaction vessels are then washed 2 to 5 times as above with 3 to 5 ml of an appropriate solvent to extract (wash out) as much of the detached products as possible. The product solutions thus obtained are combined, taking care to avoid cross-mixing. The individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide or depsipeptide derivatives which have been cleaved off from the solid support and neutralized with a base, are evaporated to dryness. Cyclization is then effected in solution using solvents such as DCM, DMF, dioxane, THF and the like. Various coupling reagents which were mentioned earlier can be used for the cyclization. The duration of the cyclization is about 6-48 hours, preferably about 16 hours. The progress of the reaction is followed, e. g. by RP-HPLC (Reverse Phase High Performance Liquid Chromatography). Then the solvent is removed by evaporation, the fully protected cyclic depsipeptide derivative is dissolved in a solvent which is not miscible with water, such as DCM, and the solution is extracted with water or a mixture of water-miscible solvents, in order to remove any excess of the coupling reagent.

Alternatively, the detachment and complete deprotection of the fully protected peptide or depsipeptide from the solid support can be achieved manually in glass vessels.

Finally, the fully protected depsipeptide derivative is treated with 95% TFA, 2.5% $H_2O$, 2.5% TIS or another combination of scavengers for effecting the cleavage of protecting groups. The cleavage reaction time is commonly 30 minutes to 12 hours, preferably about 2.5 hours.

After full deprotection one of the following methods can be used for further work-up:

1) The solutions are evaporated to dryness and the crude peptide is dissolved in 20% AcOH in water and extracted with isopropyl ether or other solvents which are suitable therefor. The aqueous layer is collected and evaporated to dryness, and the fully deprotected depsipeptide derivative of formula Ia or Ib is obtained as end-product;

2) The deprotection mixture is concentrated under vacuum. Following precipitation of the fully deprotected depsipeptide in diethylether at preferably 0° C. the solid is washed up to about 10 times, preferably 3 times, dried, and the the fully deprotected depsipeptide derivative of formula Ia or Ib is obtained as end-product.

As mentioned earlier, it is thereafter possible, if desired, to convert a fully deprotected product of formula Ia or Ib thus obtained into a pharmaceutically acceptable salt or to convert a pharmaceutically acceptable, or unacceptable, salt thus obtained into the corresponding free compound of formula Ia or Ib or into a different, pharmaceutically acceptable, salt. Any of these operations can be carried out by methods well known in the art.

The template starting materials of formula IIa used in the processes of the invention, pre-starting materials therefore, and the preparation of these starting and pre-starting materials are described in International Application PCT/EP02/01711 of the same applicants, published as WO 02/070547 A1.

The β-hairpin peptidomimetics of the invention can be used in a wide range of applications in order to prevent HIV infections in non-infected individuals and slow or halt viral progression in infected patients, or where cancer is mediated or resulting from the CXCR4 receptor activity, or where immunological diseases are mediated or resulting from CXCR4 receptor activity; or the β-hairpin peptidomimetics of the invention can be used to treat immuno supersession, or they can be used during apheresis collections of peripheral blood stem cells and/or as agents to induce mobilization of stem cells to regulate tissue repair.

The β-hairpin peptidomimetics may be administered per se or may be applied as an appropriate formulation together with carriers, diluents or excipients well known in the art.

When used to treat or prevent HIV infections or cancer such as breast cancer, brain cancer, prostate cancer, lung cancer, kidney cancer, neuroblastoma, non-hodgkin's lymphoma, ovarian cancer, eye cancer, multiple myeloma, chronic lyphomphocytic leukemia, pancreatic cancer, melanoma, angiogenesis, and haematopoetic tissues; or inflammatory disorders such as asthma, allergic rhinitis, hypersensitivity lung diseases, hypersensitivity pneumonitis, eosinophilic pneumonias, delayed-type hypersensitivity, interstitial lung diseas (ILD), idiopathic pulmonary fibrosis, ILD associated with rheumatoid arthritis, systemic lupus erythematosus, ankylosing sponylitis, systemic sclerosis, Sjogren's syndrome, systemic anaphylaxis or hypersensitivity responses, drug allergies, rheumatoid arthritis, psoriatic arthritis, systemic lupus erythematosus, myasthenia gravis, juvenile onset diabetes, glomerulonephritis, autoimmune throiditis, graft rejection, including allograft rejection or graft-versus-host disease, inflammatory bowel diseases, inflammatory dermatoses; or to treat glaucoma; or to treat focal ischemic stroke, global cerebral ischemia, myocardial infarction, hind limb ischemia and peripheral ischemia; or to treat injury of the liver, kidney and lung or to treat immunosuppression, including immunosuppression induced by chemotherapy, radiation therapy or graft/transplantation rejection, the β-hairpin peptidomimetics can be administered singly, as mixtures of several β-hairpin peptidomimetics, in combination with other anti-HIV agents, or antimicrobial agents or anti cancer agents or anti-inflammatory agents, or in combination with other pharmaceutically active agents. The β-hairpin peptidomimetics can be administered per se or as pharmaceutical compositions.

Pharmaceutical compositions comprising n-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxilliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solutions may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion by a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the β-hairpin peptidomimetics of the invention are conveniently delivered in form of an aeorosol spray from pressurized packs or a nebulizer, with the use of a suitable propellant, e.g. dichlorodifluoromethane, trichiorofluromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as suppositories together with appropriate suppository bases such as cocoa butter or other glycerides.

In addition to the formulations described previously, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide may also be employed. Additionally, the β-hairpin peptidomimetics of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the β-hairpin pepdidomimetics of the invention may contain charged residues, they may be included in any of the above-described formulations as such or as pharmaceutically acceptable salts. Pharmaceutically acceptable salts tend to be more soluble in aqueous and other protic solvents than are the corresponding free forms.

The β-hairpin peptidomimetics of the invention, or compositions thereof, will generally be used in an amount effective to achieve the intended purpose. It is to be understood that the amount used will depend on a particular application.

For topical administration to treat or prevent HIV infections a therapeutically effective dose can be determined using, for example, the in vitro assays provided in the examples. The treatment may be applied while the HIV infection is visible, or even when it is not visible. An ordinary skilled expert will be able to determine therapeutically effective amounts to treat topical HIV infections without undue experimentation.

For systemic administration, a therapeutically effective dose can be estimated initially from in vitro assays. For example, a dose can be formulated in animal models to achieve a circulating β-hairpin peptidomimetic concentration range that includes the $IC_{50}$ as determined in the cell culture (i.e. the concentration of a test compound that is lethal to 50% of a cell culture). Such information can be used to more accurately determine useful doses in humans.

Initial dosages can also be determined from in vivo data, e.g. animal models, using techniques that are well known in the art. One having ordinary skill in the art could readily optimize administration to humans based on animal data.

Dosage amounts for applications as anti-HIV agents may be adjusted individually to provide plasma levels of the β-hairpin peptidomimetics of the invention which are sufficient to maintain the therapeutic effect. Therapeutically effective serum levels may be achieved by administering multiple doses each day.

In cases of local administration or selective uptake, the effective local concentration of the β-hairpin peptidomimetics of the invention may not be related to plasma concentration. One having the ordinary skill in the art will be able to optimize therapeutically effective local dosages without undue experimentation.

The amount of β-hairpin peptidomimetics administered will, of course, be dependent on the subject being treated, on the subject's weight, the severity of the affliction, the manner of administration and the judgement of the prescribing physician.

The anti-HIV therapy may be repeated intermittently while infections are detectable or even when they are not detectable. The therapy may be provided alone or in combination with other drugs, such as for example other anti-HIV agents or anti cancer agents, or other antimicrobial agents.

Normally, a therapeutically effective dose of the β-hairpin peptidomimetics described herein will provide therapeutic benefit without causing substantial toxicity.

Toxicity of the β-hairpin peptidomimetics of the invention can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, In: *The Pharmacological Basis of Therapeutics*, Ch. 1, p. 1).

The following Examples illustrate the present invention but are not to be construed as limiting its scope in any way.

EXAMPLES

1. Depsipeptide Synthesis

Coupling of the First Protected Amino or Hydroxy Acid Residue to the Resin 1 g (1.4 mMol) of 2-chlorotritylchloride resin (1.4 mMol/g; Barlos et al. *Tetrahedron Lett.* 1989, 30, 3943-3946) was filled into a dried flask. The resin was suspended in $CH_2Cl_2$ (5 ml) and allowed to swell at room temperature under constant shaking for 30 min. A solution of 0.98 mMol (0.7 eq) of the first suitably protected amino acid residue (see below) in $CH_2Cl_2$ (5 ml) completed by 960 µl (4 eq) of diisopropylethylamine (DIEA) was added. After shaking the reaction mixture for 4 hours at 25° C. the resin was filtered off and washed successively with $CH_2Cl_2$ (1×), DMF (1×) and $CH_2Cl_2$ (1×). A solution of $CH_2Cl_2$/MeOH/DIEA (17/2/1, 10 ml) was added to the resin and the suspension was shaken for 30 min. After filtration the resin was washed in the following order with $CH_2Cl_2$ (1×), DMF (1×), $CH_2Cl_2$ (1×), MeOH (1×), $CH_2Cl_2$ (1×), MeOH (1×), $CH_2Cl_2$ (2×), $Et_2O$ (2×) and dried under vacuum for 6 hours.

Loading was typically 0.6-0.7 mMol/g.

The following preloaded resins were prepared: Fmoc-Dab(Boc)O-chlorotrityl resin, Fmoc-AlaO-chlorotrityl resin, Fmoc-Tyr(tBu)O-chlorotrityl resin, Fmoc-ProO-chlorotrityl resin, Fmoc-DProO-chlorotritylresin and Fmoc-Arg(Pbf)O-chlorotrityl resin.

The synthesis was carried out employing a Symphony-peptide synthesizer (Protein Technologies Inc.) using 1-12 reaction vessels. In each vessel 0.2 mMol of the above resin were placed and the resin was swollen in $CH_2Cl_2$ and DMF for 15 min, respectively. The following reaction cycles were programmed and carried out:

| Step | Reagent | Time |
| --- | --- | --- |
| 1 | DMF, wash | 2 × 1.5 min |
| 2 | 20% piperidine/DMF | 1 × 2 min, 1 × 5 min |
| 3 | DMF, wash | 5 × 1.5 min |
| 4a | 3.7 eq Fmoc amino acid/DMF + 3.7 eq HCTU, 7.5 eq DIEA/DMF | 1 × 40 min |
| 5 | DMF, wash | 3 × 1.5 min |
| 6 | 4.4 eq Z-(2Cl)-OSu, 8.7 eq DIEA in NMP/$CH_2Cl_2$ | 1 × 8 min |
| 7 | DMF, wash | 2 × 3 min |

Step 4a was repeated once.

Unless indicated otherwise, the final coupling of an amino acid was followed by a Fmoc deprotection by applying steps 1-3 of the above described reaction cycle.

To introduce an α-hydroxy acid into specific positions within the chain, step 4b was used instead of step 4a:

4b 5 eq α-hydroxy acid

+5 eq HOBt/DMF +5.5 eq DIC 1×6 h

The reaction cycle was finished by skipping steps 6 and 7.

Moreover, if an α-hydroxy acid had been introduced in the previous cycle, step 4a was modified as follows:

4c 5 eq Fmoc amino acid

+0.25 eq DMAP/$CH_2Cl_2$+5.5 eq DIC 1×4 h at 0° C.

Finally, His was always incorporated into the chain by using step 4d instead of 4a:

4d 5 eq Fmoc-His(Trt)-OH+

5 eq HOBt/DMF +5.5 eq DIC 1×6 h

The following side-chain protected α-hydroxy acid derivatives had to be synthesized before their usage in the linear depsipeptide synthesis described above:

N-Boc-protected (2S)-4-amino-2-hydroxybutyric acid was synthesized by a procedure following J. Vizzavona, M. Villain, K. Rose, *Tetrahedron Lett.* 2002, 43, 8693-8696). The synthesis of (2S)-β-(4-[benzyloxy]phenyl)lactic acid was carried out following N. Valls, M. Lopez-Canet, M. Vallribera, J. Bonjoch, *Chem. Eur. J.* 2001, 7, 3446-3460)

Cyclization and Work Up of Backbone Cyclized Depsipeptides

Cleavage of the Fully Protected Depsipeptide Fragment

After completion of the synthesis, the resin (0.2 mMol) was suspended in 5 ml (0.67 mMol, 3.4 eq) of 1% TFA in $CH_2Cl_2$ (v/v) for 3 minutes, filtered, and the filtrate was neutralized with 5 ml (2.92 mMol, 14.6 eq) of 10% DIEA in $CH_2Cl_2$ (v/v). This procedure was repeated three times to ensure completion of the cleavage. The filtrate was evaporated to dryness and a sample of the product was fully deprotected by using a cleavage mixture containing 95% trifluoroacetic acid (TFA), 2.5% water and 2.5% triisopropylsilane (TIS) to be analyzed by reverse phase-HPLC (column $C_{18}$) and ESI-MS to monitor the efficiency of the linear depsipeptide synthesis.

Cyclization of the Linear Depsipeptide

The fully protected linear depsipeptide (0.2 mMol) was dissolved in DMF (4 μMol/ml). Then 152.1 mg (0.4 mMol, 2 eq) of HATU, 54.4 mg (0.4 mMol, 2 eq) of HOAt and 137 μl (0.8 mMol, 4 eq) DIEA were added, and the mixture was vortexed at 25° C. for 16 hours and subsequently concentrated under high vacuum. The residue was partitioned between $CH_2Cl_2$ and $H_2O/CH_3CN$ (90/10: v/v). The $CH_2Cl_2$ phase was evaporated to yield the fully protected cyclic depsipeptide.

Full Deprotection of the Cyclic Depsipeptide

The cyclic depsipeptide obtained was dissolved in 15 ml of the cleavage mixture containing 82.5% trifluoroacetic acid (TFA), 5% water, 5% thioanisole, 5% phenol and 2.5% ethandithiole (EDT). The mixture was allowed to stand at 25° C. for 2.5 hours and thereafter concentrated under vacuum. After precipitation of the cyclic fully deprotected depsipeptide in diethylether ($Et_2O$) at 0° C. the solid was washed twice with $Et_2O$ and dried.

Formation of Disulfide β-Strand Linkage and Purification

After full deprotection, the crude depsipeptide was dissolved in 0.1 M ammonium acetate buffer (1 mg/1 ml, pH=7-8). DMSO (up to 5% by volume) was added and the solution was shaken overnight. Following evaporation the residue was purified by preparative reverse phase HPLC.

Analytical Method 1:

Analytical HPLC retention times (RT, in minutes) were determined using an Acquity UPLC BEH C18 1.7 μm column with the following solvents A ($H_2O/CH_3CN$, 95/5 [v/v], +0.1% TFA) and B ($CH_3CN$+0.09% TFA) and the gradient: 0 min: 99% A, 1% B; 4 min: 35% A, 65% B; 4.05-4.2 min: 5% A, 95% B; 4.25-4.5 min: 99% A, 1% B.

Analytical Method 2:

Analytical HPLC retention times (RT, in minutes) were determined using an Acquity UPLC BEH C18 1.7 μm column with the following solvents A ($H_2O$+0.1% TFA) and B ($CH_3CN$+0.09% TFA) and the gradient: 0 min: 99% A, 1% B; 0.2 min: 99% A, 1% B; 2.5 min: 35% A, 65% B; 2.55-2.7 min:1% A, 99% B; 2.75-3.2 min: 99% A, 1% B.

Examples 1 and 7 are shown in Table 1. The depsipeptides were synthesized starting with the amino acid Dab which was grafted to the resin. Starting resin was Fmoc-Dab(Boc)O-chlorotrityl resin, which was prepared as described above. The linear depsipeptides were synthesized on solid support according to the procedure described above in the following sequence: Resin-Dab(Boc)-P7-P6-P5-P4-P3-P2-P1-Pro-$^D$Pro-P14-P13-P12-P11-P10-P9. Following a final Fmoc deprotection as described above, the depsipeptides were cleaved from the resin, cyclized, deprotected and after formation of the disulfide β-strand linkage purified as indicated above.

HPLC-retention times (minutes) were determined using the gradient method 1 as described above Example 2 is shown in Table 1, too. The depsipeptide was synthesized starting with the amino acid Ala which was grafted to the resin. Starting resin was Fmoc-AlaO-chlorotrityl resin, which was prepared as described above. The linear depsipeptide was synthesized on solid support according to the procedure described above in the following sequence: Resin-Ala-P5-P4-P3-P2-P1-Pro-$^D$Pro-P14-P13-P12-P11-P10-P9-P8-P7. Following a final Fmoc deprotection as described above, the depsipeptide was cleaved from the resin, cyclized, deprotected and after formation of the disulfide β-strand linkage purified as indicated above.

HPLC-retention time (minutes) was determined using the gradient method 2 as described above Example 3 is likewise shown in Table 1. The depsipeptide was synthesized starting with the amino acid Tyr which was grafted to the resin. Starting resin was Fmoc-Tyr(tBu)O-chlorotrityl resin, which was prepared as described above. The linear depsipeptide was synthesized on solid support according to the procedure described above in the following sequence: Resin-Tyr(tBu)-P9-P8-P7-P6-P5-P4-P3-P2-P1-Pro-$^D$Pro-P14-P13-P12-P11. Following a final Fmoc deprotection as described above, the depsipeptide was cleaved from the resin, cyclized, deprotected and after formation of the disulfide β-strand linkage purified as indicated above.

HPLC-retention time (minutes) was determined using the gradient method 1 as described above Examples 4, 6, 8 and 10 are shown in Table 1 as well. The depsipeptides were synthesized starting with the amino acid Pro which was grafted to the resin. Starting resin was Fmoc-ProO-chlorotrityl resin, which was prepared as described above. The linear depsipeptides were synthesized on solid support according to the procedure described above in the following sequence: Resin-Pro-$^D$Pro-P14-P13-P12-P11-P10-P9-P8-P7-P6-PS-P4-P3-P2-P1. Following a final Fmoc deprotection as described above, the depsipeptides were cleaved from the resin, cyclized, deprotected and after formation of the disulfide β-strand linkage purified as indicated above.

HPLC-retention times (minutes) were determined using the gradient method 1 as described above Example 5 is also shown in Table 1. The depsipeptide was synthesized starting with the amino acid $^D$Pro which was grafted to the resin. Starting resin was Fmoc-$^D$ProO-chlorotrityl resin, which was prepared as described above. The linear depsipeptide was synthesized on solid support according to the procedure described above in the following sequence: Resin-$^D$Pro-P14-P13-P12-P11-P10-P9-P8-P7-P6-P5-P4-P3-P2-P1-Pro. Following a final Fmoc deprotection as described above, the depsipeptide was cleaved from the resin, cyclized, deprotected and after formation of the disulfide β-strand linkage purified as indicated above.

HPLC-retention time (minutes) was determined using the gradient method 1 as described above Example 9 is also shown in Table 1. The depsipeptide was synthesized starting with the amino acid Arg which was grafted to the resin. Starting resin was Fmoc-Arg(Pbf)O-chlorotrityl resin, which was prepared as described above. The linear depsipeptide was synthesized on solid support according to the procedure described above in the following sequence: Resin-Arg-P4-P3-P2-P1-Pro-$^D$Pro-P14-P13-P12-P11-P10-P9-P8-P7-P6. Following a final Fmoc deprotection as described above, the depsipeptide was cleaved from the resin, cyclized, deprotected and after formation of the disulfide β-strand linkage purified as indicated above.

HPLC-retention time (minutes) was determined using the gradient method 1 as described above.

TABLE 1

Examples (Ex.)

| Ex. | P1 | P2 | P3 | P4 | P5 | P6 | P7 | P8 | P9 | P10 | P11 | P12 | P13 | P14 | Template | Pur. %[a] | [M+2H]/2 | RT |
|---|---|---|---|---|---|---|---|---|---|---|---|---|---|---|---|---|---|---|
| 1. | Tyr | His | Ala | Cys | Ser | Lac | $^D$Pro | Dab | Arg | Tyr | Cys | Tyr | Gln | Lys | $^D$Pro$^L$Pro | 95 | 933.0 | 1.84 |
| 2. | Tyr | His | Ala | Cys | Ser | Ala | $^D$Pro | Ahb | Arg | Tyr | Cys | Tyr | Gln | Lys | $^D$Pro$^L$Pro | 95 | 932.9 | 1.71 |
| 3. | Tyr | His | Ala | Cys | Ser | Ala | $^D$Pro | Dab | Arg | Tyr | Cys | Hhpp | Gln | Lys | $^D$Pro$^L$Pro | 85 | 932.7 | 1.86 |
| 4. | Tyr | His | Ala | Cys | Ser | Ala | $^D$Pro | Dab | Arg | Tyr | Cys | Tyr | Hhpp | Lys | $^D$Pro$^L$Pro | 95 | 950.8 | 1.92 |
| 5. | Hhpp | His | Ala | Cys | Ser | Ala | $^D$Pro | Dab | Arg | Tyr | Cys | Tyr | Gln | Lys | $^D$Pro$^L$Pro | 85 | 933.4 | 1.69 |
| 6. | Tyr | Ahb | Ala | Cys | Ser | Ala | $^D$Pro | Dab | Arg | Tyr | Cys | Tyr | Gln | Lys | $^D$Pro$^L$Pro | 95 | 914.4 | 1.65 |
| 7. | Tyr | His | Ala | Cys | $^D$Ser | Lac | $^D$Pro | Dab | Arg | Tyr | Cys | Tyr | Gln | Lys | $^D$Pro$^L$Pro | 95 | 933.6 | 1.75 |
| 8. | Tyr | His | Ala | Cys | Arg | Ala | $^D$Pro | Dab | Arg | Tyr | Cys | Tyr | Gln | Ahb | $^D$Pro$^L$Pro | 95 | 954.3 | 1.54 |
| 9. | Tyr | His | Lac | Cys | Arg | Ala | $^D$Pro | Dab | Arg | Tyr | Cys | Tyr | Gln | Lys | $^D$Pro$^L$Pro | 95 | 968.4 | 1.60 |
| 10. | Tyr | His | Ala | Cys | Arg | Ala | $^D$Pro | Dab | Arg | Tyr | Cys | Tyr | $^D$Gln | Ahb | $^D$Pro$^L$Pro | 95 | 954.6 | 1.50 |

Cys in pos. 4 and 11 in Ex. 1-11 form a disulfide bridge,
[a] %-purity of compounds after prep. HPLC.

2. Biological Methods 2.1. Preparation of the Depsipeptides

Lyophilized depsipeptides were weighed on a Microbalance (Mettler MT5) and dissolved in sterile water to a final concentration of 1 mM or dissolved in DMSO to a final concentration of 10 mM. Stock solutions were kept at +4° C., light protected. In case of DMSO stock solutions the biological assays were carried out under assay conditions having less than 1% DMSO.

2.2. Cell Culture

Mouse pre-B cells were cultured in RPMI1640 plus 5% FBS, antibiotic/antimycotic, non essential amino acid, 50 µM β-mercaptoethanol and 1 mM natrium pyruvate. HELA cells were maintained in RPMI1640 plus 10% FBS, pen/strept and 2 mM L-glutamine. Cos-7 cells were grown in DMEM medium with 4500 mg/mL glucose supplemented with 10% FCS, pen/strept and 2 mM L-glutamine. All cell lines were grown at 37° C. at 5% $CO_2$. Cell media, media supplements, PBS-buffer, HEPES, antibiotic/antimycotic, pen/strept, non essential amino acid, L-glutamine, β-mercaptoethanol and sera were purchased from Gibco (Pailsey, UK). All fine chemicals were supplied by Merck (Darmstadt, Germany).

2.3. $Ca^{2+}$-Assay: CXCR4-Antagonizing Activity of the Depsipeptides

Increases in intracellular calcium were monitored using a Flexstation 384 (Molecular Devices, Sunnyvale, Calif.) to assay the depsipeptides for CXCR4 antagonism in a mouse pre-B cell line 300-19 stably transfected with human CXCR4 (E. Oberlin, A. Amara, F. Bachelerie, C. Bessia, J.-L. Virelizier, F. Arenzana-Seisdedos, O. Schwartz, J.-M. Heard, I. Clark-Lewis, D. F. Legler, M. Loetscher, M. Baggiolini, B. Moser, Nature 1996, 382, 833-835; M. Loetscher, T. Geiser, T. O'Reilly, R. Zwalen, M. Baggiolini, B. Moser, J. Biol. Chem. 1994, 269, 232-237; M. D'Apuuo, A. Rolink, M. Loetscher, J. A. Hoxie, I. Clark-Lewis, F. Melchors, M. Baggiolini, B. Moser, Eur. J. Immunol. 1997, 27, 1788-1793). The cells were batch loaded with the Calcium 4 Assay kit (Molecular Devices) in assay buffer (Hanks Balanced salt solution [HBSS], 20 mM HEPES, pH 7.4, 0.1% BSA) for 1 h at room temperature and labeled cells were dispensed into black well assays plates (Costar No. 3603). Calcium mobilization induced by stromal-derived factor-1 (SDF-1) was measured in the Flexstation 384 (excitation: 485 nm; emission: 525 nm) for 90 seconds. Antagonist activity of depsipeptides was determined by spiking the cells with compounds prior to SDF-1 addition. Dose response curves (compound concentration versus % maximum response for SDF-1) were determined for each antagonist and $IC_{50}$ values were calculated by fitting the data to a four parameter logistic equation using SoftmaxPro 4.8 (Molecular Devices).

2.4. Cytotoxicity Assay

The cytotoxicity of the depsipeptides to HELA cells (Acc57) and COS-7 cells (CRL-1651) was determined using the MTT reduction assay (T. Mossman, J. Immunol. Meth. 1983, 65, 55-63; M. V. Berridge, A. S. Tan, Arch. Biochem. Biophys. 1993, 303, 474-482). Briefly, the method was as follows: 7000 HELA cells/well and 4500 COS-7 cells/well were seeded and grown in 96-well microtiter plates for 24 h at 37° C. at 5% $CO_2$. Thereafter, time zero (Tz) was determined by MTT reduction (see below). The supernatant of the remaining wells was discarded, and fresh medium and compounds in serial dilutions (12.5, 25 and 50 µM, triplicates) were pipetted into the wells. After incubation of the cells for 48 h at 37° C. at 5% $CO_2$ the supernatant was discarded again and 100 µL MTT reagent (0.5 mg/mL in RPMI1640 and DMEM, respectively)/well was added. Following incubation at 37° C. for 2 h the media were aspirated and the cells were spiked (100 µL isopropanol/well). The absorbance of the solubilized formazan was measured at 595 nm ($OD_{595}$peptide). For each concentration averages were calculated from triplicates. The percentage of growth was calculated as follows: ($OD_{595}$peptide-$OD_{595}$Tz-$OD_{595}$Empty well)/($OD_{595}$Tz-$OD_{595}$Empty well)×100%. The $GI_{50}$ (Growth Inhibition) concentrations were calculated for each depsipeptide by using a trend line function for the concentrations (50, 25, 12.5 and 0 µM), the corresponding percentages and the value 50, (=TREND ($C_{50}$:$C_0$, %$_{50}$:%$_0$, 50).

2.5. Hemolysis

The depsipeptides were tested for their hemolytic activity against human red blood cells (hRBC). Fresh hRBC were washed three times with phosphate buffered saline (PBS) and centrifuged for 10 min at 2000×g. Compounds (100 µM) were incubated with 20% hRBC (v/v) for 1 h at 37° C. The final erythrocyte concentration was approximately $0.9×10^9$ cells/mL. A value of 0% and 100% cell lyses, respectively, was determined by incubation of hRBC in the presence of PBS alone and 0.1% Triton X-100 in $H_2O$, respectively. The samples were centrifuged, the supernatants were 20-fold diluted in PBS buffer and the optical densities (OD) were measured at 540 nm. The 100% lyses value ($OD_{540}H_2O$) gave an $OD_{540}$ of approximately 1.3-1.8.

Percent hemolysis was calculated as follows: ($OD_{540}$peptide/$OD_{540}H_2O$)×100%.

2.6. Plasma Stability

The stability of the depsipeptides in human and mouse plasma was determined by applying the following method: 315 µL/deep well of freshly thawed human plasma (Basler Blutspende-dienst) and mouse plasma (Harlan Sera-Lab, UK), respectively, were spiked with 35 μL/well of compound in PBS (100 μM, triplicate) and incubated at 37° C. At t=0, 15, 30, 60, 120 and 240 min aliquots of 50 μL were transferred to filtration plate wells containing 150 μL/well of acetonitrile. Following shaking for 2 min the occurred suspensions were filtrated by vacuum and finally, 100 μL of each filtrate were transferred to a propylene microtiter plate, and analyzed by LC/MS as follows: Column: Waters, XBridge C18, mobile phases: (A) water+0.1% formic acid and (B) acetonitrile/water, 95/5 (v/v)+0.1% formic acid, gradient: 5%-100% (B) in 2 minutes, electrospray ionization, MRM detection (triple quadrupole). The peak areas were determined and triplicate values are averaged. The stability is expressed in percent of the initial value at t=0. ($t_x/t_0 \times 100$). By using the TREND function of EXCEL (Microsoft Office 2003) $T_{1/2}$ were determined.

TABLE 2

| Ex. | IC50% [nM] ± SD, CXCR4 receptor |
|---|---|
| 1 | 0.8 ± 0.5 |
| 2 | 0.7 ± 0.7 |
| 3 | 2.7 ± 1.4 |
| 4 | 4.4 ± 1.6 |
| 5 | 3.3 ± 1.1 |
| 6 | 13.5 ± 5 |
| 7 | 2.1 ± 0.5 |
| 8 | 82.4 ± 12.8 |
| 9 | 20.8 ± 8.3 |
| 10 | 16.6 ± 1.5 |

TABLE 3

| | Cytotoxicity | | | Plasmastability | |
|---|---|---|---|---|---|
| | Hela Cells | Cos-7 Cells | Hemolysis | | |
| Ex. | GI$_{50}$ [μM] | GI$_{50}$ [μM] | at 100 μM [%] | human pl. T$_{1/2}$ [min] | mouse pl. T$_{1/2}$ [min] |
| 1 | 2 | 12 | 0.2 | 79 | 73 |
| 2 | >50 | >50 | 0.7 | 240 | 240 |
| 3 | >50 | >50 | 0.4 | 81 | 136 |
| 4 | >50 | >50 | 1.0 | 240 | 240 |
| 5 | >50 | >50 | 1.5 | 240 | 240 |
| 6 | >50 | >50 | 1.0 | 4.2 | 4.3 |
| 7 | >50 | >50 | 0.2 | 62 | 51 |
| 8 | >50 | >50 | 0.4 | 0 | 0 |
| 9 | >50 | >50 | 0.4 | 85 | 74 |
| 10 | >50 | >50 | 0.3 | 5.1 | 5.3 |

The invention claimed is:

1. A compound of the general formulae

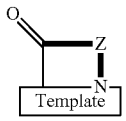

(Ia)

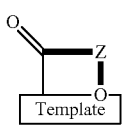

(Ib)

wherein

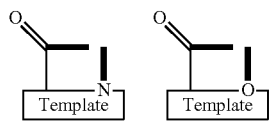

are groups of one of the formulae

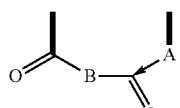

(a1)

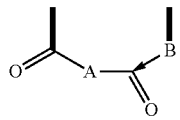

(a2)

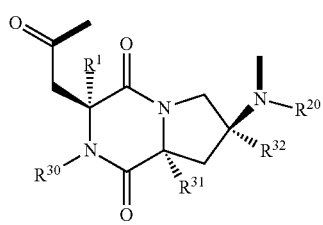

(b1)

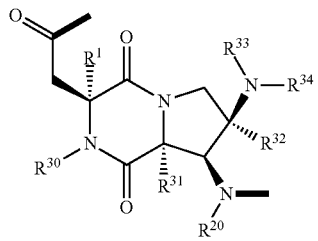

(b2)

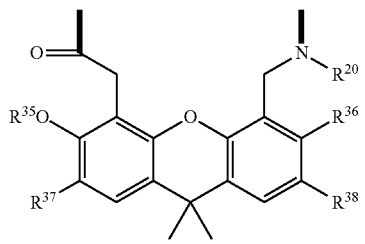

(c1)

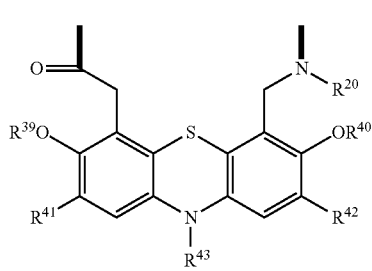

(c2)

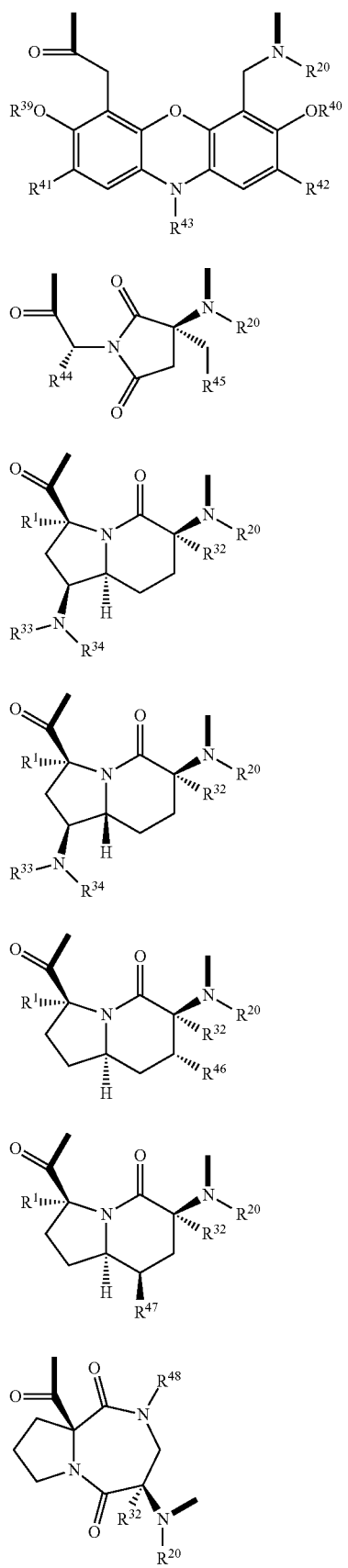
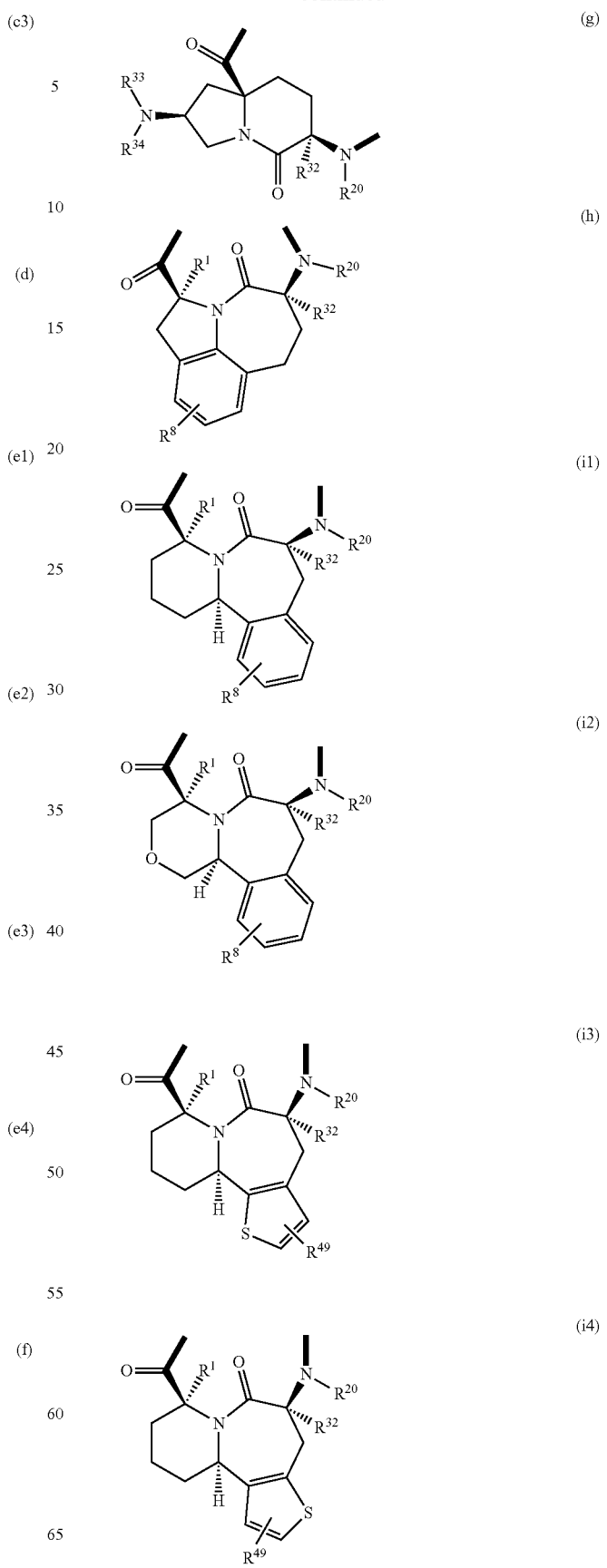

-continued (j) 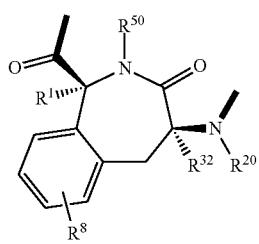

(k) 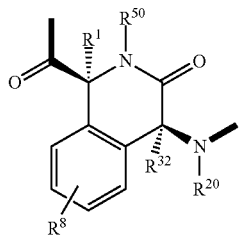

(l) 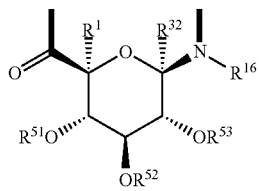

(m) 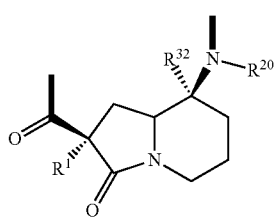

(n) 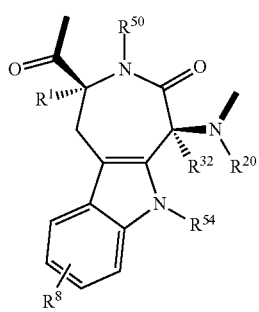

(o) 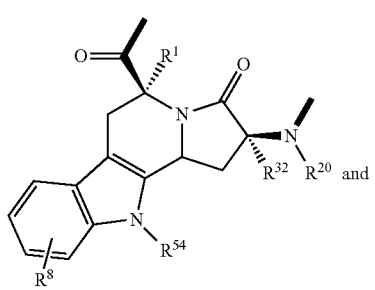

-continued (p) 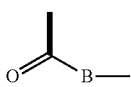

wherein

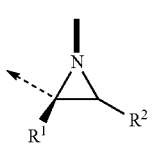

is Gly or Glycolic acid residue, or the residue of an L-α-amino acid with B being a residue of formula —NR20CH(R71)-, or —NR20CH(R72)-, or —NR20CH(R73)- or —NR20CH(R74)- or —NR20OCH(R84)- or the residue of an L-α-hydroxy acid with B being a residue of formula —OCH(R71)- or —OCH(R72)- or —OCH(R73)- or —OCH(R74)- or —OCH(R84)-, or the enantiomer of one of the groups A1 to A69 and A105, or the enantiomer of the groups A106 to A110 as defined hereinafter;

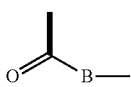

is a group of one of the formulae

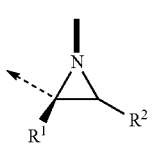 A1

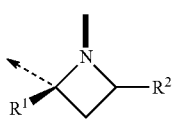 A2

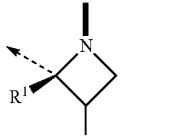 A3

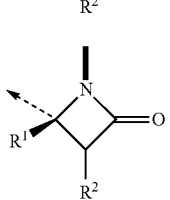 A4

-continued
A5 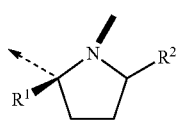
A6 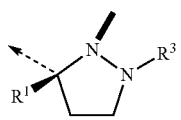
A7 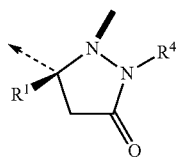
A8 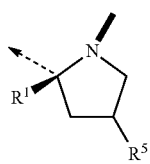
A9 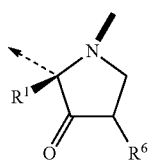
A10 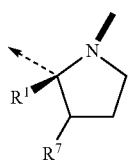
A11 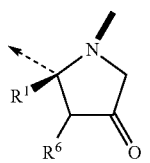
A12 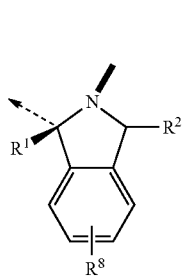
A13 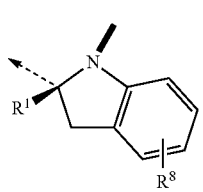
-continued
A14 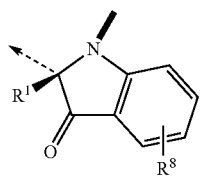
A15 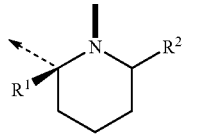
A16 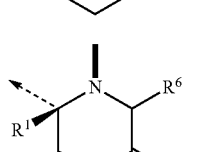
A17 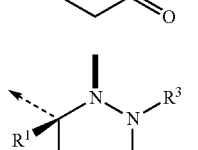
A18 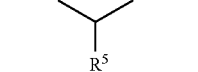
A19 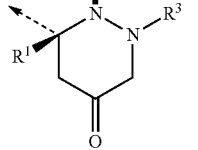
A20 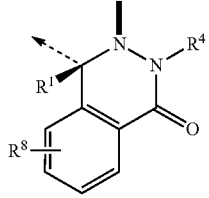
A21 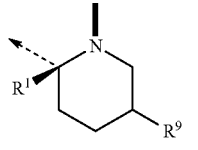
A22 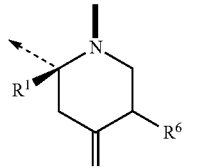

-continued
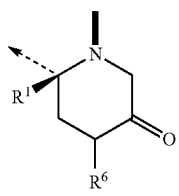
A23
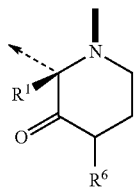
A24
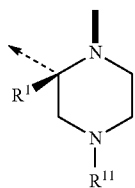
A25
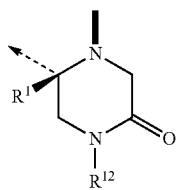
A26
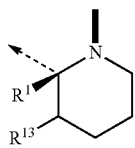
A27
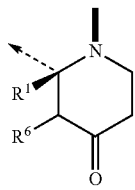
A28
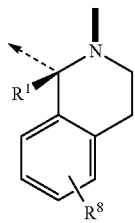
A29
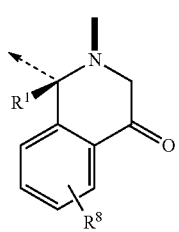
A30
-continued
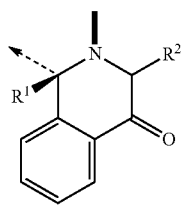
A31
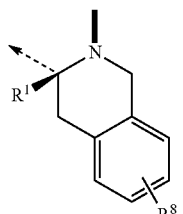
A32
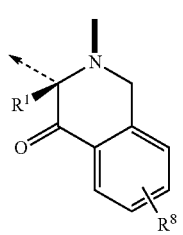
A33
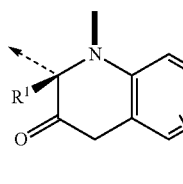
A34
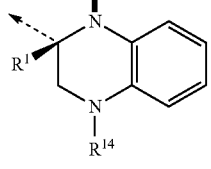
A35
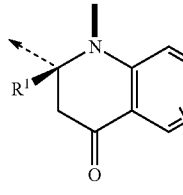
A36
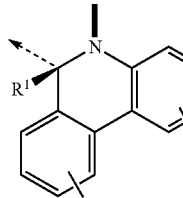
A37
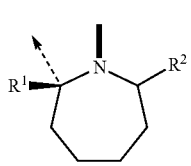
A38

-continued
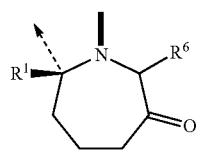
A39
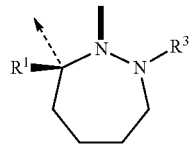
A40
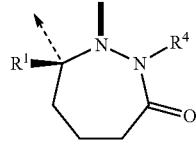
A41
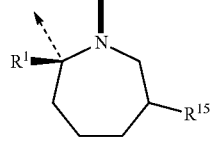
A42
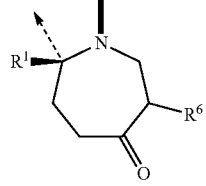
A43
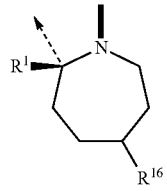
A44
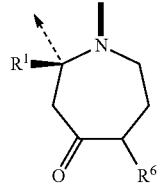
A45
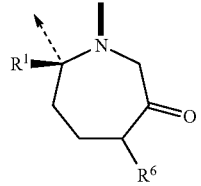
A46
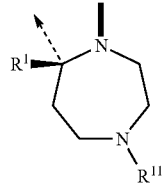
A47
-continued
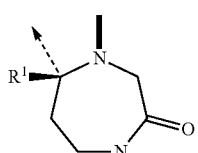
A48
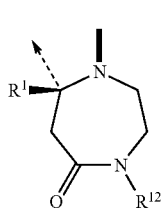
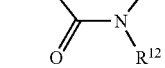
A49
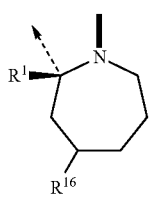
A50
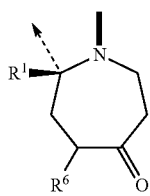
A51
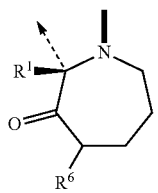
A52
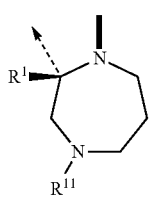
A53
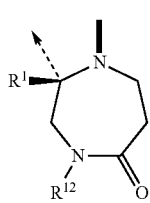
A54
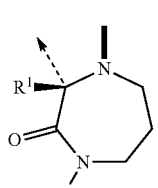
A55

-continued
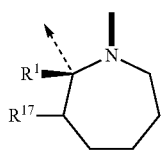
A56
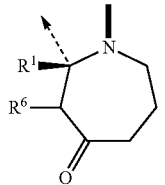
A57
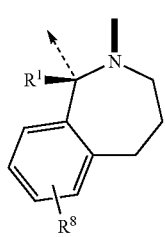
A58
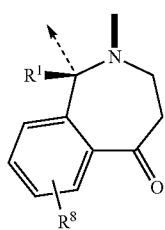
A59
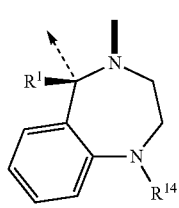
A60
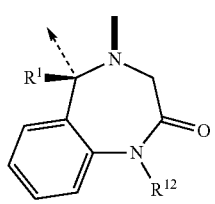
A61
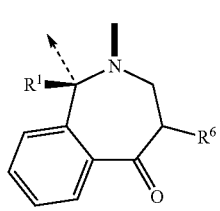
A62
-continued
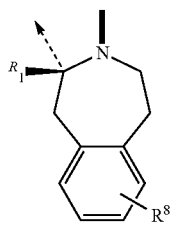
A63
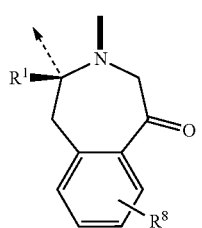
A64
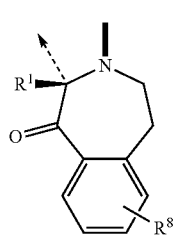
A65
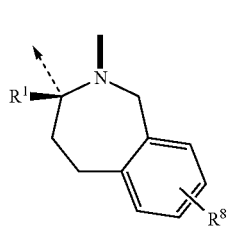
A66
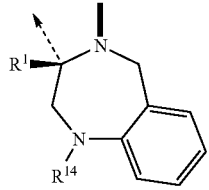
A67
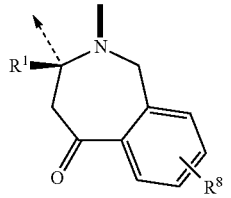
A68
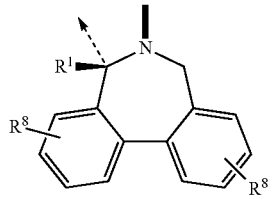
A69

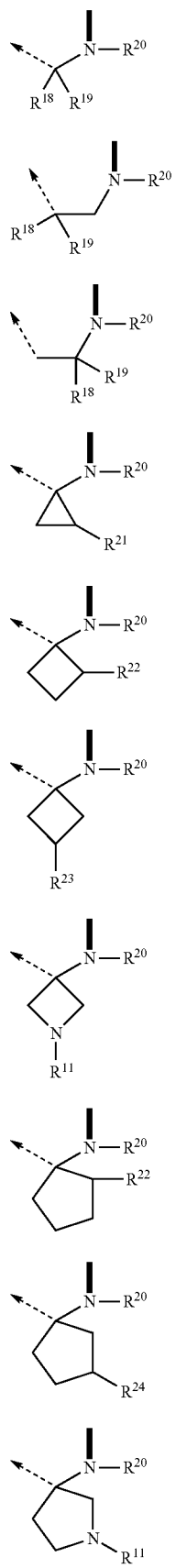
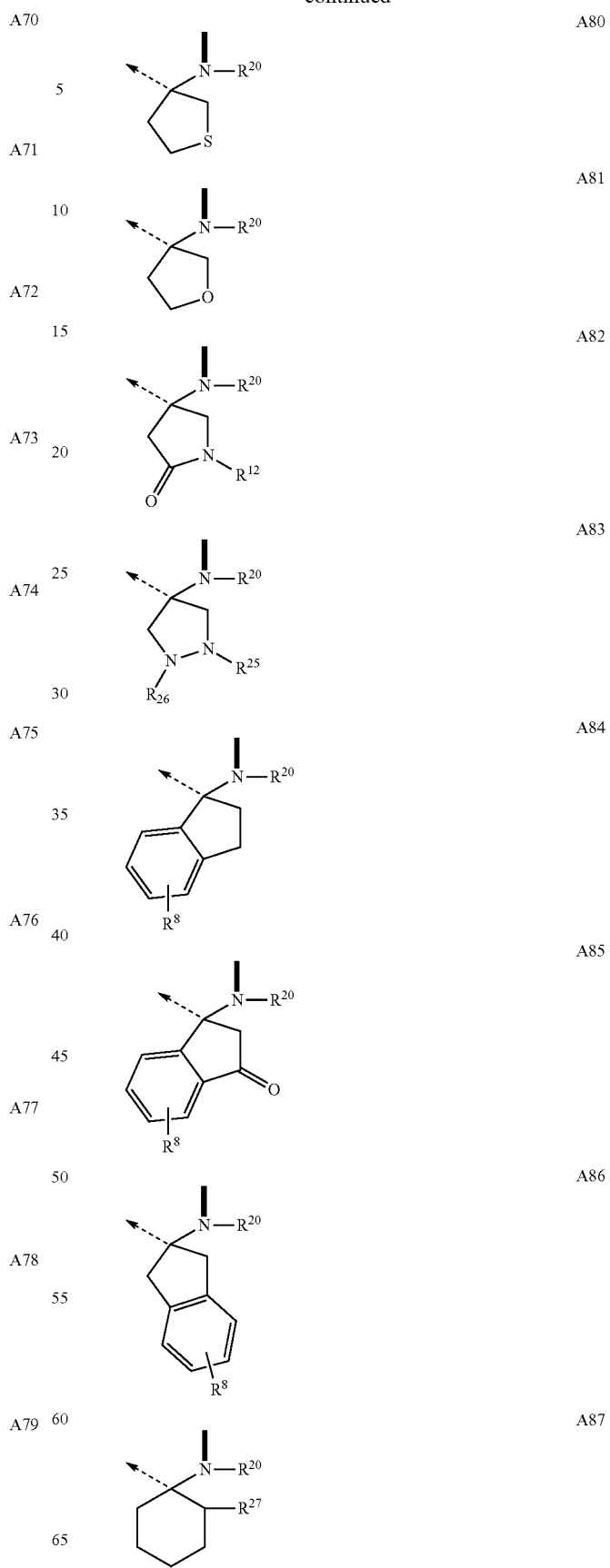

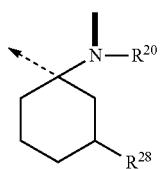 A88
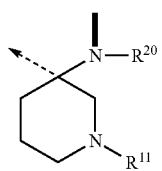 A89
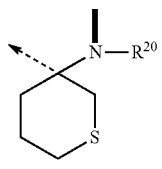 A90
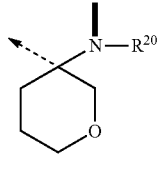 A91
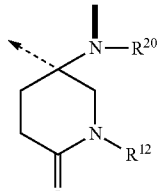 A92
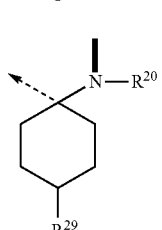 A93
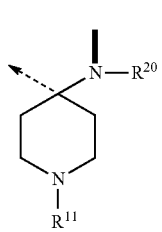 A94
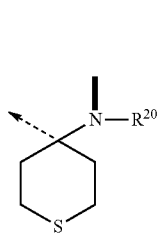 A95
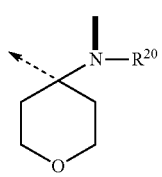 A96
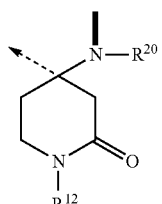 A97
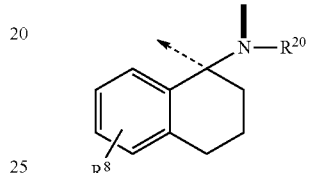 A98
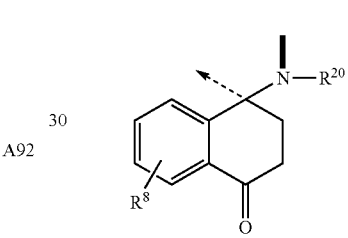 A99
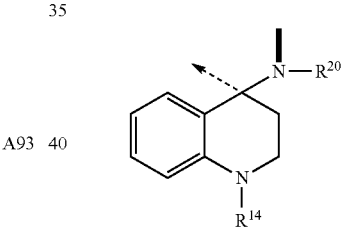 A100
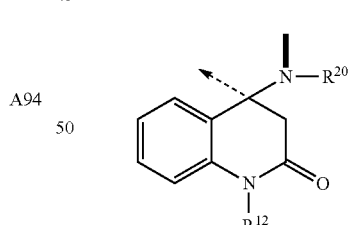 A101
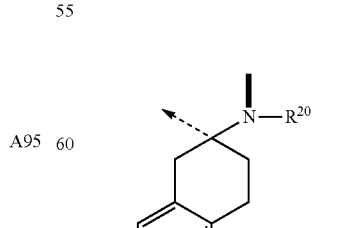 A102
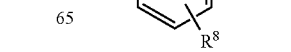

-continued

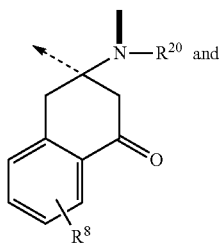
A103

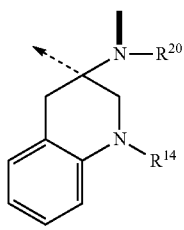
A104

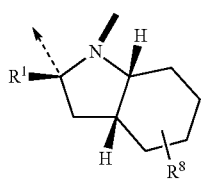
A105

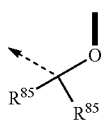
A106

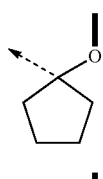
A107

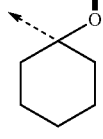
A108

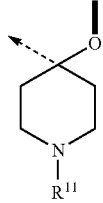
A109

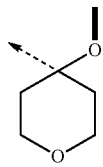
A110

R1 is H; lower alkyl; or aryl-lower alkyl;
R2 is H; alkyl; alkenyl; —(CH2)m(CHR61)sOR55; —(CH2)m(CHR61)sSR56; —(CH2)m(CHR61)s NR33R34; —(CH2)m(CHR61)sOCONR33R75; —(CH2)m(CHR61)sNR20CONR33R82; —(CH2)o (CHR61)sCOOR57; —(CH2)o (CHR61)sCONR58R59; —(CH2)o(CHR61)sPO (OR60)2; —(CH2)o(CHR61)sSO2R62; or —(CH2)o (CHR61)sR77;

R3 is H; alkyl; alkenyl; —(CH2)m(CHR61)sOR55; —(CH2)m(CHR61)sSR56; —(CH2)m(CHR61)s NR33R34; —(CH2)m(CHR61)sOCONR33R75; —(CH2)m(CHR61)sNR20CONR33R82; —(CH2)o (CHR61)sCOOR57; —(CH2)o(CHR61)s CONR58R59; —(CH2)o(CHR61)sPO(OR60)2; —(CH2)o(CHR61)sSO2R62; or —(CH2)o (CHR61)sC6H4R8;

R4 is H; alkyl; alkenyl; —(CH2)m(CHR61)sOR55; —(CH2)m(CHR61)sSR56; —(CH2)m(CHR61)s NR33R34; —(CH2)m(CHR61)sOCONR33R75; —(CH2)m(CHR61)sNR2OCONR33R82; —(CH2)p (CHR61)sCOOR57; —(CH2)p(CHR61)s CONR58R59; —(CH2)p(CHR61)sPO(OR60)2; —(CH2)p(CHR61)sSO2R62; or —(CH2)o (CHR61)sC6H4R8;

R5 is alkyl; alkenyl; —(CH2)o(CHR61)sOR55; —(CH2)o(CHR61)sSR56; —(CH2)o(CHR61)s NR33R34; —(CH2)o(CHR61)sOCONR33R75; —(CH2)o(CHR61)sNR20CONR33R82; —(CH2)o (CHR61)sCOOR57; —(CH2)o(CHR61)s CONR58R59; —(CH2)o(CHR61)sPO(OR60)2; —(CH2)o(CHR61)sSO2R62; or —(CH2)o (CHR61)sC6H4R8;

R6 is H; alkyl; alkenyl; —(CH2)o(CHR61)sOR55; —(CH2)o(CHR61)sSR56; —(CH2)o(CHR61)s NR33R34; —(CH2)o(CHR61)sOCONR33R75; —(CH2)o(CHR61)sNR20CONR33R82; —(CH2)o (CHR61)sCOOR57; —(CH2)o(CHR61)s CONR58R59; —(CH2)o(CHR61)sPO(OR60)2; —(CH2)o(CHR61)sSO2R62; or —(CH2)o (CHR61)sC6H4R8;

R7 is alkyl; alkenyl; —(CH2)q(CHR61)sOR55; —(CH2)q(CHR61)sNR33R34; —(CH2)q(CHR61)s OCONR33R75; —(CH2)q(CHR61)s NR20CONR33R82; —(CH2)r(CHR61)sCOOR57; —(CH2)r(CHR61)sCONR58R59; —(CH2)r (CHR61)sPO(OR60)2; —(CH2)r(CHR61)sSO2R62; or —(CH2)r(CHR61)sC6H4R8;

R8 is H; Cl; F; CF3; NO2; lower alkyl; lower alkenyl; aryl; aryl-lower alkyl; —(CH2)o(CHR61)sR77-(CH2)o (CHR61)sOR55; —(CH2)o(CHR61)sSR56; —(CH2)o (CHR61)NR33R34-(CH2)o(CHR61)sOCONR33R75; —(CH2)o(CHR61)sNR20CONR33R82; —(CH2)o (CHR61)sCOOR57; —(CH2)o(CHR61)s CONR58R59; —(CH2)o(CHR61)sPO(OR60)2; —(CH2)o(CHR61)sSO2R62; or —(CH2)o (CHR61)sCOR64;

R9 is alkyl; alkenyl; —(CH2)o(CHR61)sOR55; —(CH2)o(CHR61)sSR56; —(CH2)o(CHR61)s NR33R34; —(CH2)o(CHR61)sOCONR33R75; —(CH2)o(CHR61)sNR20CONR33R82; —(CH2)o (CHR61)sCOOR57; —(CH2)o(CHR61)s CONR58R59; —(CH2)o(CHR61)sPO(OR60)2; —(CH2)o(CHR61)s SO2R62; or —(CH2)o (CHR61)sC6H4R8;

R10 is alkyl; alkenyl; —(CH2)o(CHR61)sOR55; —(CH2)o(CHR61)sSR56; —(CH2)o(CHR61)s NR33R34; —(CH2)o(CHR61)sOCONR33R75; —(CH2)o (CHR61)sNR20CONR33R82; —(CH2)o (CHR61)sCOOR57; —(CH2)o(CHR61)s CONR58R59; —(CH2)o(CHR61)sPO(OR60)2; —(CH2)o(CHR61)sSO2R62; or —(CH2)o(CHR61)sC6H4R8;

R11 is H; alkyl; alkenyl; —(CH2)m(CHR61)sOR55; —(CH2)m(CHR61)sNR33R34; —(CH2)m(CHR61)sOCONR33R75; —(CH2)m(CHR61)sNR20CONR33R82; —(CH2)o(CHR61)sCOOR57; —(CH2)o(CHR61)sCONR58R59; —(CH2)o(CHR61)sPO(OR60)2; —(CH2)o(CHR61)sSO2R62; or —(CH2)o(CHR61)s C6H4R8;

R12 is H; alkyl; alkenyl; —(CH2)m(CHR61)sOR55; —(CH2)m(CHR61)sSR56; —(CH2)m(CHR61)sNR33R34; —(CH2)m(CHR61)sOCONR33R75; —(CH2)m(CHR61)sNR20CONR33R82; —(CH2)r(CHR61)sCOOR57; —(CH2)r(CHR61)sCONR58R59; —(CH2)r(CHR61)sPO(OR60)2; —(CH2)r(CHR61)s SO2R62; or —(CH2)r(CHR61)sC6H4R8;

R13 is alkyl; alkenyl; —(CH2)q(CHR61)sOR55; —(CH2)q(CHR61)sSR56; —(CH2)q(CHR61)sNR33R34; —(CH2)q(CHR61)sOCONR33R75; —(CH2)q(CHR61)sNR20CONR33R82; —(CH2)q(CHR61)sCOOR57; —(CH2)q(CHR61)sCONR58R59; —(CH2)q(CHR61)sPO(OR60)2; —(CH2)q(CHR61)s SO2R62; or —(CH2)q(CHR61)sC6H4R8;

R14 is H; alkyl; alkenyl; —(CH2)m(CHR61)sOR55; —(CH2)m(CHR61)sNR33R34; —(CH2)m(CHR61)sOCONR33R75; —(CH2)m(CHR61)sNR20CONR33R82; —(CH2)q(CHR61)sCOOR57; —(CH2)q(CHR61)sCONR58R59; —(CH2)q(CHR61)sPO(OR60)2; —(CH2)q(CHR61)sSOR62; or —(CH2)q(CHR61)s C6H4R8;

R15 is alkyl; alkenyl; —(CH2)o(CHR61)sOR55; —(CH2)o(CHR61)sSR56; —(CH2)o(CHR61)sNR33R34; —(CH2)o(CHR61)sOCONR33R75; —(CH2)o(CHR61)sNR20CONR33R82; —(CH2)o(CHR61)sCOOR57; —(CH2)o(CHR61)sCONR58R59; —(CH2)o(CHR61)sPO(OR60)2; —(CH2)o(CHR61)s SO2R62; or —(CH2)o(CHR61)sC6H4R8;

R16 is alkyl; alkenyl; —(CH2)o(CHR61)sOR55; —(CH2)o(CHR61)sSR56; —(CH2)o(CHR61)sNR33R34; —(CH2)o(CHR61)sOCONR33R75; —(CH2)o(CHR61)sNR20CONR33R82; —(CH2)o(CHR61)sCOOR57; —(CH2)o(CHR61)sCONR58R59; —(CH2)o(CHR61)sPO(OR60)2; —(CH2)o(CHR61)s SO2R62; or —(CH2)o(CHR61)sC6H4R8;

R17 is alkyl; alkenyl; —(CH2)q(CHR61)sOR55; —(CH2)q(CHR61)sSR56; —(CH2)q(CHR61)sNR33R34; —(CH2)q(CHR61)sOCONR33R75; —(CH2)q(CHR61)sNR20CONR33R82; —(CH2)q(CHR61)sCOOR57; —(CH2)q(CHR61)sCONR58R59; —(CH2)q(CHR61)sPO(OR60)2; —(CH2)q(CHR61)s SO2R62; or —(CH2)q(CHR61)sC6H4R8;

R18 is alkyl; alkenyl; —(CH2)p(CHR61)sOR55; —(CH2)p(CHR61)sSR56; —(CH2)p(CHR61)sNR33R34; —(CH2)p(CHR61)sOCONR33R75; —(CH2)p(CHR61)sNR20CONR33R82; —(CH2)p(CHR61)sCOOR57; —(CH2)p(CHR61)sCONR58R59; —(CH2)p(CHR61)sPO(OR60)2; —(CH2)p(CHR61)s SO2R62; or —(CH2)o(CHR61)sC6H4R8;

R19 is lower alkyl; —(CH2)p(CHR61)sOR55; —(CH2)p(CHR61)sSR56; —(CH2)p(CHR61)sNR33R34; —(CH2)p(CHR61)sOCONR33R75; —(CH2)p(CHR61)sNR20CONR33R82; —(CH2)p(CHR61)sCOOR57; —(CH2)p(CHR61)sCONR58R59; —(CH2)p(CHR61)sPO(OR60)2; —(CH2)p(CHR61)sSO2R62; or —(CH2)o(CHR61)sC6H4R8; or R18 and R19 taken together can form: —(CH2)2-6-; —(CH2)2O(CH2)2-; —(CH2)2S(CH2)2-; or —(CH2)2NR57(CH2)2-;

R20 is H; alkyl; alkenyl; or aryl-lower alkyl;

R21 is H; alkyl; alkenyl; —(CH2)o(CHR61)sOR55; —(CH2)o(CHR61)sSR56; —(CH2)o(CHR61)sNR33R34; —(CH2)o(CHR61)sOCONR33R75; —(CH2)o(CHR61)sNR20CONR33R82; —(CH2)o(CHR61)sCOOR57; —(CH2)o(CHR61)sCONR58R59; —(CH2)o(CHR61)sPO(OR60)2; —(CH2)o(CHR61)s SO2R62; or —(CH2)o(CHR61)sC6H4R8;

R22 is H; alkyl; alkenyl; —(CH2)o(CHR61)sOR55; —(CH2)o(CHR61)sSR56; —(CH2)o(CHR61)sNR33R34; —(CH2)o(CHR61)sOCONR33R75; —(CH2)o(CHR61)sNR20CONR33R82; —(CH2)o(CHR61)sCOOR57; —(CH2)o(CHR61)sCONR58R59; —(CH2)o(CHR61)sPO(OR60)2; —(CH2)o(CHR61)s SO2R62; or —(CH2)o(CHR61)sC6H4R8;

R23 is alkyl; alkenyl; —(CH2)o(CHR61)sOR55; —(CH2)o(CHR61)sSR56; —(CH2)o(CHR61)sNR33R34; —(CH2)o(CHR61)sOCONR33R75; —(CH2)o(CHR61)sNR20CONR33R82; —(CH2)o(CHR61)sCOOR57; —(CH2)o(CHR61)sCONR58R59; —(CH2)o(CHR61)sPO(OR60)2; —(CH2)o(CHR61)s SO2R62; or —(CH2)o(CHR61)sC6H4R8;

R24 is alkyl; alkenyl; —(CH2)o(CHR61)sOR55; —(CH2)o(CHR61)sSR56; —(CH2)o(CHR61)sNR33R34; —(CH2)o(CHR61)sOCONR33R75; —(CH2)o(CHR61)sNR20CONR33R82; —(CH2)o(CHR61)sCOOR57; —(CH2)o(CHR61)sCONR58R59; —(CH2)o(CHR61)sPO(OR60)2; —(CH2)o(CHR61)s SO2R62; or —(CH2)o(CHR61)sC6H4R8;

R25 is H; alkyl; alkenyl; —(CH2)m(CHR61)sOR55; —(CH2)m(CHR61)sSR56; —(CH2)m(CHR61)sNR33R34; —(CH2)m(CHR61)sOCONR33R75; —(CH2)m(CHR61)sNR20CONR33R82; —(CH2)o(CHR61)sCOOR57; —(CH2)o(CHR61)sCONR58R59; —(CH2)o(CHR61)sPO(OR60)2; —(CH2)o(CHR61)sSO2R62; or —(CH2)o(CHR61)sC6H4R8;

R26 is H; alkyl; alkenyl; —(CH2)m(CHR61)sOR55; —(CH2)m(CHR61)sSR56; —(CH2)m(CHR61)sNR33R34; —(CH2)m(CHR61)sOCONR33R75; —(CH2)m(CHR61)sNR20CONR33R82; —(CH2)o(CHR61)sCOOR57; —(CH2)o(CHR61)sCONR58R59; —(CH2)o(CHR61)sPO(OR60)2; —(CH2)o(CHR61)s SO2R62; or —(CH2)o(CHR61)sC6H4R8; or R25 and R26 taken together can form: —(CH2)2-6-; —(CH2)rO(CH2)r; —(CH2)rS(CH2)r-; or —(CH2)rNR57(CH2)r-;

R27 is H; alkyl; alkenyl; —(CH2)o(CHR61)sOR55; —(CH2)o(CHR61)sSR56; —(CH2)o(CHR61)sNR33R34; —(CH2)o(CHR61)sCOOR57; —(CH2)o(CHR61)sCONR58R59; —(CH2)o(CHR61)s OCONR33R75; —(CH2)o(CHR61)sNR20CONR33R82; —(CH2)o(CHR61)sPO(OR60)2; —(CH2)o(CHR61)s SO2R62; or —(CH2)o(CHR61)sC6H4R8;

R28 is alkyl; alkenyl; —(CH2)o(CHR61)s-OR55; —(CH2)o(CHR61)s SR56; —(CH2)o(CHR61)sNR33R34; —(CH2)o(CHR61)sOCONR33R75; —(CH2)o(CHR61)sNR20CONR33R82; —(CH2)o(CHR61)s COOR57; —(CH2)o(CHR61)sCONR58R59; —(CH2)o(CHR61)s PO(OR60)2; —(CH2)o(CHR61)s SO2R62; or —(CH2)o(CHR61)sC6H4R8;

R29 is alkyl; alkenyl; —(CH2)o(CHR61)sOR55; —(CH2)o(CHR61)sSR56; —(CH2)o(CHR61)sNR33R34; —(CH2)o(CHR61)sOCONR33R75; —(CH2)o(CHR61)sNR20CONR33R82; —(CH2)o(CHR61)sCOOR57; —(CH2)o(CHR61)sCONR58R59; —(CH2)o(CHR61)sPO(OR60)2; —(CH2)o(CHR61)s SO2R62; or —(CH2)o(CHR61)sC6H4R8;

R30 is H; alkyl; alkenyl; or aryl-lower alkyl;

R31 is H; alkyl; alkenyl; —(CH2)p(CHR61)sOR55; —(CH2)p(CHR61)sNR33R34; —(CH2)p(CHR61)sOCONR33R75; —(CH2)p(CHR61)sNR20CONR33R82; —(CH2)o(CHR61)sCOOR57; —(CH2)o(CHR61)sCONR58R59; —(CH2)o(CHR61)sPO(OR60)2; —(CH2)o(CHR61)sSO2R62; or —(CH2)o(CHR61)s C$_6$H$_4$R8;

R32 is H; lower alkyl; or aryl-lower alkyl;

R33 is H; alkyl, alkenyl; —(CH2)m(CHR61)sOR55; —(CH2)m(CHR61)sNR34R63; —(CH2)m(CHR61)sOCONR75R82; —(CH2)m(CHR61)sNR20CONR78R82; —(CH2)o(CHR61)sCOR64; —(CH2)o(CHR61)s—CONR58R59, —(CH2)o(CHR61)sPO(OR60)2; —(CH2)o(CHR61)s SO2R62; or —(CH2)o(CHR61)sC6H4R8;

R34 is H; lower alkyl; aryl, or aryl-lower alkyl; or

R33 and R34 taken together can form: —(CH2)2-6-; —(CH2)2-0(CH2)2-; —(CH2)2S(CH2)2-; or —(CH2)2NR57(CH2)2-;

R35 is H; alkyl; alkenyl; —(CH2)m(CHR61)sOR55; —(CH2)m(CHR61)sNR33R34; —(CH2)m(CHR61)sOCONR33R75; —(CH2)m(CHR61)sNR20CONR33R82; —(CH2)p(CHR61)sCOOR57; —(CH2)p(CHR61)sCONR58R59; —(CH2)p(CHR61)sPO(OR60)2; —(CH2)p(CHR61)sSO2R62; or —(CH2)p(CHR61)s C6H4R8;

R36 is H, alkyl; alkenyl; —(CH2)o(CHR61)sOR55; —(CH2)p(CHR61)sNR33R34; —(CH2)p(CHR61)sOCONR33R75; —(CH2)p(CHR61)sNR20CONR33R82; —(CH2)p(CHR61)sCOOR57; —(CH2)p(CHR61)sCONR58R59; —(CH2)p(CHR61)sPO(OR60)2; —(CH2)p(CHR61)sSO2R62; or —(CH2)o(CHR61)s C6H4R8;

R37 is H; F; Br; Cl; NO2; CF3; lower alkyl; —(CH2)p(CHR61)sOR55; —(CH2)p(CHR61)sNR33R34; —(CH2)p(CHR61)sOCONR33R75; —(CH2)p(CHR61)sNR20CONR33R82; —(CH2)o(CHR61)sCOOR57; —(CH2)o(CHR61)sCONR58R59; —(CH2)o(CHR61)sPO(OR60)2; —(CH2)o(CHR61)sSO2R62; or —(CH2)o(CHR61)s C6H4R8;

R38 is H; F; Br; Cl; NO2; CF3; alkyl; alkenyl; —(CH2)p(CHR61)sOR55; —(CH2)p(CHR61)sNR33R34; —(CH2)p(CHR61)sOCONR33R75; —(CH2)p(CHR61)sNR20CONR33R82; —(CH2)o(CHR61)sCOOR57; —(CH2)o(CHR61)sCONR58R59; —(CH2)o(CHR61)sPO(OR60)2; —(CH2)o(CHR61)sSO2R62; or —(CH2)o(CHR61)sC6H4R8;

R39 is H; alkyl; alkenyl; or aryl-lower alkyl;

R40 is H; alkyl; alkenyl; or aryl-lower alkyl;

R41 is H; F; Br; Cl; NO2; CF3; alkyl; alkenyl; —(CH2)p(CHR61)sOR55; —(CH2)p(CHR61)sNR33R34; —(CH2)p(CHR61)sOCONR33R75; —(CH2)p(CHR61)sNR20CONR33R82; —(CH2)o(CHR61)sCOOR57; —(CH2)o(CHR61)sCONR58R59; —(CH2)o(CHR61)sPO(OR60)2; —(CH2)o(CHR61)sSO2R62; or —(CH2)o(CHR61)s C6H4R8;

R42 is H; F; Br; Cl; NO2; CF3; alkyl; alkenyl; —(CH2)p(CHR61)sOR55; —(CH2)p(CHR61)sNR33R34; —(CH2)p(CHR61)sOCONR33R75; —(CH2)p(CHR61)sNR20CONR33R82; —(CH2)o(CHR61)sCOOR57; —(CH2)o(CHR61)sCONR58R59; —(CH2)o(CHR61)sPO(OR60)2; —(CH2)o(CHR61)sSO2R62; or —(CH2)o(CHR61)s C6H4R8;

R43 is H; alkyl; alkenyl; —(CH2)m(CHR61)sOR55; —(CH2)m(CHR61)sNR33R34; —(CH2)m(CHR61)sOCONR33R75; —(CH2)m(CHR61)sNR20CONR33R82; —(CH2)o(CHR61)sCOOR57; —(CH2)o(CHR61)sCONR58R59; —(CH2)o(CHR61)sPO(OR60)2; —(CH2)o(CHR61)sSO2R62; or —(CH2)o(CHR61)s C6H4R8;

R44 is alkyl; alkenyl; —(CH2)r(CHR61)sOR55; —(CH2)r(CHR61)sSR56; —(CH2)r(CHR61)sNR33R34; —(CH2)r(CHR61)sOCONR33R75; —(CH2)r(CHR61)sNR20CONR33R82; —(CH2)r(CHR61)sCOOR57; —(CH2)r(CHR61)sCONR58R59; —(CH2)r(CHR61)sPO(OR60)2; —(CH2)r(CHR61)s SO2R62; or —(CH2)r(CHR61)sC6H4R8;

R45 is H; alkyl; alkenyl; —(CH2)o(CHR61)sOR55; —(CH2)o(CHR61)sSR56; —(CH2)o(CHR61)sNR33R34; —(CH2)o(CHR61)sOCONR33R75; —(CH2)o(CHR61)sNR20CONR33R82; —(CH2)o(CHR61)sCOOR57; —(CH2)s(CHR61)sCONR58R59; —(CH2)s(CHR61)sPO(OR60)2; —(CH2)s(CHR61)s SO2R62; or —(CH2)s(CHR61)sC6H4R8;

R46 is H; alkyl; alkenyl; or —(CH2)o(CHR61)pC6H4R8;

R47 is H; alkyl; alkenyl; or —(CH2)o(CHR61)sOR55;

R48 is H; lower alkyl; lower alkenyl; or aryl-lower alkyl;

R49 is H; alkyl; alkenyl; —(CHR61)sCOOR57; (CHR61)sCONR58R59; —(CHR61)sPO(OR60)2; —(CHR61)sSOR62; or —(CHR61)sC6H4R8;

R50 is H; lower alkyl; or aryl-lower alkyl;

R51 is H; alkyl; alkenyl; —(CH2)m(CHR61)sOR55; —(CH2)m(CHR61)sSR56; —(CH2)m(CHR61)sNR33R34; —(CH2)m(CHR61)sOCONR33R75; —(CH2)m(CHR61)sNR20CONR33R82; —(CH2)o(CHR61)sCOOR57; —(CH2)o(CHR61)sCONR58R59; —(CH2)o(CHR61)pPO(OR60)2; —(CH2)p(CHR61)s SO2R62; or —(CH2)p(CHR61)sC6H4R8;

R52 is H; alkyl; alkenyl; —(CH2)m(CHR61)sOR55; —(CH2)m(CHR61)sSR56; —(CH2)m(CHR61)sNR33R34; —(CH2)m(CHR61)sOCONR33R75; —(CH2)m(CHR61)sNR20CONR33R82; —(CH2)o(CHR61)sCOOR57; —(CH2)o(CHR61)sCONR58R59; —(CH2)o(CHR61)pPO(OR60)2; —(CH2)p(CHR61)s SO2R62; or —(CH2)p(CHR61)sC6H4R8;

R53 is H; alkyl; alkenyl; —(CH2)m(CHR61)sOR55; —(CH2)m(CHR61)sSR56; —(CH2)m(CHR61)sNR33R34; —(CH2)m(CHR61)sOCONR33R75;

—(CH2)m(CHR61)sNR20CONR33R82; —(CH2)o(CHR61)sCOOR57; —(CH2)o(CHR61)sCONR58R59; —(CH2)o(CHR61)pPO(OR60)2; —(CH2)p(CHR61)s SO2R62; or —(CH2)p(CHR61)sC6H4R8;

R54 is H; alkyl; alkenyl; —(CH2)m(CHR61)sOR55; —(CH2)m(CHR61)sNR33R34; —(CH2)m(CHR61)sOCONR33R75; —(CH2)m(CHR61)sNR20CONR33R82; —(CH2)o(CHR61)COOR57; —(CH2)o(CHR61)sCONR58R59; or —(CH2)o(CHR61)s C6H4R8;

R55 is H; lower alkyl; lower alkenyl; aryl-lower alkyl; —(CH2)m(CHR61)sOR57; —(CH2)m(CHR61)sNR34R63; —(CH2)m(CHR61)sOCONR75R82; —(CH2)m(CHR61)sNR20CONR78R82; —(CH2)o(CHR61)s—COR64; —(CH2)o(CHR61)COOR57; or —(CH2)o(CHR61)sCONR58R59;

R56 is H; lower alkyl; lower alkenyl; aryl-lower alkyl; —(CH2)m(CHR61)sOR57; —(CH2)m(CHR61)sNR34R63; —(CH2)m(CHR61)sOCONR75R82; —(CH2)m(CHR61)sNR20CONR78R82; —(CH2)o(CHR61)s—COR64; or —(CH2)o(CHR61)sCONR58R59;

R57 is H; lower alkyl; lower alkenyl; aryl lower alkyl; or heteroaryl lower alkyl;

R58 is H; lower alkyl; lower alkenyl; aryl; heteroaryl; aryl-lower alkyl; or heteroaryl-lower alkyl;

R59 is H; lower alkyl; lower alkenyl; aryl; heteroaryl; aryl-lower alkyl; or heteroaryl-lower alkyl; or R58 and R59 taken together can form: —(CH2)2-6-; —(CH2)2O(CH2)2-; —(CH2)2S(CH2)2-; or —(CH2)2NR57(CH2)2-;

R60 is H; lower alkyl; lower alkenyl; aryl; or aryl-lower alkyl;

R61 is alkyl; alkenyl; aryl; heteroaryl; aryl-lower alkyl; heteroaryl-lower alkyl; —(CH2)pOR55; —(CH2)pNR33R34; —(CH2)pOCONR75R82; —(CH2)pNR20CONR78R82; —(CH2)oCOOR37; —(CH2)oPO(OR60)2;

R62 is lower alkyl; lower alkenyl; aryl, heteroaryl; or aryl-lower alkyl;

R63 is H; lower alkyl; lower alkenyl; aryl, heteroaryl; aryl-lower alkyl; heteroaryl-lower alkyl; —COR64; —COOR57; —CONR58R59; —SO2R62; or —PO(OR60)2; or R34 and R63 taken together can form: —(CH2)2-6-; —(CH2)2-0(CH2)2-; —(CH2)2S(CH2)2-; or —(CH2)2NR57(CH2)2-;

R64 is H; lower alkyl; lower alkenyl; aryl; heteroaryl; aryl-lower alkyl; heteroaryl-lower alkyl; —(CH2)p(CHR61)sOR65; —(CH2)p(CHR61)sSR66; —(CH2)p(CHR61)sNR34R63; —(CH2)P(CHR61)sOCONR75R82; or —(CH2)P(CHR61)sNR20CONR78R82;

R65 is H; lower alkyl; lower alkenyl; aryl, aryl-lower alkyl; heteroaryl-lower alkyl; —COR57; —COOR57; or —CONR58R59;

R66 is H; lower alkyl; lower alkenyl; aryl; aryl-lower alkyl; heteroaryl-lower alkyl; or —CONR58R59;

R67 is H; Cl; Br; F; NO2; —NR34COR57; —CF3; CN; —OCF3; —OCHF2; —OR57; —SR62; lower alkyl; or lower alkenyl;

R68 is H; Cl; Br; F; NO2; —NR34COR57; —CF3; CN; —OCF3; —OCHF2; —OR57; —SR62; lower alkyl; or lower alkenyl;

R69 is H; Cl; Br; F; NO2; —NR34COR57; —CF3; CN; —OCF3; —OCHF2; —OR57; —SR62; lower alkyl; or lower alkenyl;

R70 is H; Cl; Br; F; NO2; —NR34COR57; —CF3; CN; —OCF3; —OCHF2; —OR57; —SR62; lower alkyl; or lower alkenyl;

R71 is lower alkyl; lower alkenyl; —(CH2)p(CHR61)sOR75; —(CH2)p(CHR61)sSR75; —(CH2)p(CHR61)sNR33R34; —(CH2)p(CHR61)sOCONR33R75; —(CH2)p(CHR61)sNR20CONR33R82; —(CH2)o(CHR61)sCOOR75; —(CH2)pCONR58R59; —(CH2)pPO(OR62)2; —(CH2)pSO2R62; or —(CH2)o-C6R67R68R69R7OR76;

R72 is alkyl; alkenyl; —(CH2)p(CHR61)sOR85; or —(CH2)p(CHR61)sSR85;

R73 is —(CH2)OR77; —(CH2)r-O—(CH2)OR77; —(CH2)rS(CH2)OR77; or —(CH2)rNR20(CH2)OR77;

R74 is —(CH2)pNR78R79; —(CH2)pNR77R80; —(CH2)pC(=NR80)NR78R79; —(CH2)pC(=NOR50)NR78R79; —(CH2)pC(=NNR78R79)NR78R79; —(CH2)pNR80C(=NR80)NR78R79; —(CH2)pN=C(NR78R80)NR79R80; —(CH2)pC6H4NR77R80; —(CH2)pC6H4C(=NR80)NR78R79; —(CH2)pC6H4C(=NOR50)NR78R79; —(CH2)pC6H4C(=NNR78R79)NR78R79; —(CH2)pC6H4NR80C(=NR80)NR78R79; —(CH2)pC6H4N=C(NR78R80)NR79R80; —(CH2)r-O—(CH2)mNR78R79; —(CH2)r-O—(CH2)mNR77R80; —(CH2)r-O—(CH2)pC(=NR80)NR78R79; —(CH2)r-O—(CH2)pC(=NOR50)NR78R79; —(CH2)r-O—(CH2)pC(=NNR78R79)NR78R79; —(CH2)r-O—(CH2)mNR80C(=NR80)NR78R79; —(CH2)r-O—(CH2)mN=C(NR78R80)NR79R80; —(CH2)r-O—(CH2)pC6H4CNR78R79; —(CH2)r-O—(CH2)pC6H4C(=NR80)NR78R79; —(CH2)r-O—(CH2)pC6H4C(=NOR50)NR78R79; —(CH2)r-O—(CH2)pC6H4C(=NNR78R79)NR78R79; —(CH2)r-O—(CH2)pC6H4NR80C(=NR80)NR78R79; —(CH2)rS(CH2)mNR78R79; —(CH2)rS(C112)mNR77R80; —(CH2)rS(CH2)pC(=NR80)NR78R79; —(CH2)rS(CH2)pC(=NOR50)NR78R79; —(CH2)rS(CH2)pC(=NNR78R79)NR78R79; —(CH2)rS(CH2)mNR80C(=NR80)NR78R79; —(CH2)rS(CH2)mN=C(NR78R80)NR79R80; —(CH2)rS(CH2)pC6H4CNR78R79; —(CH2)rS(CH2)pC6H4C(=NR80)NR78R79; —(CH2)rS(CH2)pC6H4C(=NOR50)NR78R79; —(CH2)rS(CH2)pC6H4C(=NNR78R79)NR78R79; —(CH2)rS(CH2)pC6H4NR80C(=NR80)NR78R79; —(CH2)pNR80COR64; —(CH2)pNR80COR77; —(CH2)pNR80CONR78R79; or —(CH2)pC6H4NR80CONR78R79;

R75 is lower alkyl; lower alkenyl; or aryl-lower alkyl; or

R33 and R75 taken together can form: —(CH2)2-6-; —(CH2)2O(CH2)2-; —(CH2)2S(CH2)2-; or —(CH2)2NR57(CH2)2-; or R75 and R82 taken together can form: —(CH2)2-6-; —(CH2)2O(CH2)2-; —(CH2)2S(CH2)2-; or —(CH2)2NR57(CH2)2-;

R76 is H; lower alkyl; lower alkenyl; aryl-lower alkyl; —(CH2)oOR72; —(CH2)oSR72; —(CH2)oNR33R34; —(CH2)oOCONR33R75; —(CH2)oNR20CONR33R81; —(CH2)oCOOR75; —(CH2)oCONR58R59; —(CH2)oPO(OR60)2; —(CH2)pSO2R62; or —(CH2)oCOR64;

R77 is —C6R67R68R69R7OR76 with the proviso that at least two of R67, R68, R69 and R70 are H; or a heteroaryl group of one of the formulae
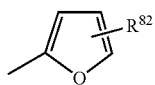
H1
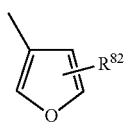
H2
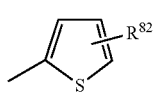
H3
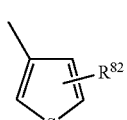
H4
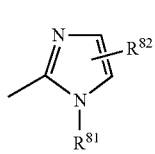
H5
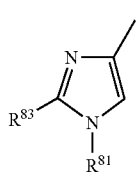
H6
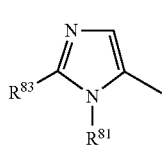
H7
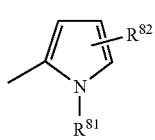
H8
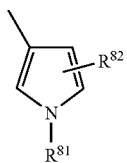
H9
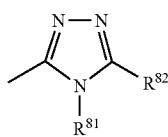
H10
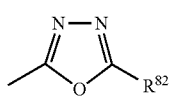
H11
-continued
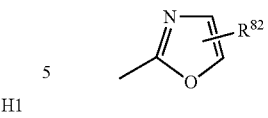
H12
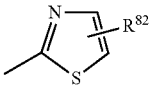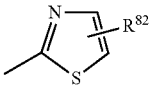
H13
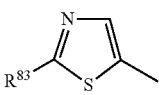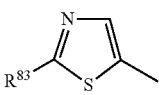
H14
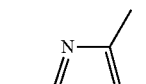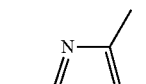
H15
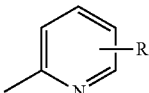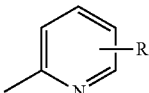
H16
H17
H18
H19
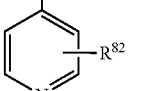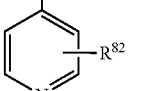
H20
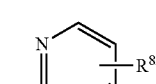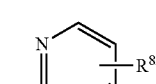
H21
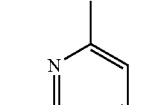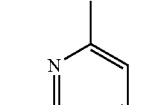
H22
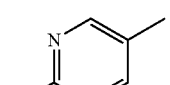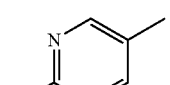
H23
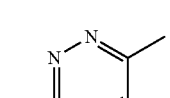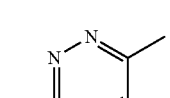
H24
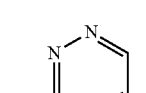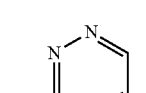

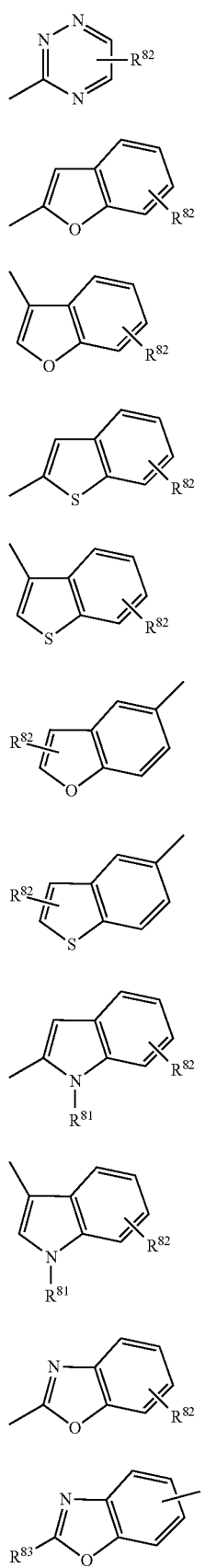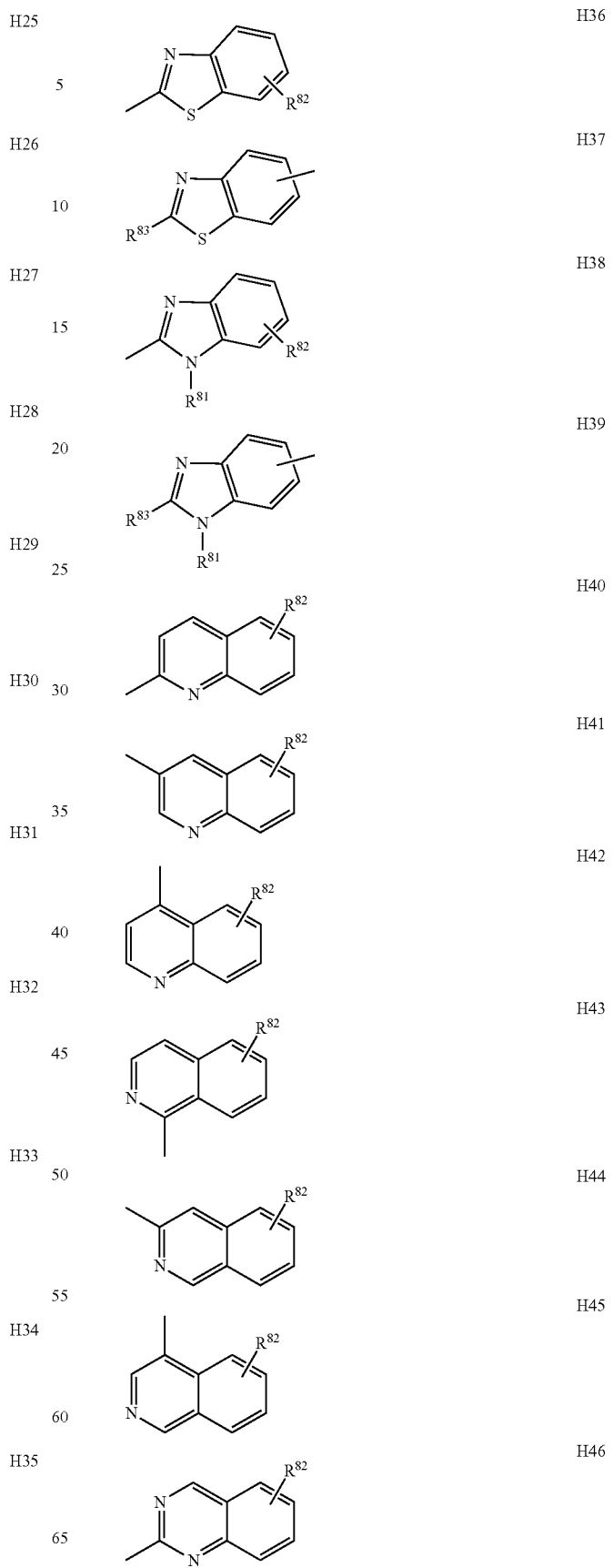

-continued

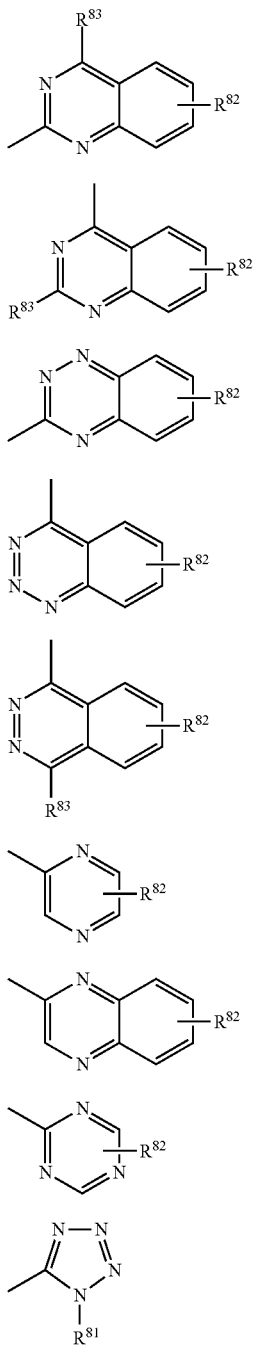

R78 is H; lower alkyl; aryl; or aryl-lower alkyl; or
R78 and R82 taken together can form: —(CH2)2-6-;
  —(CH2)2O(CH2)2-; —(CH2)2S(CH2)2-; or —(CH2)
  2NR57(CH2)2-;
R79 is H; lower alkyl; aryl; or aryl-lower alkyl; or
R78 and R79, taken together, can be —(CH2)2-7-;
  —(CH2)2O(CH2)2-; or —(CH2)2NR57(CH2)2-;
R80 is H; or lower alkyl;
R81 is H; lower alkyl; or aryl-lower alkyl;
R33 and R81 taken together can form: —(CH2)2-6-;
  —(CH2)2O(CH2)2-; —(CH2)2S(CH2)2-; or —(CH2)
  2NR57(CH2)2-;

R82 is H; —CF3; —OCF3; —OCHF2; lower alkyl; aryl;
  heteroaryl; or aryl-lower alkyl;
R83 is H; lower alkyl; aryl; or —NR78R79;
R84 is —(CH2)p(CHR61)sOH; —(CH2)pCOOR80;
  —(CH2)p(CHR61)sSH; —(CH2)pCONR78R79;
  —(CH2)pNR80CONR78R79; —(CH2)p
  C6H4CONR78R79; or —(CH2)p
  C6H4NR80CONR78R79;
R85 is lower alkyl; or lower alkenyl;
m is 2-4; o is 0-4; p is 1-4; q is 0-2; r is 1 or 2; s is 0 or 1;
Z is a chain of 14 α-amino and/or α-hydroxy acid residues,
  the positions of said amino and/or hydroxy acid residues
  in said chain being counted starting from the N-terminal
  amino acid or O-terminal hydroxy acid, whereby these
  amino or hydroxy acid residues are, depending on their
  position in the chains, Gly, a Glycolic acid residue, Pro,
  -A-CO—, or of one of the types
C: —NR20CH(R72)CO—;
D: —NR20CH(R73)CO—;
E: —NR20CH(R74)CO—;
F: —NR20CH(R84)CO—;
H: —NR20-CH(CO—)—(CH2)4-7-CH(CO—)—NR20-;
  —NR20-CH(CO—)—(CH2)pSS(CH2)p—CH(CO—)—
  NR20-;
  —NR20-CH(CO—)-(—(CH2)pNR20CO(CH2)p—CH
  (CO—)—NR20-; or
  —NR20-CH(CO—)-(—(CH2)pNR20CONR20(CH2)
  p—CH(CO—)—NR20-; and
L: —O—CH(R71)CO—; —O—CH(R72)CO—;
  —O—CH(R73)CO—; —OCH(R74)CO—; or —OCH
  (R84)CO—;
with the proviso that in said chain Z of 14 α-amino and/or
  α-hydroxy acid residues the amino or hydroxy acid resi-
  dues in positions 1 to 14 are:
  P1: of type C, type D, type F or of type L;
  P2: of type D, type E, type F, or of type L;
  P3: of type C, type D, type E, type F, type L, or Gly, or a
    Glycolic acid residue;
  P4: of type C, type D, type E or of type F;
  P5: of type E, type F or of type L;
  P6: of type C, type L, Gly or a Glycolic acid residue;
  P7: of formula -A-CO—, Pro, Gly or a Glycolic acid
    residue;
  P8: of formula A-CO—, type C, type D, type E, type F or
    of type L;
  P9: of type D or type E;
  P10: of type C or type D;
  P11: of type C, type D or type F;
  P12: of type D, type F or of type L;
  P13: of type C, type D, type E, type F or of type L; and
  P14: of type C, type E, type F or of type L; or
  P4 and P11, taken together, can form a group of type H;
at P5, P7 and P13 also D-isomers being possible;
and with the further proviso that the molecule contains at
  least one but not more than 3 α-hydroxy acid residues;
enantiomers thereof; and pharmaceutically acceptable
  salts thereof.
2. The compound according to claim 1 wherein

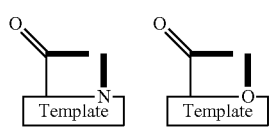

is a group of formula (a1) or (a2).

3. The compound according to claim 2 wherein A is a group of one of the formulae A1 to A69 and A105;

R1 is hydrogen or lower alkyl;

R2 is H; lower alkyl; lower alkenyl; —(CH2)mOR55 (where R55 is lower alkyl; or lower alkenyl); —(CH2)mSR56 (where R56 is lower alkyl; or lower alkenyl); —(CH2)mNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)mOCONR33R75 (where R33 is H; lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)mNR20CONR33R81 (where R20 is H; or lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)oN(R20)COR64(where: R20 is H; or lower alkyl; R64 is lower alkyl; or lower alkenyl); (CH2)oCOOR57 (where R57 is lower alkyl; or lower alkenyl); —(CH2)oCONR58R59 (where R58 is lower alkyl; or lower alkenyl; and R59 is H; or lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is H; lower alkyl; or lower alkenyl); —(CH2)oSO2R62 (where R62 is lower alkyl; or lower alkenyl); —(CH2)qC6H4R8 (where R8 is H; F; Cl; CF3; lower alkyl; lower alkenyl; or lower alkoxy) or —(CH2)qCHN4R8;

R3 is H; lower alkyl; lower alkenyl; —(CH2)mOR55 (where R55 is lower alkyl; or lower alkenyl); —(CH2)mSR56 (where R56 is lower alkyl; or lower alkenyl); —(CH2)mNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)mOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)mNR20CONR33R81 (where R20 is H; or lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)oN(R20)COR64 (where: R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl; or lower alkenyl; and R59 is H; lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF$_3$; lower alkyl; lower alkenyl; or lower alkoxy);

R4 is H; lower alkyl; lower alkenyl; —(CH2)mOR55 (where R55 is lower alkyl; or lower alkenyl); —(CH2)mSR56 (where R56 is lower alkyl; or lower alkenyl); —(CH2)mNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)mOCONR33R75 (where R33 is H; or lower alkyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)mNR20CONR33R81 (where R20 is H; or lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)mN(R20)COR64(where: R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl; or lower alkenyl; and R59 is H; or lower alkyl; or R58 and R59 taken together are —(CH2)2-6-; —(CH2)2O(CH2)2-; —(CH2)2S(CH2)2-; or —(CH2)2NR57(CH2)2-; where R57: is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy);

R5 is lower alkyl; lower alkenyl; —(CH2)oOR55 (where R55 is lower alkyl; or lower alkenyl); —(CH2)oSR56 (where R56 is lower alkyl; or lower alkenyl); (CH2)oNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)oOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)oNR20CONR33R81 (where R20 is H; or lower lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)oN(R20)COR64 (where: R20 is H; or lower alkyl; R64 is alkyl; alkenyl; aryl; aryl-lower alkyl; or heteroaryl-lower alkyl); —(CH2)oCOOR57 (where R57 is lower alkyl; or lower alkenyl); —(CH2)oCONR58R59 (where R58 is lower alkyl; or lower alkenyl; and R59 is H; or lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy);

R6 is H; lower alkyl; lower alkenyl; —(CH2)oOR55 (where R55 is lower alkyl; or lower alkenyl); —(CH2)oSR56 (where R56 is lower alkyl; or lower alkenyl); —(CH2)oNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)oOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)oNR20CONR33R81 (where R20 is H; or lower lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)oN(R20)COR64 (where R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl; or lower alkenyl; and R59 is H; or lower alkyl; or R58 and R59 taken together are —(CH2)2-6-; —(CH2)2O(CH2)2-; —(CH2)2S(CH2)2-; or —(CH2)2NR57 (CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy);

R7 is lower alkyl; lower alkenyl; —(CH2)qOR55 (where R55 is lower alkyl; or lower alkenyl); —(CH2)qSR56 (where R56 is lower alkyl; or lower alkenyl); —(CH2)qNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)qOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57 (CH2)2-; where R57 is H; or lower alkyl); —(CH2)qNR20CONR33R81 (where R20 is H; or lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)qN(R20)COR64(where: R20 is H; or lower alkyl; R64 is lower alkyl; or lower alkenyl); —(CH2)rCOOR57 (where R57 is lower alkyl; or lower alkenyl); —(CH2)qCONR58R59 (where R58 is lower alkyl; or lower alkenyl; and R59 is H; or lower alkyl; or R58 and R59 taken together are —(CH2)2-6-; —(CH2)2O(CH2)2-; —(CH2)2S(CH2)2-; or —(CH2)2NR57 (CH2)2-; where R57 is H; or lower alkyl); —(CH2)rPO(OR60)2 (where R60 is lower alkyl; or lower alkenyl); —(CH2)rSO2R62 (where R62 is lower alkyl; or lower alkenyl); or —(CH2)qC6H4R8 (where R8 is H; F; Cl; CF3; lower alkyl; lower alkenyl; or lower alkoxy);

R8 is H; F; Cl; CF3; lower alkyl; lower alkenyl; —(CH2)oOR55 (where R55 is lower alkyl; or lower alkenyl); —(CH2)oSR56 (where R56 is lower alkyl; or lower alkenyl); —(CH2)oNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57 (CH2)2-; where R57 is H; or lower alkyl); —(CH2)oOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)oNR20CONR33R81 (where R20 is H; or lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)oN(R20)COR64 (where R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl; or lower alkenyl; and R59 is H; or lower alkyl; or R58 and R59 taken together are —(CH2)2-6-; —(CH2)2O(CH2)2-; —(CH2)2S(CH2)2-; or —(CH2)2NR57 (CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy);

R9 is lower alkyl; lower alkenyl; —(CH2)oOR55 (where R55 is lower alkyl; or lower alkenyl); —(CH2)oSR56 (where R56 is lower alkyl; or lower alkenyl); —(CH2)oNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)oOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)mNR20CONR33R81 (where R20 is H; or lower lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)oN(R20)COR64(where R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl; or lower alkenyl; and R59 is H; or lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy);

R10 is lower alkyl; lower alkenyl; —(CH2)oOR55 (where R55 is lower alkyl; or lower alkenyl); —(CH2)oSR56 (where R56 is lower alkyl; or lower alkenyl); —(CH2)oNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)oOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57: H is or lower alkyl); —(CH2)oNR20CONR33R81 (where R20 is H; or lower lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)oN(R20)COR64(where R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl; or lower alkenyl; and R59 is H; lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl);

—(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy);

R11 is H; lower alkyl; lower alkenyl; —(CH2)mOR55 (where R55 is lower alkyl; or lower alkenyl); —(CH2)mSR56 (where R56 is lower alkyl; or lower alkenyl); —(CH2)mNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)mOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)mNR20CONR33R81 (where R20 is H; or lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)mN(R20)COR64 (where R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl; or lower alkenyl; and R59 is H; lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy);

R12 is H; lower alkyl; lower alkenyl; —(CH2)mOR55 (where R55 is lower alkyl; or lower alkenyl); —(CH2)mSR56 (where R56 is lower alkyl; or lower alkenyl); —(CH2)mNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)mOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)mNR20CONR33R81 (where R20 is H; or lower lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)mN(R20)COR64 (where: R20 is H; or lower alkyl; R64 is lower alkyl; or lower alkenyl); —(CH2)rCOOR57 (where R57 is lower alkyl; or lower alkenyl); —(CH2)rCONR58R59 (where R58 is lower alkyl; or lower alkenyl; and R59 is H; or lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)rPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy);

R13 is lower alkyl; lower alkenyl; —(CH2)qOR55 (where R55 is lower alkyl; or lower alkenyl); —(CH2)qSR56 (where R56 is lower alkyl; or lower alkenyl); —(CH2)qNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)qOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)qNR20CONR33R81 (where R20 is H; or lower lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)qN(R20)COR64 (where: R20 is H; or lower alkyl; R64 is lower alkyl; or lower alkenyl); —(CH2)rCOOR57 (where R57 is lower alkyl; or lower alkenyl); —(CH2)qCONR58R59 (where R58 is lower alkyl; or lower alkenyl; and R59 is H; or lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)rPO(OR60)2 (where R60 is lower alkyl; or lower alkenyl); —(CH2)rSO2R62 (where R62 is lower alkyl; or lower alkenyl); or —(CH2)qC6H4R8 (where R8 is H; F; Cl; CF3; lower alkyl; lower alkenyl; or lower alkoxy);

R14 is H; lower alkyl; lower alkenyl; —(CH2)mOR55 (where R55 is lower alkyl; or lower alkenyl); —(CH2)mSR56 (where R56 is lower alkyl; or lower alkenyl); —(CH2)mNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)mOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)mNR20CONR33R81 (where R20 is H; or lower lower alkyl; R33 is H; or lower alkyl; or lower alkenyl is R81: H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)mN(R20)COR64 (where: R20 is H; lower alkyl; R64 is lower alkyl; or lower alkenyl); —(CH2)oCOOR57 (where R57 is lower alkyl; or lower alkenyl); —(CH2)oCONR58R59 (where R58 is lower alkyl; or lower alkenyl; and R59 is H; or lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy);

R15 is lower alkyl; lower alkenyl; —(CH2)oOR55 (where R55 is lower alkyl; or lower alkenyl); —(CH2)oSR56 (where R56 is lower alkyl; or lower alkenyl); —(CH2)oNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)oOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl);

—(CH2)oNR20CONR33R81 (where R20 is H; or lower lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)ₒN(R20)COR64 (where R20 is H; or lower alkyl; R64 is lower alkyl; or lower alkenyl); —NR20CO lower alkyl (R20=H; or lower alkyl); being particularly favoured; —(CH2)oCOOR57 (where R57 is lower alkyl; or lower alkenyl); —(CH2)oCONR58R59 (where R58 is lower alkyl, or lower alkenyl; and R59 is H; lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or (CH2)qC6H4R8 (where R8 is H; F; Cl; CF3; lower alkyl; lower alkenyl; or lower alkoxy);

R16 is lower alkyl; lower alkenyl; —(CH2)oOR55 (where R55 is lower alkyl; or lower alkenyl); —(CH2)oSR56 (where R56 is lower alkyl; or lower alkenyl); —(CH2)oNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)oOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)oNR20CONR33R81 (where R20 is H; or lower lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)oN(R20)COR64 (where R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl; or lower alkenyl; and R59 is H; or lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy); and R17 is lower alkyl; lower alkenyl; —(CH2)qOR55 (where R55 is lower alkyl; or lower alkenyl); —(CH2)qSR56 (where R56 is lower alkyl; or lower alkenyl); —(CH2)qNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)qOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)qNR20CONR33R81 (where R20 is H; or lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)qN(R20)COR64(where: R20 is H; or lower alkyl; R64 is lower alkyl; or lower alkenyl); —(CH2)rCOOR57 (where R57 is lower alkyl; or lower alkenyl); —(CH2)qCONR58R59 (where R58 is lower alkyl; or lower alkenyl; and R59 is H; lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)rPO(OR60)2 (where R60 is lower alkyl; or lower alkenyl); —(CH2)rSO2R62 (where R62 is lower alkyl; or lower alkenyl); or —(CH2)qC6H4R8 (where R8 is H; F; Cl; CF3; lower alkyl; lower alkenyl; or lower alkoxy).

4. The compound according to claim 2 or 3 wherein A is a group of one of the formulae A5 (with R2 being H); A8; A22; A25; A38 (with R2 being H); A42; and A50.

5. The compound according to claim 4 wherein A is a group of formula

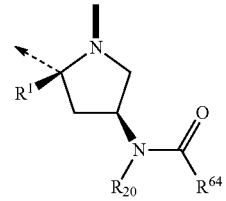

A8' wherein R20 is H or lower alkyl; and R64 is alkyl; alkenyl; —[(CH2)u-X]t-CH3, wherein X is —O—; —NR20-, —S—; u=1-3, t=1-6; aryl; aryl-lower alkyl; or heteroaryl-lower alkyl.

6. The compound according to claim 5 wherein R64 is n-hexyl; n-heptyl; 4-(phenyl)benzyl; diphenylmethyl, 3-amino-propyl; 5-amino-pentyl; methyl; ethyl; isopropyl; isobutyl; n-propyl; cyclohexyl; cyclohexylmethyl; n-butyl; phenyl; benzyl; (3-indolyl)methyl; 2-(3-indolyl)ethyl; (4-phenyl)phenyl; n-nonyl; CH3-OCH2CH2-OCH2- or CH3-(OCH2CH2)2-OCH2-.

7. The compound according to claim 2 wherein A is a group of one of the formulae A70 to A104 or A106 to A110;

R20 is H; or lower alkyl;

R18 is lower alkyl;

R19 is lower alkyl; lower alkenyl; —(CH2)pOR55 (where R55 is lower alkyl; or lower alkenyl); —(CH2)pSR56 (where R56 is lower alkyl; or lower alkenyl); —(CH2)pNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)pOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)pNR20CONR33R81 (where R20 is H; or lower lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)pN(R20)COR64 (where: R20 is H; or lower alkyl; R64 is lower alkyl; or lower alkenyl); (CH2)pCOOR57 (where R57: lower alkyl; or lower alkenyl); (CH2)pCONR58R59 (where R58 is lower alkyl; or lower alkenyl; and R59 is H; or lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO (OR60)2 (where R60 is lower alkyl; or lower alkenyl); —(CH2)pSO2R62 (where R62 is lower alkyl; or lower alkenyl); or —(CH2)oC6H4R8 (where R8 is H; F; Cl; CF3; lower alkyl; lower alkenyl; or lower alkoxy);

R21 is H; lower alkyl; lower alkenyl; —(CH2)oOR55 (where R55 is lower alkyl; or lower alkenyl); —(CH2)oSR56 (where R56 is lower alkyl; or lower alkenyl); —(CH2)oNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)oOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)oNR20CONR33R81 (where R20 is H; or lower lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)oN(R20)COR64 (where: R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl, or lower alkenyl; and R59 is H; lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy);

R22 is lower alkyl; lower alkenyl; —(CH2)oOR55 (where R55 is lower alkyl; or lower alkenyl); —(CH2)oSR56 (where R56 is lower alkyl; or lower alkenyl); —(CH2)oNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)oOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)oNR20CONR33R81 (where R20 is H; or lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)oN(R20)COR64(where R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl, or lower alkenyl; and R59 is H; lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF; lower alkyl; lower alkenyl; or lower alkoxy);

R23 is H; lower alkyl; lower alkenyl; —(CH2)oOR55 (where R55 is lower alkyl; or lower alkenyl); —(CH2)oSR56 (where R56 is lower alkyl; or lower alkenyl); —(CH2)oNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)oOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)oNR20CONR33R81 (where R20 is H; or lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)oN(R20)COR64 (where: R20 is H; or lower alkyl; R64 is lower alkyl; or lower alkenyl); —NR20CO-lower alkyl (R20=H; or lower alkyl) being particularly favoured; —(CH2)oCOOR57 (where R57 is lower alkyl; or lower alkenyl); —(CH2)oCONR58R59 (where R58 is lower alkyl, or lower alkenyl; and R59 is H; lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy);

R24 is lower alkyl; lower alkenyl; —(CH2)oOR55 (where R55 is lower alkyl; or lower alkenyl); —(CH2)oSR56 (where R56 is lower alkyl; or lower alkenyl); —(CH2)oNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)oOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)oNR20CONR33R81 (where R20 is H; or lower lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)oN(R20)COR64 (where: R20 is H; or lower alkyl; R64 is lower alkyl; or lower alkenyl); —NR20CO-lower alkyl (R20=H; or lower alkyl) being particularly favoured; —(CH2)oCOOR57 (where R57 is lower alkyl; or lower alkenyl); —(CH2)oCONR58R59 (where R58 is lower alkyl, or lower alkenyl; and R59 is H; lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy);

R25 is H; lower alkyl; lower alkenyl; —(CH2)mOR55 (where R55 is lower alkyl; or lower alkenyl); —(CH2)mNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)mOCONR33R75 (where R33 is H; or lower alkyl; or lower alkenyl; R75 is lower alkyl;

or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)mNR20CONR33R81 (where R20 is H; or lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)mN(R20)COR64 (where: R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl; or lower alkenyl; and R59 is H; lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy);

R26 is H; lower alkyl; lower alkenyl; —(CH2)mOR55 (where R55 is lower alkyl; or lower alkenyl); —(CH2)mNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)mOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)mNR20CONR33R81 (where R20 is H; or lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)mN(R20)COR64 (where: R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl; or lower alkenyl; and R59 is H; lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy); or, alternatively, R25 and R26 taken together are —(CH2)2-6-; —(CH2)2O(CH2)2-; —(CH2)2S(CH2)2-; or —(CH2)2NR34(CH2)2-;

R27 is H; lower alkyl; lower alkenyl; —(CH2)oOR55 (where R55 is lower alkyl; or lower alkenyl); —(CH2)oSR56 (where R56 is lower alkyl; or lower alkenyl); —(CH2)oNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)oOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)oNR20CONR33R81 (where R20 is H; or lower lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)oN(R20)COR64 (where R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl, or lower alkenyl; and R59 is H; lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy);

R28 is lower alkyl; lower alkenyl; —(CH2)oOR55 (where R55 is lower alkyl; or lower alkenyl); —(CH2)oSR56 (where R56 is lower alkyl; or lower alkenyl); —(CH2)oNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)oOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)oNR20CONR33R81 (where R20 is H; or lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)oN(R20)COR64(where: R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl, or lower alkenyl; and R59 is H; lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy); and R29 is lower alkyl; lower alkenyl; —(CH2)oOR55 (where R55 is lower alkyl; or lower alkenyl); —(CH2)oSR56 (where R56 is lower alkyl; or lower alkenyl); —(CH2)oNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)oOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)oNR20CONR33R81 (where R20 is H; or lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)oN(R20)COR64(where: R20 is H; or lower alkyl; R64 is lower alkyl; or lower alkenyl); —NR20CO-lower-alkyl (R20=H; or lower alkyl) being particularly favoured; —(CH2)oCOOR57 (where R57 is lower alkyl; or lower alkenyl); —(CH2)oCONR58R59 (where R58 is lower alkyl, or lower alkenyl; and R59 is H; lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy).

8. The compound according to claim 7 wherein R23, R24 and R29 are —NR20-CO-lower alkyl where R20 is H; or lower alkyl.

9. The compound according to claim 7 or 8 wherein A is a group of one of the formulae A74 (with R22 being H); A75; A76; A77 (with R22 being H); A78; and A79.

10. The compound according to claim 2 wherein B is a group of formula —NR20CH(R71)-, or —OCH(R71)- or —OCH(R72)- or —OCH(R73)- or —OCH(R74)- or —OCH(R84)-, or an enantiomer of one of the groups A5 (with R2 being H); A8; A22; A25; A38 (with R2 being H); A42; A47; and A50.

11. The compound according to claim 10 wherein B—CO is Ala; Arg; Asn; Asp; Cys; Gln; Glu; Gly; His; Ile; Leu; Lys; Met; Phe; Pro; Ser; Thr; Trp; Tyr; Val; Cit; Orn; tBuA; Sar; t-BuG; 4AmPhe; 3AmPhe; 2AmPhe; Phe(mC(NH2)=NH); Phe(pC(NH2)=NH); Phe(mNHC(NH2)=NH); Phe(pNHC(NH2)=NH); Phg; Cha; C4al; C5al; Nle; 2-Nal; 1-Nal; 4Cl-Phe; 3Cl1-Phe; 2Cl-Phe; 3,4Cl2Phe; 4F-Phe; 3F-Phe; 2F-Phe; Tic; Thi; Tza; Mso; AcLys; Dpr; A2Bu; Dab; Abu; Aha; Aib; Y(Bzl); Bip; S(Bzl); T(Bzl); hCha; hCys; hSer; hArg; hPhe; Bpa; Pip; OctG; MePhe; MeNle; MeAla; MeIle; MeVal; MeLeu; 4Hyp1; 4Hyp2; 4 Mp1; 4 Mp2; Oic; Glycolic acid; Lac; Hmb; H3mp; H4mp; Hmtb; Hhpp; Himp; Hpp; Hinp; Dhp; Hbd; Hpd; Ahh; Hgp; Hmcp; Haa; Hcp; Hcb; 3Dhb; Hpa; Ahp; Ahb; 3Ahb; 4Dhb; Hmcb; Hpb; Hcb; Hgh; Hcap; Ahp; Hdmp; Hdmb; Hchp; Hcbp; Hcpp; Hca; Hda; H2np; H1np; Hbp; 4Clphp; 3Clphp; 2Clphp; 4Fphp; 3Fphp; 2Fphp; Aahh; Hbpp; Bhp; Bhh; Hbopp; 4Hb; 6Hh or Hib.

12. The compound according to claim 10 or 11 wherein B is a group, having (L)-configuration, of formula

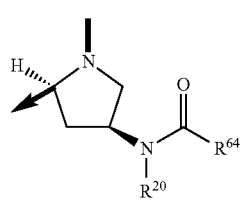

A8″ wherein R20 is H; or lower alkyl; and R64 is alkyl; alkenyl; —[(CH2)u-X]t-CH3, wherein X is —O—, —NR20-, —S—; u=1-3, t=1-6; aryl; aryl-lower alkyl; or heteroaryl-lower alkyl.

13. The compound according to claim 12 wherein R64 is n-hexyl; n-heptyl; 4-(phenyl)benzyl; diphenylmethyl, 3-amino-propyl; 5-amino-pentyl; methyl; ethyl; isopropyl; isobutyl; n-propyl; cyclohexyl; cyclohexylmethyl; n-butyl; phenyl; benzyl; (3-indolyl)methyl; 2-(3-indolyl)ethyl; (4-phenyl)phenyl; n-nonyl; CH3-OCH2CH2-OCH2- or CH3-(OCH2CH2)2-OCH2-.

14. The compound according to claim 1 wherein

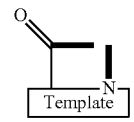

is a group of formula (b1) to (c1);
R1 is H; or lower alkyl;
R20 is H; or lower alkyl;
R30 is H; or methyl;
R31 is H; lower alkyl; lower alkenyl; —(CH2)pOR55 (where R55 is lower alkyl; or lower alkenyl); —(CH2)pNR33R34 (where R33 is lower alkyl; or lower alkenyl; R34 is H; or lower alkyl; or R33 and R34 taken together are —(CH2)2-6-; —(CH2)2O(CH2)2-; —(CH2)2S(CH2)2-; or —(CH2)2NR57(CH2)2-; where R57 is H; or lower alkyl); —(CH2)pOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)pNR20CONR33R81 (where R20 is H; or lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)pN(R20)COR64 (where: R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl, or lower alkenyl; and R59 is H; lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl); —(CH2)oPO(OR60)2 (where R60 is lower alkyl; or lower alkenyl); —(CH2)oSO2R62 (where R62 is lower alkyl; or lower alkenyl); or —(CH2)rC6H4R8 (where R8 is H; F; Cl; CF3; lower alkyl; lower alkenyl; or lower alkoxy); most preferably —CH2CONR58R59 (where R58 is H; or lower alkyl; and R59 is lower alkyl; or lower alkenyl);
R32 is H; or methyl;
R33 is lower alkyl; lower alkenyl; —(CH2)mOR55 (where R55 is lower alkyl; or lower alkenyl); —(CH2)mNR34R63 (where R34 is lower alkyl; or lower alkenyl; R63 is H; or lower alkyl; or R34 and R63 taken together are —(CH2)2-6-; —(CH2)2O(CH2)2-; —(CH2)2S(CH2)2-; or —(CH2)2NR57(CH2)2-; where R57 is H; or lower alkyl); —(CH2)mOCONR75R82 (where R75 is lower alkyl; or lower alkenyl; R82 is H; or lower alkyl; or R75 and R82 taken together are —(CH2)2-6-; —(CH2)2O(CH2)2-; —(CH2)2S(CH2)2-; or —(CH2)2NR57(CH2)2-; where R57 is H; or lower alkyl); —(CH2)mNR20CONR78R82 (where R20 is H; or lower alkyl; R78 is H; or lower alkyl; or lower alkenyl; R82 is H; or lower alkyl; or R78 and R82 taken together are —(CH2)2-6-; —(CH2)2O(CH2)2-; —(CH2)2S(CH2)2-; or —(CH2)2NR57(CH2)2-; where R57 is H; or lower alkyl); —(CH2)mN(R20)COR64 (where: R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl; or lower alkenyl; and R59 is H; lower alkyl; or R58 and R59 taken together are —(CH2)2-6-; —(CH2)2O(CH2)2-; —(CH2)2S(CH2)2-; or —(CH2)2NR57(CH2)2-; where R57: H; or lower alkyl);
R34 is H; or lower alkyl;

R35 is H; lower alkyl; lower alkenyl; (CH2)mOR55 (where R55: lower alkyl; or lower alkenyl); —(CH2)mNR33R34 (where R33 is lower alkyl; or lower alkenyl; R34 is H; or lower alkyl; or R33 and R34 taken together are —(CH2)2-6-; —(CH2)2O(CH2)2-; —(CH2)2S (CH2)2-; or —(CH2)2NR57(CH2)2-; where R57 is H; or lower alkyl); —(CH2)mOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57(CH2)2-; where R57 is H; or lower alkyl); —(CH2)mNR20CONR33R81 (where R20 is H; or lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S (CH2)2-; or —(CH2)2NR57(CH2)2-; where R57 is H; or lower alkyl); —(CH2)mN(R20)COR64 (where: R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl; or lower alkenyl; and R59 is H; lower alkyl; or R58 and R59 taken together are —(CH2)2-6-; —(CH2)2O(CH2)2-; —(CH2)2S(CH2)2-; or —(CH2)2NR57(CH2)2-; where R57 is H; or lower alkyl);

R36 is lower alkyl; lower alkenyl; or aryl-lower alkyl;

R37 is H; lower alkyl; lower alkenyl; —(CH2)pOR55 (where R55 is lower alkyl; or lower alkenyl); —(CH2)pNR33R34 (where R33 is lower alkyl; or lower alkenyl; R34 is H; or lower alkyl; or R33 and R34 taken together are —(CH2)2-6-; —(CH2)2O(CH2)2-; —(CH2)2S (CH2)2-; or —(CH2)2NR57(CH2)2-; where R57 is H; or lower alkyl); —(CH2)pOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(Cl-12)2NR57 (CH2)2-; where R57 is H; or lower alkyl); —(CH2)pNR20CONR33R81 (where R20 is H; or lower alkyl; R33 is H; or lower alkyl; or lower alkenyl; R81 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)pN(R20)COR64 (where: R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl, or lower alkenyl; and R59 is H; lower alkyl; or R58 and R59 taken together are —(CH2)2-6-; —(CH2)2O (CH2)2-; —(CH2)2S(CH2)2-; or —(CH2)2NR57 (CH2)2-; where R57 is H; or lower alkyl); —(CH2)oPO (OR60)2 (where R60 is lower alkyl; or lower alkenyl); —(CH2)oSO2R62 (where R62 is lower alky; or lower alkenyl); or —(CH2)qC6H4R8 (where R8 is H; F; Cl; CF3; lower alkyl; lower alkenyl; or lower alkoxy); and R38 is H; lower alkyl; lower alkenyl; —(CH2)pOR55 (where R55 is lower alkyl; or lower alkenyl); —(CH2)pNR33R34 (where R33 is lower alkyl; or lower alkenyl; R34 is H; or lower alkyl; or R33 and R34 taken together are —(CH2)2-6-; —(CH2)2O(CH2)2-; —(CH2)2S (CH2)2-; or —(CH2)2NR57(CH2)2-; where R57 is H; or lower alkyl); —(CH2)pOCONR33R75 (where R33 is H; or lower alkyl; or lower alkenyl; R75 is lower alkyl; or R33 and R75 taken together are —(CH2)2-6-; —(CH2)2O(CH2)2-; —(CH2)2S(CH2)2-; or —(CH2)2NR57 (CH2)2-; where R57 is H; or lower alkyl); —(CH2)pNR20CONR33R81 (where R20 is H; or lower alkyl; R33 is H; or lower alkyl; or lower alkenyl; R812 is H; or lower alkyl; or R33 and R81 taken together are —(CH2)2-6-; —(CH2)2O(CH2)2-; —(CH2)2S(CH2)2-; or —(CH2)2NR57(CH2)2-; where R57 is H; or lower alkyl); —(CH2)pN(R20)COR64 (where: R20 is H; or lower alkyl; R64 is lower alkyl; or lower alkenyl); —(CH2)oCOOR57 (where R57 is lower alkyl; or lower alkenyl); —(CH2)oCONR58R59 (where R58 is lower alkyl, or lower alkenyl; and R59 is H; lower alkyl; or R58 and R59 taken together are —(CH2)2-6-; —(CH2)2O (CH2)2-; —(CH2)2S(CH2)2-; or —(CH2)2NR57 (CH2)2-; where R57 is H; or lower alkyl); —(CH2)oPO (OR60)2 (where R60 is lower alkyl; or lower alkenyl); —(CH2)oSO2R62 (where R62 is lower alkyl; or lower alkenyl); or —(CH2)qC6H4R8 (where R8 is H; F; Cl; CF3; lower alkyl; lower alkenyl; or lower alkoxy).

15. The compound according to claim 14 wherein R1 is H; R20 is H; R30 is H; R31 is carboxymethyl; or lower alkoxycarbonylmethyl; R32 is H; R35 is methyl; R36 is methoxy; R37 is H and R38 is H.

16. The compound according to claim 2 wherein the template is DPro-LPro or LPro-DPro or a group corresponding thereto but in which the DPro moiety and/or the LPro moiety is substituted as shown in Formula A8' and, respectively, A8":

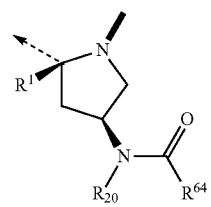

A8' wherein R20 is H or lower alkyl; and R64 is alkyl; alkenyl; —[(CH2)u-X]t-CH3, wherein X is —O—; —NR20-, —S—; u=1-3, t=1-6; aryl; aryl-lower alkyl; or heteroaryl-lower alkyl;

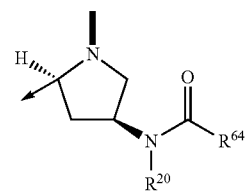

A8"

wherein R20 is H; or lower alkyl; and R64 is alkyl; alkenyl; —[(CH2)u-X]t-CH3, wherein X is —O—, —NR20-, —S—; u=1-3, t=1-6; aryl; aryl-lower alkyl; or heteroaryl-lower alkyl.

17. The compound according to claim 1 wherein the α-amino and/or α-hydroxy acid residues in positions 1 to 14 in the chain Z are:

P1: of type D or of type L;
P2: of type D or of type L;
P3: of type C, type D or of type L;
P4: of type F;
P5: of type E, type F or of type L;
P6: of type C or of type L;
P7: of formula -A-CO—, Gly or Pro
P8: of type E or of type L;
P9: of type E;
P10: of type D;
P11: of type F;

P12: of type D or of type L;
P13: of type F or of type L; and
P14: of type E or of type L; or
P4 and P11, taken together, can form a group of type H;
at P5, P7 and P13 also D-isomers being possible.

18. The compound according to claim 17 wherein the α-amino and/or α-hydroxy acid residues in positions 1 to 14 of the chain Z are:
P1: Tyr, Hhpp;
P2: His, Ahb;
P3: Ala, Lac;
P4: Cys;
P5: Ser, Ahb, DSer, Arg;
P6: Lac, Ala;
P7: DPro;
P8: Dab, Ahb;
P9: Arg;
P10: Tyr;
P11: Cys;
P12: Tyr, Hhpp;
P13: Gln, Hhpp, DGln;
P14: Lys, Ahb;
formation of a disulfide bridge being possible between the Cys residues at P4 and P11.

19. The compound of formula Ia according to claim 1 wherein the template is DPro-LPro, and the residues in position 1-14 of the chain Z are:
P1: Tyr;
P2: His;
P3: Ala;
P4: Cys;
P5: Ser;
P6: Lac;
P7: DPro;
P8: Dab;
P9: Arg;
P10: Tyr;
P11: Cys;
P12: Tyr;
P13: Gln; and
P14: Lys;
Cys at P4 and P11 forming a disulfide bridge.

20. The compound of formula Ia according to claim 1 wherein the template is DPro-LPro, and the residues in position 1-14 of the chain Z are:
P1: Tyr;
P2: His;
P3: Ala;
P4: Cys;
P5: Ser;
P6: Ala;
P7: DPro;
P8: Dab;
P9: Arg;
P10: Tyr;
P11: Cys;
P12: Hhpp;
P13: Gln; and
P14: Lys;
Cys at P4 and P11 forming a disulfide bridge.

21. The compound of formula Ia according to claim 1 wherein the template is DPro-LPro, and the residues in position 1-14 of the chain Z are:
P1: Tyr;
P2: His;
P3: Ala;
P4: Cys;
P5: DSer;
P6: Lac;
P7: DPro;
P8: Dab;
P9: Arg;
P10: Tyr;
P11: Cys;
P12: Tyr;
P13: Gln; and
P14: Lys;
Cys at P4 and P11 forming a disulfide bridge.

22. The compound according to claim 1, wherein said compounds possess CXCR4 antagonizing activity and/or anticancer activity and/or anti inflammatory activity.

23. A pharmaceutical composition containing a compound according to claim 22 and a pharmaceutically inert carrier, wherein said compound possess at least CXCR4 antagonizing activity.

24. The composition according to claim 23 in a form suitable for oral, topical, transdermal, injection, buccal, transmucosal, pulmonary or inhalation administration.

25. The composition according to claim 23 or 24 in form of tablets, dragees, capsules, solutions, liquids, gels, plaster, creams, ointments, syrup, slurries, suspensions, spray, nebuliser or suppositories.

26. A method for slowing or halting viral progression in HIV infected patients; or for slowing or halting a disease mediated or resulting from aberrant CXCR4 receptor activity; which comprises administration of the composition of claim 23, to an individual in need thereof.

27. A process for the manufacture of the compound according to claim 1 which process comprises
(a) coupling an appropriately functionalized solid support with an appropriately N-protected derivative of that amino acid or an appropriately O-protected derivative of that hydroxy acid which in the desired end-product is in positions 3, 5, 6, 7, 8 or 10, any functional group which may be present in said N-protected amino acid derivative or O-protected hydroxy acid derivative being likewise appropriately protected;
(b) removing the N-protecting or O-protecting group from the product thus obtained;
(c) coupling the product thus obtained with an appropriately N-protected derivative of that amino acid or an appropriately O-protected derivative of that hydroxy acid which in the desired end-product is one position nearer the N-terminal amino acid residue or O-terminal hydroxy acid residue, any functional group which may be present in said N-protected amino acid derivative or O-protected hydroxy acid derivative being likewise appropriately protected;
(d) removing the N-protecting group or O-protecting group from the product thus obtained;
(e) repeating steps (c) and (d) until the N-terminal amino acid residue or O-terminal hydroxy acid residue has been introduced;
(f) coupling the product thus obtained with one of the compounds of the general formulae

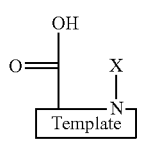

Iia

-continued

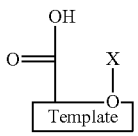
IIb wherein

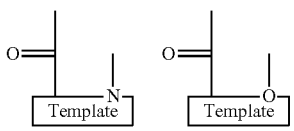

is as defined in according to claim 1, and
X is an N-protecting group and, respectively, an O-protecting group; or, alternatively, if

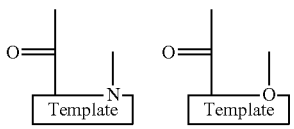

is to be group (a1) or (a2) as defined in claim 1, (fa) coupling the product obtained in step (e) with an appropriately N-protected derivative of an amino acid or an appropriately O-protected derivative of a hydroxy acid of the general formula

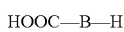 HOOC—B—H     III or

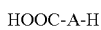 HOOC-A-H     IV wherein B and A are as defined in claim 1, any functional group which may be present in said N-protected amino acid derivative or O-protected hydroxy acid derivative being likewise appropriately protected;

(fb) removing the N-protecting group or O-protecting group from the product thus obtained; and (fc) coupling the product thus obtained with an appropriately N-protected derivative of an amino acid or an appropriately O-protected derivative of a hydroxy acid of the above general formula IV and, respectively, III, any functional group which may be present in said N-protected amino acid derivative or O-protected hydroxy acid derivative being likewise appropriately protected;

(g) removing the N-protecting group or O-protecting group from the product obtained in step (f) or (fc);

(h) coupling the product thus obtained with an appropriately N-protected derivative of that amino acid or an appropriately O-protected derivative of that hydroxy acid which in the desired end-product is in position 14, any functional group which may be present in said N-protected amino acid derivative or O-protected hydroxy acid derivative being likewise appropriately protected;

(i) removing the N-protecting group or O-protecting group from the product thus obtained;

(j) coupling the product thus obtained with an appropriately N-protected derivative of that amino acid or an appropriately O-protected derivative of that hydroxy acid which in the desired end-product is one position farther away from position 14, any functional group which may be present in said N-protected amino acid derivative or O-protected hydroxy acid derivative being likewise appropriately protected;

(k) removing the N-protecting group or O-protecting group from the product thus obtained;

(l) repeating steps (j) and (k) until all amino acid or hydroxy acid residues have been introduced;

(m) if desired, selectively deprotecting one or several protected functional group(s) present in the molecule and appropriately substituting the reactive group(s) thus liberated;

(n) if desired, forming an interstrand linkage between side-chains of appropriate amino acid residues at positions P4 and P11;

(o) detaching the product thus obtained from the solid support;

(p) cyclizing the product cleaved from the solid support;

(q) removing any protecting groups present on functional groups of any members of the chain of amino acid and/or hydroxy acid residues and, if desired, any protecting group(s) which may in addition be present in the molecule; and (r) if desired, converting the product thus obtained into a pharmaceutically acceptable salt or converting a pharmaceutically acceptable, or unacceptable, salt thus obtained into the corresponding free compound of formula Ia or Ib or into a different, pharmaceutically acceptable, salt.

28. A process for the manufacture of the compound according to claim 1 which process comprises (a') coupling an appropriately functionalized solid support with one of the compounds of the general formulae

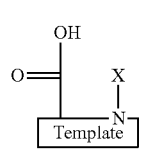
IIa

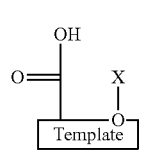
IIb wherein

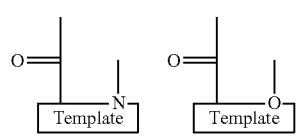

is as defined in claim 1 and X is an N-protecting group or an O-protecting group, or, alternatively, if

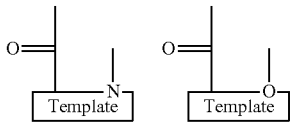

is to be group (a1) or (a2) as defined in claim 1, (a' a) coupling said appropriately functionalized solid support with an appropriately N-protected derivative of an amino acid or an appropriately O-protected derivative of a hydroxy acid of the general formula

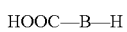 HOOC—B—H        III or

 HOOC-A-H        IV wherein B and A are as defined in claim 1, any functional group which may be present in said N-protected amino acid derivative or O-protected hydroxy acid derivative being likewise appropriately protected;
(a'b) removing the N-protecting group or O-protecting group from the product thus obtained; and
(a'c) coupling the product thus obtained with an appropriately N-protected derivative of an amino acid or an appropriately O-protected derivative of a hydroxy acid of the above general formula IV and, respectively, III, any functional group which may be present in said N-protected amino acid derivative or O-protected hydroxy acid derivative being likewise appropriately protected;
(b') removing the N-protecting group or O-protecting group from the product obtained in step (a') or (a'c)
(c') coupling the product thus obtained with an appropriately N-protected derivative of that amino acid or an appropriately O-protected derivative of that hydroxy acid which in the desired end-product is in position 14, any functional group which may be present in said N-protected amino acid derivative or O-protected hydroxy acid derivative being likewise appropriately protected;
(d') removing the N-protecting group or O-protecting group from the product thus obtained;
(e') coupling the product thus obtained with an appropriately N-protected derivative of that amino acid or an appropriately O-protected derivative of that hydroxy acid which in the desired end-product is one position farther away from position 14, any functional group which may be present in said N-protected amino acid derivative or O-protected hydroxy acid derivative being likewise appropriately protected;
(f') removing the N-protecting group or O-protecting group from the product thus obtained;
(g') repeating steps (e') and (f') until all amino acid or hydroxy acid residues have been introduced;
(h') if desired, selectively deprotecting one or several protected functional group(s) present in the molecule and appropriately substituting the reactive group(s) thus liberated;
(i') if desired forming an interstrand linkage between side-chains of appropriate amino acid residues at positions P4 and P11;

(j') detaching the product thus obtained from the solid support;
(k') cyclizing the product cleaved from the solid support;
(l') removing any protecting groups present on functional groups of any members of the chain of amino acid and/or hydroxy acid residues and, if desired, any protecting group(s) which may in addition be present in the molecule; and
(m') if desired, converting the product thus obtained into a pharmaceutically acceptable salt or converting a pharmaceutically acceptable, or unacceptable, salt thus obtained into the corresponding free compound of formula Ia or Ib or into a different, pharmaceutically acceptable, salt.

29. A process for the manufacture of the compound according to claim 1 in which

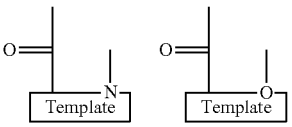

is to be group (a1) or (a2) as defined in claim 1, which process comprises (a"a) coupling an appropriately functionalized solid support with an appropriately N-protected derivative of an amino acid or an appropriately O-protected derivative of a hydroxy acid of the general formula

 HOOC-A-H        IV or

 HOOC—B—H        III wherein A and B are as defined in claim 1, any functional group which may be present in said N-protected amino acid derivative or O-protected hydroxy acid derivative being likewise appropriately protected;
(a"b) removing the N-protecting group or O-protecting group from the product thus obtained;
(b") coupling the product thus obtained with an appropriately N-protected derivative of that amino acid or an appropriately O-protected derivative of that hydroxy acid which in the desired end-product is in position 14, any functional group which may be present in said N-protected amino acid derivative or O-protected hydroxy acid derivative being likewise appropriately protected;
(c") removing the N-protecting group or O-protecting group from the product thus obtained;
(d") coupling the product thus obtained with an appropriately N-protected derivative of that amino acid or an appropriately O-protected derivative of that hydroxy acid which in the desired end-product is one position farther away from position 14, any functional group which may be present in said N-protected amino acid derivative or O-protected hydroxy acid derivative being likewise appropriately protected;
(e") removing the N-protecting group or O-protecting group from the product thus obtained;
(f") repeating steps (d") and (e") until all amino acid or hydroxy acid residues of the chain Z have been introduced;
(g") coupling the product thus obtained with an appropriately N-protected derivative of an amino acid or an appropriately O-protected derivative of a hydroxy acid of the above general formula III and, respectively, IV, any functional group which may be present in said N-protected amino acid derivative or O-protected hydroxy acid derivative being likewise appropriately protected;

(h") removing the N-protecting group or O-protecting group from the product obtained in step ((g")

(i") if desired, selectively deprotecting one or several protected functional group(s) present in the molecule and appropriately substituting the reactive group(s) thus liberated;

(j") if desired forming an interstrand linkage between sidechains of appropriate amino acid residues at positions P4 and P11;

(k") detaching the product thus obtained from the solid support;

(l") cyclizing the product cleaved from the solid support;

(m") removing any protecting groups present on functional groups of any members of the chain of amino acid and/or hydroxy acid residues and, if desired, any protecting group(s) which may in addition be present in the molecule; and (n") if desired, converting the product thus obtained into a pharmaceutically acceptable salt or converting a pharmaceutically acceptable, or unacceptable, salt thus obtained into the corresponding free compound of formula Ia or Ib or into a different, pharmaceutically acceptable, salt.

30. A method of inducing mobilization of stem cells to regulate tissue repair which comprises contacting said stem cells with the compound of claim 1.

31. A method of collecting peripheral blood stem cells by apheresis which comprises contacting said peripheral blood stem cells with the compound of claim 1.

32. A pharmaceutical composition containing the compound according to claim 22 and a pharmaceutically inert carrier, wherein said compound possess at least anti inflammatory activity.

33. A method for treating immuno suppression which comprises administration of the composition of claim 32, to an individual in need thereof.

* * * * *